US006984773B1

(12) United States Patent
Evans et al.

(10) Patent No.: US 6,984,773 B1
(45) Date of Patent: Jan. 10, 2006

(54) TRANSGENIC MICE EXPRESSING A HUMAN SXR RECEPTOR POLYPEPTIDE

(75) Inventors: Ronald M. Evans, La Jolla, CA (US); Bruce Blumberg, Irvine, CA (US); Wen Xie, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 417 days.

(21) Appl. No.: 09/458,366

(22) Filed: Dec. 9, 1999

Related U.S. Application Data

(63) Continuation-in-part of application No. 09/227,718, filed on Jan. 8, 1999, now Pat. No. 6,809,178, which is a continuation-in-part of application No. 09/005,286, filed on Jan. 9, 1998, now Pat. No. 6,756,491.

(51) Int. Cl.
*C12N 5/00* (2006.01)
*C12N 15/00* (2006.01)
*A01K 67/00* (2006.01)
*A01K 67/027* (2006.01)

(52) U.S. Cl. ............................. 800/18; 800/8; 800/25; 435/325

(58) Field of Classification Search ................. 530/300; 536/23.1, 23.4, 23.5; 800/8, 18; 435/325
See application file for complete search history.

(56) References Cited

U.S. PATENT DOCUMENTS

| 4,160,152 A | 7/1979 | Wightman et al. .......... 219/438 |
| 4,256,108 A | 3/1981 | Theeuwes .................... 128/260 |
| 4,265,874 A | 5/1981 | Bonsen et al. ................. 424/15 |

FOREIGN PATENT DOCUMENTS

| WO | 99/19354  | 4/1999 |
| WO | 99/489915 | 9/1999 |
| WO | 99/61622  | 12/1999 |

OTHER PUBLICATIONS

Beato et al. Cell 83:851–57, Dec. 1995.*
Mangelsdorf et al. Cell 83:841–50, Dec. 1995.*
Evans, R. Science 240:889–895, May 1988.*
Seamark, R. Reprod. Fertil. Dev 6:653–7, Feb. 1994.*
Moreadith et al. Journal of Molecular Medicine 75:208–216, 1997.*
Adlercreutz and Mazur, "Phyto–oestrogens and Western Diseases," *Ann. Med.*, 29:95–120 (1997).
Altschul et al., "Basic Local Alignment Search Tool," *J Mol. Biol.*, 215:403–410 (1990).
Baes et al., "A New Orphan Member of the Nuclear Hormone Receptor Superfamily That Interacts with a Subset of Retinoic Acid Response Elements," *Molecular and Cellular Biology*, 14(3):1544–1552 (1994).

Bahouth et al., "Immunological approaches for probing receptor structure and function," *TIPS Reviews*, 12:338–243 (1991).
Bammel et al., "Divergent effects of different enzyme–inducing agents on endogenous and exogenous testosterone," 42:641–644 (1992).
Barwick et al., "Trans–species Gene Transfer for Analysis of Glucocorticoid–Inducible Transcriptional Activation of Transiently Expressed Human CYP3A4 and Rabbit CYP3A6 in Primary Cultures of Adult Rat and Rabbit Hepatocytes," *Molecular Pharmacology*, 50:10–16 (1996).
Beato et al.,"Steroid Hormone Receptors: Many Actors in Search of a Plot," *Cell*, 83:851–857 (1995).
Beaune et al., "Isilation and sequence determination of a cDNA clone related to human cytochrome P–450 nifedipine oxidase," *Proc. Natl. Acad. Sci.*, 83:8064–8068 (1986).
Blumberg et al., "Novel retinoic acid receptor ligands in Xenopus embryos," *Proc. Natl. Acad. Sci.*, 93:4873–4878 (1996).
Blumberg et al., "BXR, an embryonic orphan nuclear receptor activated by a novel class of endogenous benzoate metabolites," *Genes & Development*, 12:1269–1277 (1998).
Burger et al., "Paradoxioal transcriptional activation of rat liver cytochrome P–450 3A1 by dexamethasone and the antiglucocorticoid pregnenolone 16α–carbonitrile: Analysis by transient transfection into primary monolayer cultures of adult rat hepatocytes," *Proc. Natl. Acad. Sci. (USA)*, 89:2145–2149 (1992).

(Continued)

*Primary Examiner*—Joseph Woitach
(74) *Attorney, Agent, or Firm*—Stephen E. Reiter; Foley & Lardner

(57) ABSTRACT

A novel nuclear receptor, termed the steroid and xenobiotic receptor (SXR), a broad-specificity sensing receptor that is a novel branch of the nuclear receptor superfamily, has been discovered. SXR forms a heterodimer with RXR that can bind to and induce transcription from response elements present in steroid-inducible cytochrome P450 genes in response to hundreds of natural and synthetic compounds with biological activity, including therapeutic steroids as well as dietary steroids and lipids. Instead of hundreds of receptors, one for each inducing compound, the invention SXR receptors monitor aggregate levels of inducers to trigger production of metabolizing enzymes in a coordinated metabolic pathway. Agonists and antagonists of SXR are administered to subjects to achieve a variety of therapeutic goals dependent upon modulating metabolism of one or more endogenous steroids or xenobiotics to establish homeostasis. An assay is provided for identifying steroid drugs that are likely to cause drug interaction if administered to a subject in therapeutic amounts. Transgenic animals are also provided which express human SXR, thereby serving as useful models for human response to various agents which potentially impact P450-dependent metabolic processes.

27 Claims, 15 Drawing Sheets

OTHER PUBLICATIONS

Denison and Whitlock, "Xenobiotic–inducible Transcription of Cytochrome P450 Genes," *Journal of Biological Chemistry,* 270(31):18175–18178 (1995).

Devereux et al., "A comprehensive set of sequence analysis progrmas for the VAX," *Nucleic Acids Research,* 12:387–395 (1984).

Edwards et al., "Changes in Cortisol Metabolism Following Rifampicin Therapy," *The Lancet,* 2:549–551 (1974).

Elshourbagy and Guzelian, "Separation, Purification, and Characterization of a Novel Form of Hepatic Cytochrome P–450 from Rats Treated with Pregnenolone–16α–carbonitrile," *Journal of Biological Chemistry,* 255:1279–1285 (1980).

Enmark and Gustafsson, "Orphan Nuclear Receptors—The First Eight Years," *Mol. Endo.,* 10(11):1293–1307 (1996).

Evans, Ronald M., "The Steroid and Thyroid Hormone Receptor Superfamily," *Science,* 240:889–895 (1988).

Fernandez–Salguero and Gonzalez, "The CYP2A gene subfamily: species defferences, regulation, catalytic activities and role in chemical carcinogenesis," *Pharmacogenetics,* 5:S123–S128 (1995).

Forman et al., "Unique Response Pathways Are Established by Allosteric Interactions among Nuclear Hormone Receptors," *Cell,* 81:541–550 (1995).

Forman et al., "Hypolipidemic drugs, polyunsatured fatty acids, and eicosanoids are ligands for peroxisome proliferator–activated receptors αand δ," *Proc. Natl. Acad. Sci. USA,* 94:4312–4317 (1997).

Gonzalez et al., "Complete cDNA and Protein Sequence of a Pregnenolone 16α–Carbonitrile–induced Cytochrome P–450," *Journal of Biological Chemistry,* 260(12):7435–7441 (1985).

Gonzalez et al., "Pregnenolone 16α–Carbonitrile–Inducible P–450 Gene Family: Gene Conversion and Differential Regulation," *Molecular and Cellular Biology,* 6(8):2969–2976 (1986).

Gonzalez, Frank J., "Human cytochromes P450: problems and prospects," *TIPS Reviews,* 13:346–352 (1992).

Gottlicher et al., "Fatty acids activate a chimera of the clofibric acid–activated receptor and the glucocorticoid receptor," *Proc. Natl. Acad. Sci. USA,* 89:4653–4657 (1992).

Guengerich, F. Peter, "Metabolism of 17αEthynylestradiol in Humans", *Life Sciences,* 47:1981–1988 (1990).

Hankinson, Oliver, "The Aryl Hydrocarbon Receptor Complex," *Annu. Rev. Pharmacol. Toxicol.* 35:307–340 (1995).

Hardwick et al., "Cloning of DNA Complementary to Cytochrome P–450 Induced by Pregnenolone–16αcarbonitrile," *Journal of Biological Chemistry,* 258:10182–10186 (1983).

Henikoff and Henikoff, "Amino acit substitution matrices from protein blocks," *Proc. Natl. Acad. Sci. USA,* 89:10915–10919 (1992).

Heuman et al., "Immunochemical Evidence for Induction of a Common Form of Hepatic Cytochrome P–450 in Rats Treated with Pregnenolone–16α–carbonitrile or other Steroidal or Non–Steroidal Agents," *Molecular Pharmacology,* 21:753–760 (1982).

Hollenberg et al., "Primary structure and experssion of a functional human glucocorticoid receptors cDNA," *Nature,* 318(6047):635–641 (1985).

Hollenberg et al., "Colocalization of DNA–Binding and Transcriptional Activation Functions in the Human Glucocorticoid Receptor," *Cell,* 49:39–46 (1987).

Holtbecker et al., "The Nifedipine–Rifampin Interaction: Evidence for the Induction of Gut Wall Metabolism," *Drug Metabolism and Disposition,* 23(10):1121–1123 (1996).

Jonat et al., "Antitumor Promotion and Antiinflammation: Down–Modulation of AP–1 (Fos/Jun) Activity by Glucocorticoid Hormone," *Cell,* 62:1189–1204 (1990).

Juchau, M.R., "Substrate Specificities and Functions of the P450 Cytochromes," *Life Sciences,* 47:2385–2394 (1990).

Kliewer et al., "Fatty acids and eicosanoids regulate gene expression through direct interactions with peroxisome proliferator–activated receptors α and γ," *Proc. Natl. Acad. Sci. USA,* 94:4318–4323 (1997).

Kliewer et al., "An Orphan Nuclear Receptor Activated by Pregnanes Defines a novel Steroid Signaling Pathway," *Cell,* 92:73–82 (1998).

Kolars et al., "First–pass metabolism of cyclosporin by the gut," *Lancet,* 338:1488–1490 (1991).

Kolars et al., "Identification of Rifampin–inducible P450111A4 (CYP3A4) in Human Small Bowel Enterocytes," *Journal of Clinical Investigation, Inc.,* 90:1871–1878 (1992).

Kyriazopoulou et al., "Rifampicin–Induced Adrenal Crisis In Addisonian Patients Receiving Corticosteroid Replacement Therapy," *Journal of Clinical Endocrinology and Metabolism,* 59(6):1204–1206 (1984).

Kyriazopoulou and Vagenakis, "Abnormal Overnight Dexamethasone Suppression Test in Subjects Receiving Rifampicin Therapy," *Journal of Clinical Endocrinology and Metabolism,* 74(1):315–317 (1992).

Ladias and Karathanasis, "Regulation of the Apolipoprotein AI Gene by ARP–1 a Novel Member of the Steroid Receptor Superfamily," *Science,* 251:561–565 (1991).

Lee et al., "Time course of the changes in prednisolone pharmacokinetics after co–administration or discontinuation of rifampin," *Eur. Journal of Clinical Pharmacology,* 45:287–289 (1993).

Li and Evans, "Ligation independent cloning irrespective of restriction site compatibility," *Nucleic Acids Research,* 25:4165–4166 (1997).

Lonning et al., "Plasma Levels of Estradiol, Estrone, Estrone Sulfate and Sex Hormone Binding Globulin in Patients Receiving Rifampicin," *J. Steroid Biochem.,* 33(4A):631–635 (1989).

Mangelsdorf et al., "The Nuclear Receptor Superfamily: The Second Decade," *Cell,* 83:835–839 (1995).

Mangelsdorf and Evans, "The RXR Heterodimers and Orphan Receptors," *Cell,* 83:841–850 (1995).

McAllister et al., "Rifampicin reduces effectiveness and bioavailability of prednisolone," *British Medical Journal,* 286:923–925 (1983).

Miyata et al., "Transcriptional Elements Directing a Liver–Specific Expression of P450/6βA (CYP3A2) Gene–Encoding Testosterone 6β–Hydroxylase," *Archives of Biochemistry and Biophysics,* 318(1):71–79 (1995).

Molowa et al., "Complete cDNA sequence of a cytochrome P–450 inducible by glucocorticoids in human liver," *Proc. Natl. Acad, Sci. USA,* 83:5311–5315 (1986).

Nebert, Daniel W., "P450 Genes: Structure, Evolution, and Regulation," *Ann. Rev. Biochem.,* 56:945–993 (1987).

Needleman and Wunsoh, "A General Method Applicable to the Search for Similarities in the Amino Acid Sequence of Two Proteins," *Journal of Molecular Biology,* 48:443–453 (1970).

O'Malley and Conneely, "Orphan Receptors: In Search of a Unifying Hypothesis for Activation," *Molecular Endocrinology*, 6:1359–1361 (1992).

Ogura and Evans, "A retinoic acid–triggered cascade of HOXB1 gene activation," *Proc. Natl. Acad. Sci. USA*, 92:387–391 (1995).

Ohnhaus et al., "Urinary Excretion of 6β–Hydroxycortisol and the Time Course Measurement of Enzyme Induction in Man," *Eur. J. Clin. Pharmacol.*, 36:39–46 (1989).

Quattrochi et al., "A Novel cis–Acting Element in a Liver Cytochrome P450 3A Gene Confers Synergistic Induction by Glucocorticoids plus Antiglucocorticoids," *Journal of Biological Chemistry*, 270 (48):28917–28923 (1995).

Russel and Wilson, "Steroid 5α–Reductase: Two Genes/Two Enzymes," *Annu. Rev. Biochem.*, 63:25–61 (1994).

Schuetz and Guzelian, "Induction of Cytochrome P–450 by Glucocorticoids in Rat Liver," *Journal of Biological Chemistry*, 259(3):1999–2006 (1984).

Schuetz and Guzelian, "Induction of Cytochrome P–450 by Glucocorticoids in Rat Liver," *Journal of Biological Chemistry*, 259(3):2007–2012 (1984).

Schule et al., "Functional Antagonism between Oncoprotein c–Jun and the Glucocorticoid Receptor," *Cell*, 62:1217–1226 (1990).

Selye, H., "Hormones and Resistance," *Journal of Pharmaceutical Sciences*, 60(1):1–28 (1971).

Sucov et al., "Characterization of an autoregulated response element in the mouse retinoic acid receptor type β gene," *Proc. Natl. Acad. Sci. USA*, 87:5392–5396 (1990).

Staden, Rodger, "The current status and portability of our sequence banding software," *Nucleic Acids Research*, 14(1):217–231 (1986).

Tezolo et al., "Misdiagnosis of Cushing's Syndrome in a Patient Receiving Rifampicin Therapy for Tuberculosis," *Horm. Metab. Res.*, 27:148–150 (1995).

Umesono et al., "Direct Repeats as Selective Response Elements for the Thyroid Hormone, Retinoic Acid, and Vitamin $D_3$ Receptors," *Cell*, 65:1255–1266 (1991).

Watkins et al., "Erythromycin Breath Test as an Assay of Gulcocorticoid–inducible Liver Cytochromes P–450," *J. Clin. Invest.*, 83:688–697 (1989).

Wietholtz et al., "Stimulation of bile acid 6α–hydroxylation by rifampin," *Journal of Hepatology*, 24:713–718 (1996).

Willy et al., "LXR, a nuclear receptor that defines a distinct retinoid response pathway," *Genes & Development*, 9:1033–1045 (1995).

Wurtz et al., "A canonical structure for the ligand–binding domain of nuclear receptors," *Nature Structural Biology*, 3:87–94 1996).

Yang–Yen et al., "Transcriptional Interference between c–Jun and the Glucocorticoid Receptor: Mutual Inhibition of DNA Binding Due to Direct Protein–Protein Interaction," *Cell*, 62:1205–1215 (1990).

Zawawi et al., "The Effects of Therapy with Rifampicin and Isoniazid on Basic Investigations for Cushing's Syndrome," *Ir. j. Med. Sct.*, 165:300–302 (1996).

* cited by examiner

```
ggcacgagga gatctaggtt caaattaatg ttgccccctag tggtaaagga cagagaccct   60
cagactgatg aaatgcgctc agaattactt agacaaagcg gatatttgcc actctcttcc  120
cctttcctg tgtttttgta gtgaagagac ctgaaagaaa aaagtaggga gaacataatg   180
agaacaaata cggtaatctc ttcatttgct ag ttcaagtg ctggacttgg gacttaggag 240
gggcaatgga gccgcttagt gcctacatct gacttggact gaaatatagg tgagagacaa  300
gattgtctca tatccgggga aatcataacc tatgactagg acgggaagag gaagcactgc  360
ctttacttca gtgggaatct cggcctcagc ctgcaagcca agtgttcaca gtgagaaaag  420
caagagaata agctaatact cctgtcctga acaaggcagc ggctccttgg taaagctact  480
ccttgatcga tcctttgcac cggattgttc aaagtggacc ccaggggaga agtcggagca  540
aagaacttac caccaagcag tccaagaggc ccagaagcaa ac ctg gag gtg aga    594
                                                Met Glu Val Arg
                                                 1
```

```
ccc aaa gaa agc tgg aac cat gct gac ttt gta cac tgt gag gac aca   642
Pro Lys Glu Ser Trp Asn His Ala Asp Phe Val His Cys Glu Asp Thr
 5               10                  15                  20 gag tct gtt cct gga aag ccc agt gtc aac gca gat gag gaa gtc gga   690
Glu Ser Val Pro Gly Lys Pro Ser Val Asn Ala Asp Glu Glu Val Gly
             25                  30                  35 ggt ccc caa atc tgc cgt gta tgt ggg gac aag gcc act ggc tat cac   738
Gly Pro Gln Ile Cys Arg Val Cys Gly Asp Lys Ala Thr Gly Tyr His
             40                      45                  50 ttc aat gtc atg aca tgt gaa gga tgc aag ggc ttt ttc agg agg gcc   786
Phe Asn Val Met Thr Cys Glu Gly Cys Lys Gly Phe Phe Arg Arg Ala
             55                  60                  65 atg aaa cgc aac gcc cgg ctg agg tgc ccc ttc cgg aag ggc gcc tgc   834
Met Lys Arg Asn Ala Arg Leu Arg Cys Pro Phe Arg Lys   Gly Ala Cys
         70                  75                  80 gag atc acc cgg aag acc cgg cga cag tgc cag gcc tgc cgc ctg cgc   882
Glu Ile Thr Arg Lys Thr Arg Arg Gln Cys Gln Ala Cys Arg Leu Arg
 85                  90                  9 5                100 aag tgc ctg gag agc ggc atg aag aag gag atc atg tcc gac gag       930
Lys Cys Leu Glu Ser Gly Met Lys Lys Glu Met Ile Met Ser Asp Glu
                 105                 110                 115 gcc gtg gag gag agg cgg gcc ttg atc aag cgg aag aaa agt gaa cgg   978
Ala Val Glu Glu Arg Arg Ala Leu Ile Lys Arg Lys Lys Ser Glu Arg
             120                 125                 130 aca ggg act cag cca ctg gga gtg cag ggg ctg aca gag gag cag cgg  1026
Thr Gly Thr Gln Pro Leu Gly Val Gln Gly Leu Thr Glu Glu Gln Arg
         135                 140                 145 atg atg atc agg gag ctg atg gac gct cag atg aaa acc ttt gac act  1074
Met Met Ile Arg Glu Leu Met Asp Ala Gln Met Lys Thr Phe Asp Thr
 150                 155                 160 acc ttc tcc cat ttc aag aat ttc cgg ctg cca ggg gtg ctt agc agt  1122
Thr Phe Ser His Phe Lys Asn Phe Arg Leu Pro Gly Val Leu Ser Ser
 165                 170                 175                 180
```

FIG. 1A-1

| | | | | | | | | | | | | | | | |
|---|---|---|---|---|---|---|---|---|---|---|---|---|---|---|---|
| ggc | tgc | gag | ttg | cca | gag | tct | ctg | cag | gcc | cca | tcg | agg | gaa | gaa gct | 1170 |
| Gly | Cys | Glu | Leu | Pro | Glu | Ser | Leu | Gln | Ala | Pro | Ser | Arg | Glu | Glu Ala | |
| | | | | 185 | | | | | 190 | | | | | 195 | |
| gcc | aag | tgg | agc | cag | gtc | cgg | aaa | gat | ctg | tgc | tct | ttg | aag | gtc tct | 1218 |
| Ala | Lys | Trp | Ser | Gln | Val | Arg | Lys | Asp | Leu | Cys | Ser | Leu | Lys | Val Ser | |
| | | | | 200 | | | | | 205 | | | | | 210 | |
| ctg | cag | ctg | cgg | ggg | gag | gat | ggc | agt | gtc | tgg | aac | tac | aaa | ccc cca | 1266 |
| Leu | Gln | Leu | Arg | Gly | Glu | Asp | Gly | Ser | Val | Trp | Asn | Tyr | Lys | Pro Pro | |
| | | | | 215 | | | | | 220 | | | | | 225 | |
| gcc | gac | agt | ggc | ggg | aaa | gag | atc | ttc | tcc | ctg | ctg | ccc | cac | atg gct | 1314 |
| Ala | Asp | Ser | Gly | Gly | Lys | Glu | Ile | Phe | Ser | Leu | Leu | Pro | His | Met Ala | |
| | | | | 230 | | | | | 235 | | | | | 240 | |
| gac | atg | tca | acc | tac | atg | ttc | aaa | ggc | atc | atc | agc | ttt | gcc | aaa gtc | 1362 |
| Asp | Met | Ser | Thr | Tyr | Met | Phe | Lys | Gly | Ile | Ile | Ser | Phe | Ala | Lys Val | |
| 245 | | | | | 250 | | | | | 255 | | | | | 260 |
| atc | tcc | tac | ttc | agg | gac | ttg | ccc | atc | gag | gac | cag | atc | tcc | ctg ctg | 1410 |
| Ile | Ser | Tyr | Phe | Arg | Asp | Leu | Pro | Ile | Glu | Asp | Gln | Ile | Ser | Leu Leu | |
| | | | | 265 | | | | | 270 | | | | | 275 | |
| aag | ggg | gcc | gct | ttc | gag | ctg | tgt | caa | ctg | aga | ttc | aac | aca | g tg ttc | 1458 |
| Lys | Gly | Ala | Ala | Phe | Glu | Leu | Cys | Gln | Leu | Arg | Phe | Asn | Thr | Val Phe | |
| | | | | 280 | | | | | 285 | | | | | 290 | |
| aac | gcg | gag | act | gga | acc | tgg | gag | tgt | ggc | cgg | ctg | tcc | tac | tgc ttg | 1506 |
| Asn | Ala | Glu | Thr | Gly | Thr | Trp | Glu | Cys | Gly | y Arg | Leu | Ser | Tyr | Cys Leu | |
| | | | | 295 | | | | | 300 | | | | | 305 | |
| gaa | gac | act | gca | ggt | ggc | ttc | cag | caa | ctt | cta | ctg | gag | ccc | atg ctg | 1554 |
| Glu | Asp | Thr | Ala | Gly | Gly | Phe | Gln | Gln | Leu | Leu | Leu | Glu | Pro | Met Leu | |
| | | | | 310 | | | | | 315 | | | | | 320 | |
| aaa | ttc | cac | tac | atg | ctg | aag | aag | ctg | cag | ctg | cat | gag | gag | gag tat | 1602 |
| Lys | Phe | His | Tyr | Met | Leu | Lys | Lys | Leu | Gln | Leu | His | Glu | Glu | Glu Tyr | |
| 325 | | | | | 330 | | | | | 335 | | | | | 340 |
| gtg | ctg | atg | cag | gcc | atc | tcc | ctc | ttc | tcc | cca | gac | cgc | cca | ggt gtg | 1650 |
| Val | Leu | Met | Gln | Ala | Ile | Ser | Leu | Phe | Ser | Pro | Asp | Arg | Pro | Gly Val | |
| | | | | 345 | | | | | 350 | | | | | 355 | |
| ctg | cag | cac | cgc | gtg | gtg | gac | cag | ctg | cag | gag | caa | ttc | gcc | att act | 1698 |
| Leu | Gln | His | Arg | Val | Val | Asp | Gln | Leu | Gln | Glu | Gln | Phe | Ala | Ile Thr | |
| | | | | 360 | | | | | 365 | | | | | 370 | |
| ctg | aag | tcc | tac | att | gaa | tgc | aat | cgg | ccc | cag | cct | gct | cat | agg ttc | 1746 |
| Leu | Lys | Ser | Tyr | Ile | Glu | Cys | Asn | Arg | Pro | Gln | Pro | Ala | His | Arg Phe | |
| | | | | 375 | | | | | 380 | | | | | 385 | |
| ttg | ttc | ctg | aag | atc | atg | gct | atg | ctc | acc | gag | ctc | cgc | agc | atc aat | 1794 |
| Leu | Phe | Leu | Lys | Ile | Met | Ala | Met | Leu | Thr | Glu | Leu | Arg | Ser | Ile Asn | |
| | | | | 390 | | | | | 395 | | | | | 400 | |

FIG. 1A-2

```
gct cag cac acc cag cgg ctg ctg cgc atc cag gac ata cac ccc ttt      1842
Ala Gln His Thr Gln Arg Leu Leu Arg Ile Gln Asp Ile His Pro Phe
405                 410                 415                 420 gct acg ccc ctc atg cag gag ttg ttc ggt atc aca ggt agc tga          1887
Ala Thr Pro Leu Met Gln Glu Leu Phe Gly Ile Thr Gly Ser
                425                 430 gtggctgtcc ttgggtgaca cctccgagag gtagttagac ccagagccct ctgagtcgcc   1947
actcccgggc caagacagat ggacactgcc aagagccgac aatgccctgc tggcctgtct   2007
ccctagggaa ttcctgctat gacagctggc tagcattcct caggaaggac atggggtgcc   2067
c                                                                    2068
```

| | |
|---|---|
| rCYP3A1 | tagac AGTTCA tga AGTTCA tctac |
| rCYP3A2 | taagc AGTTCA taa AGTTCA tctac |
| rUGT1A6 | actgt AGTTCA taa AGTTCA catgg |

DR-4

| | |
|---|---|
| rbCYP2C1 | caatc AGTTCA acag GGTTCA ccaat |
| rP450R | cac AGGTGA gctg AGGCCA gcagc AGGTCG aaa |

DR-5

| | |
|---|---|
| rCYP2A1 | gtgca GGTTCA actgg AGGTCA acatg |
| rCYP2A2 | gtgct GGTTCA actgg AGGTCA gtatg |
| rCYP2C6 | agtct AGTTCA gtggg GGTTCA gtctt |
| rCYP2E1 | gagat GGTTCA aggaa GGGTCA ttaac |

FIG. 6A

| | |
|---|---|
| CYP3A4 | tagaata TGAACT caaagg AGGTCA gtgagtgg |
| CYP3A5 | tagaata TGAACT caaagg AGGTAA gcaaaggg |
| CYP3A7 | tagaata TTAACT caatgg AGGC.A gtgagtgg |

FIG. 6B

SEQUENCE LISTING

```
<160> NUMBER OF SEQ ID NOS: 44

<210> SEQ ID NO 1
<211> LENGTH: 2068
<212> TYPE: DNA
<213> ORGANISM: Homo sapiens
<220> FEATURE:
<221> NAME/KEY: CDS
<222> LOCATION: (583)..(1887)

<400> SEQUENCE: 1
ggcacgagga gatctaggtt caaattaatg ttgcccctag tggtaaagga cagagaccct      60
cagactgatg aaatgcgctc agaattactt agacaaagcg gatatttgcc actctcttcc     120 cctttcctg tgtttttgta gtgaagagac ctgaaagaaa aaagtaggga gaacataatg      180
agaacaaata cggtaatctc ttcatttgct agttcaagtg ctggacttgg gacttaggag     240
gggcaatgga gccgcttagt gcctacatct gacttggact gaaatatagg tgagagacaa     300
gattgtctca tatccgggga aatcataacc tatgactagg acgggaagag gaagcactgc     360
ctttacttca gtgggaatct cggcctcagc ctgcaagcca agtgttcaca gtgagaaaag     420
caagagaata agctaatact cctgtcctga acaaggcagc ggctccttgg taaagctact     480
ccttgatcga tcctttgcac cggattgttc aaagtggacc ccagggagaa agtcggagca     540
aagaacttac caccaagcag tccagaggcc ccagaagcaa ac ctg gag gtg aga        594
                                                Met Glu Val Arg
                                                  1 ccc aaa gaa agc tgg aac cat gct gac ttt gta cac tgt gag gac aca        642
Pro Lys Glu Ser Trp Asn His Ala Asp Phe Val His Cys Glu Asp Thr
  5                  10                  15                  20 gag tct gtt cct gga aag ccc agt gtc aac gca gat gag gaa gtc gga        690
```

| | | |
|---|---|---|
| Glu Ser Val Pro Gly Lys Pro Ser Val Asn Ala Asp Glu Val Gly<br>            25                      30                      35 | | |
| ggt ccc caa atc tgc cgt gta tgt ggg gac aag gcc act ggc tat cac<br>Gly Pro Gln Ile Cys Arg Val Cys Gly Asp Lys Ala Thr Gly Tyr His<br>              40                      45                      50 | | 738 |
| ttc aat gtc atg aca tgt gaa gga tgc aag ggc ttt ttc agg agg gcc<br>Phe Asn Val Met Thr Cys Glu Gly Cys Lys Gly Phe Phe Arg Arg Ala<br>         55                      60                      65 | | 786 |
| atg aaa cgc aac gcc cgg ctg agg tgc ccc ttc cgg aag ggc gcc tgc<br>Met Lys Arg Asn Ala Arg Leu Arg Cys Pro Phe Arg Lys Gly Ala Cys<br>              70                      75                      80 | | 834 |
| gag atc acc cgg aag acc cgg cga cag tgc cag gcc tgc cgc ctg cgc<br>Glu Ile Thr Arg Lys Thr Arg Arg Gln Cys Gln Ala Cys Arg Leu Arg<br>85                      90                      95                    100 | | 882 |
| aag tgc ctg gag agc ggc atg aag aag gag atg atc atg tcc gac gag<br>Lys Cys Leu Glu Ser Gly Met Lys Lys Glu Met Ile Met Ser Asp Glu<br>                    105                  110                  115 | | 930 |
| gcc gtg gag gag agg cgg gcc ttg atc aag cgg aag aaa agt gaa cgg<br>Ala Val Glu Glu Arg Arg Ala Leu Ile Lys Arg Lys Lys Ser Glu Arg<br>                    120                  125                  130 | | 978 |
| aca ggg act cag cca ctg gga gtg cag ggg ctg aca gag gag cag cgg<br>Thr Gly Thr Gln Pro Leu Gly Val Gln Gly Leu Thr Glu Glu Gln Arg<br>              135                  140                  145 | | 1026 |
| atg atg atc agg gag ctg atg gac gct cag atg aaa acc ttt gac act<br>Met Met Ile Arg Glu Leu Met Asp Ala Gln Met Lys Thr Phe Asp Thr<br>        150                      155                  160 | | 1074 |
| acc ttc tcc cat ttc aag aat ttc cgg ctg cca ggg gtg ctt agc agt<br>Thr Phe Ser His Phe Lys Asn Phe Arg Leu Pro Gly Val Leu Ser Ser<br>165                    170                  175                  180 | | 1122 |
| ggc tgc gag ttg cca gag tct ctg cag gcc cca tcg agg gaa gaa gct<br>Gly Cys Glu Leu Pro Glu Ser Leu Gln Ala Pro Ser Arg Glu Glu Ala<br>                    185                  190                  195 | | 1170 |
| gcc aag tgg agc cag gtc cgg aaa gat ctg tgc tct ttg aag gtc tct<br>Ala Lys Trp Ser Gln Val Arg Lys Asp Leu Cys Ser Leu Lys Val Ser<br>                  200                  205                  210 | | 1218 |
| ctg cag ctg cgg ggg gag gat ggc agt gtc tgg aac tac aaa ccc cca<br>Leu Gln Leu Arg Gly Glu Asp Gly Ser Val Trp Asn Tyr Lys Pro Pro<br>              215                  220                  225 | | 1266 |
| gcc gac agt ggc ggg aaa gag atc ttc tcc ctg ctg ccc cac atg gct<br>Ala Asp Ser Gly Gly Lys Glu Ile Phe Ser Leu Leu Pro His Met Ala<br>        230                      235                  240 | | 1314 |
| gac atg tca acc tac atg ttc aaa ggc atc atc agc ttt gcc aaa gtc<br>Asp Met Ser Thr Tyr Met Phe Lys Gly Ile Ile Ser Phe Ala Lys Val<br>245                    250                  255                  260 | | 1362 |
| atc tcc tac ttc agg gac ttg ccc atc gag gac cag atc tcc ctg ctg<br>Ile Ser Tyr Phe Arg Asp Leu Pro Ile Glu Asp Gln Ile Ser Leu Leu<br>                    265                  270                  275 | | 1410 |
| aag ggg gcc gct ttc gag ctg tgt caa ctg aga ttc aac aca gtg ttc<br>Lys Gly Ala Ala Phe Glu Leu Cys Gln Leu Arg Phe Asn Thr Val Phe<br>                  280                  285                  290 | | 1458 |
| aac gcg gag act gga acc tgg gag tgt ggc cgg ctg tcc tac tgc ttg<br>Asn Ala Glu Thr Gly Thr Trp Glu Cys Gly Arg Leu Ser Tyr Cys Leu<br>              295                  300                  305 | | 1506 |
| gaa gac act gca ggt ggc ttc cag caa ctt cta ctg gag ccc atg ctg<br>Glu Asp Thr Ala Gly Gly Phe Gln Gln Leu Leu Leu Glu Pro Met Leu<br>        310                      315                  320 | | 1554 |
| aaa ttc cac tac atg ctg aag aag ctg cag ctg cat gag gag gag tat<br>Lys Phe His Tyr Met Leu Lys Lys Leu Gln Leu His Glu Glu Glu Tyr<br>325                    330                  335                  340 | | 1602 |

-continued

| | |
|---|---|
| gtg ctg atg cag gcc atc tcc ctc ttc tcc cca gac cgc cca ggt gtg<br>Val Leu Met Gln Ala Ile Ser Leu Phe Ser Pro Asp Arg Pro Gly Val<br>                   345                    350                    355 | 1650 |
| ctg cag cac cgc gtg gtg gac cag ctg cag gag caa ttc gcc att act<br>Leu Gln His Arg Val Val Asp Gln Leu Gln Glu Gln Phe Ala Ile Thr<br>         360                    365                    370 | 1698 |
| ctg aag tcc tac att gaa tgc aat cgg ccc cag cct gct cat agg ttc<br>Leu Lys Ser Tyr Ile Glu Cys Asn Arg Pro Gln Pro Ala His Arg Phe<br>                 375                    380                    385 | 1746 |
| ttg ttc ctg aag atc atg gct atg ctc acc gag ctc cgc agc atc aat<br>Leu Phe Leu Lys Ile Met Ala Met Leu Thr Glu Leu Arg Ser Ile Asn<br>         390                    395                    400 | 1794 |
| gct cag cac acc cag cgg ctg ctg cgc atc cag gac ata cac ccc ttt<br>Ala Gln His Thr Gln Arg Leu Leu Arg Ile Gln Asp Ile His Pro Phe<br>405                    410                    415                    420 | 1842 |
| gct acg ccc ctc atg cag gag ttg ttc ggt atc aca ggt agc tga<br>Ala Thr Pro Leu Met Gln Glu Leu Phe Gly Ile Thr Gly Ser<br>                 425                    430 | 1887 |
| gtggctgtcc ttgggtgaca cctccgagag gtagttagac ccagagccct ctgagtcgcc | 1947 |
| actcccgggc caagacagat ggacactgcc aagagccgac aatgccctgc tggcctgtct | 2007 |
| ccctagggaa ttcctgctat gacagctggc tagcattcct caggaaggac atgggtgcc | 2067 |
| c | 2068 |

<210> SEQ ID NO 2
<211> LENGTH: 434
<212> TYPE: PRT
<213> ORGANISM: Homo sapiens

<400> SEQUENCE: 2

Met Glu Val Arg Pro Lys Glu Ser Trp Asn His Ala Asp Phe Val His
1               5                   10                  15

Cys Glu Asp Thr Glu Ser Val Pro Gly Lys Pro Ser Val Asn Ala Asp
                 20                   25                   30

Glu Glu Val Gly Gly Pro Gln Ile Cys Arg Val Cys Gly Asp Lys Ala
         35                    40                    45

Thr Gly Tyr His Phe Asn Val Met Thr Cys Glu Gly Cys Lys Gly Phe
50                    55                   60

Phe Arg Arg Ala Met Lys Arg Asn Ala Arg Leu Arg Cys Pro Phe Arg
65               70                   75                   80

Lys Gly Ala Cys Glu Ile Thr Arg Lys Thr Arg Arg Gln Cys Gln Ala
                 85                   90                   95

Cys Arg Leu Arg Lys Cys Leu Glu Ser Gly Met Lys Lys Glu Met Ile
                 100                  105                110

Met Ser Asp Glu Ala Val Glu Glu Arg Arg Ala Leu Ile Lys Arg Lys
         115                  120                125

Lys Ser Glu Arg Thr Gly Thr Gln Pro Leu Gly Val Gln Gly Leu Thr
             130                  135                140

Glu Glu Gln Arg Met Met Ile Arg Glu Leu Met Asp Ala Gln Met Lys
145               150                155                160

Thr Phe Asp Thr Thr Phe Ser His Phe Lys Asn Phe Arg Leu Pro Gly
                 165                  170                175

Val Leu Ser Ser Gly Cys Glu Leu Pro Glu Ser Leu Gln Ala Pro Ser
         180                  185                190

Arg Glu Glu Ala Ala Lys Trp Ser Gln Val Arg Lys Asp Leu Cys Ser
             195                  200                205

```
Leu Lys Val Ser Leu Gln Leu Arg Gly Glu Asp Gly Ser Val Trp Asn
    210                 215                 220
Tyr Lys Pro Pro Ala Asp Ser Gly Gly Lys Glu Ile Phe Ser Leu Leu
225                 230                 235                 240
Pro His Met Ala Asp Met Ser Thr Tyr Met Phe Lys Gly Ile Ile Ser
                245                 250                 255
Phe Ala Lys Val Ile Ser Tyr Phe Arg Asp Leu Pro Ile Glu Asp Gln
            260                 265                 270
Ile Ser Leu Leu Lys Gly Ala Ala Phe Glu Leu Cys Gln Leu Arg Phe
        275                 280                 285
Asn Thr Val Phe Asn Ala Glu Thr Gly Thr Trp Glu Cys Gly Arg Leu
    290                 295                 300
Ser Tyr Cys Leu Glu Asp Thr Ala Gly Gly Phe Gln Gln Leu Leu Leu
305                 310                 315                 320
Glu Pro Met Leu Lys Phe His Tyr Met Leu Lys Lys Leu Gln Leu His
                325                 330                 335
Glu Glu Glu Tyr Val Leu Met Gln Ala Ile Ser Leu Phe Ser Pro Asp
            340                 345                 350
Arg Pro Gly Val Leu Gln His Arg Val Val Asp Gln Leu Gln Glu Gln
        355                 360                 365
Phe Ala Ile Thr Leu Lys Ser Tyr Ile Glu Cys Asn Arg Pro Gln Pro
    370                 375                 380
Ala His Arg Phe Leu Phe Leu Lys Ile Met Ala Met Leu Thr Glu Leu
385                 390                 395                 400
Arg Ser Ile Asn Ala Gln His Thr Gln Arg Leu Leu Arg Ile Gln Asp
                405                 410                 415
Ile His Pro Phe Ala Thr Pro Leu Met Gln Glu Leu Phe Gly Ile Thr
            420                 425                 430
Gly Ser

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Putative
      SXR response element from the steroid hydoxylase, rCYP3A1

<400> SEQUENCE: 3
tagacagttc atgaagttca tctac                                       25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Putative
      SXR response element from the steroid hydoxylase, rCYP3A2

<400> SEQUENCE: 4
taagcagttc ataaagttca tctac                                       25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Putative
      SXR response element from the steroid hydoxylase, rUGT1A6
```

```
-continued

<400> SEQUENCE: 5
actgtagttc ataaagttca catgg                                              25

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Putative
      SXR response element from the steroid hydoxylase, rbCYP2C1

<400> SEQUENCE: 6
caatcagttc aacagggttc accaat                                             26

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Putative
      SXR response element from the steroid hydoxylase, rP450R

<400> SEQUENCE: 7
cacaggtgag ctgaggccag cagcaggtcg aaa                                     33

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Putative
      SXR response element from the steroid hydoxylase, rCYP2A1

<400> SEQUENCE: 8
gtgcaggttc aactggaggt caacatg                                            27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Putative
      SXR response element from the steroid hydoxylase, rCYP2A2

<400> SEQUENCE: 9
gtgctggttc aactggaggt cagtatg                                            27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Putative
      SXR response element from the steroid hydoxylase, rCYP2C6

<400> SEQUENCE: 10
agtctagttc agtgggggtt cagtctt                                            27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Putative
      SXR response element from the steroid hydoxylase, hCYP2E1

<400> SEQUENCE: 11
```

```
gagatggttc aaggaagggt cattaac                                              27

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Direct
      repeat with spacer of 0 nucleotides

<400> SEQUENCE: 12
catagtcagg tcaaggtcag atcaac                                               26

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Direct
      repeat with spacer of 1 nucleotides

<400> SEQUENCE: 13
catagtcagg tcataggtca gatcaac                                              27

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Direct
      repeat with spacer of 2 nucleotides

<400> SEQUENCE: 14
catagtcagg tcaataggtc agatcaac                                             28

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Direct
      repeat with spacer of 3 nucleotides

<400> SEQUENCE: 15
catagtcagg tcatataggt cagatcaac                                            29

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Direct
      repeat with spacer of 4 nucleotides

<400> SEQUENCE: 16
catagtcagg tcatataagg tcagatcaac                                           30

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Direct
      repeat with spacer of 5 nucleotides

<400> SEQUENCE: 17
```
catagtcagg tcatatatag gtcagatcaa c                                31

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Direct
      repeat with spacer of 6 nucleotides

<400> SEQUENCE: 18
catagtcagg tcatatataa ggtcaagatc aac                              33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Direct
      repeat with spacer of 7 nucleotides

<400> SEQUENCE: 19
catagtcagg tcatatatat aggtcagatc aac                              33

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Direct
      repeat with spacer of 10 nucleotides

<400> SEQUENCE: 20
catagtcagg tcatatatat ataaggtcag atcaac                           36

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Direct
      repeat with spacer of 15 nucleotides

<400> SEQUENCE: 21
catagtcagg tcatagtagt agtagtagag gtcagatcaa c                     41

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Example of
      a response element suitable for practice of the invention method
<220> FEATURE:
<221> NAME/KEY: modified_base
<222> LOCATION: (7)..(11)
<223> OTHER INFORMATION: This region may encompass 5, 4 or 3
      nucleotides, independently selected from a, c, t or g

<400> SEQUENCE: 22
agttcannnn ntgaact                                                17

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Example of

```
       a response element suitable for practice of the invention method
<220> FEATURE:
<221> NAME/KEY: modified_base
<222> LOCATION: (7)..(12)
<223> OTHER INFORMATION: a, c, t or g

<400> SEQUENCE: 23
tgaactnnnn nnaggtca                                                18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgaactcaaa ggaggtca                                                18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Inverted
      repeat response element with spacer of 0 nucleotides

<400> SEQUENCE: 25
agcttaggtc atgaccta                                                18

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Inverted
      repeat response element with spacer of 1 nucleotides

<400> SEQUENCE: 26
agcttaggtc agtgaccta                                               19

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Inverted
      repeat response element with spacer of 2 nucleotides

<400> SEQUENCE: 27
agcttaggtc acgtgaccta                                              20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Inverted
      repeat response element with spacer of 3 nucleotides

<400> SEQUENCE: 28
agcttaggtc acagtgacct a                                            21

<210> SEQ ID NO 29
<211> LENGTH: 22
<212> TYPE: DNA
```

```
<213> ORGANISM: Artificial Sequence
<220> FEATURE:
<223> OTHER INFORMATION: Description of Artificial Sequence: Inverted
      repeat response element with spacer of 4 nucleotides

<400> SEQUENCE: 29
agcttaggtc acatgtgacc ta                                              22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Inverted
      repeat response element with spacer of 5 nucleotides

<400> SEQUENCE: 30
agcttaggtc acactgtgac cta                                             23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Inverted
      repeat response element with spacer of 6 nucleotides

<400> SEQUENCE: 31
agctttgaac tcaaaggagg tca                                             23

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: IR-M

<400> SEQUENCE: 32
agcttacgtc atgacgta                                                   18

<210> SEQ ID NO 33
<211> LENGTH: 33
<212> TYPE: DNA
<213> ORGANISM: Homo sapiens

<400> SEQUENCE: 33
tagaatatga actcaaagga ggtcagtgag tgg                                  33

<210> SEQ ID NO 34
<211> LENGTH: 33
<212> TYPE: DNA
<213> ORGANISM: Homo sapiens

<400> SEQUENCE: 34
tagaatatga actcaaagga ggtaagcaaa ggg                                  33

<210> SEQ ID NO 35
<211> LENGTH: 32
<212> TYPE: DNA
<213> ORGANISM: Homo sapiens

<400> SEQUENCE: 35
tagaatatta actcaatgga ggcagtgagt gg                                   32

<210> SEQ ID NO 36
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide for PCR

<400> SEQUENCE: 36
gagcaattcg ccattactct gaagt                                              25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide for PCR

<400> SEQUENCE: 37
gtccttgggg tcttctacct ttctc                                              25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide for PCR

<400> SEQUENCE: 38
gacgatttgg atctggacat gttgg                                              25

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide for PCR

<400> SEQUENCE: 39
tgaacttcat gaact                                                         15

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gttttcatct gagcgtccat cagct                                              25

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 41

Arg Gly Lys Thr Cys Ala
 1               5

<210> SEQ ID NO 42
```

-continued

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tgttcttcat gttct                                                          15

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
acaacttcat gaact                                                          15

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Example of
      a response element suitable for practice of the invention method
<220> FEATURE:
<221> NAME/KEY: modified_base
<222> LOCATION: (7)..(11)
<223> OTHER INFORMATION: This region may encompass 5, 4 or 3
      nucleotides, independently selected from a, c, t or g

<400> SEQUENCE: 44
aggtcannnn naggtca                                                        17
```

TRANSGENIC MICE EXPRESSING A HUMAN SXR RECEPTOR POLYPEPTIDE

RELATED APPLICATIONS

This application is a Continuation-in-Part Application of U.S. Ser. No. 09/227,718, filed Jan. 8, 1999, now U.S. Pat. No. 6,809,178 which is, in turn, a Continuation-in-Part of U.S. Ser. No. 09/005,286, filed Jan. 9, 1998, now U.S. Pat. No. 6,756,491 the entire contents of each of which are hereby incorporated by reference herein.

ACKNOWLEDGMENT

This invention was made with Government support under Grant No. GM-26444, awarded by the National Institute of Health. The Government has certain rights in the invention.

FIELD OF THE INVENTION

The present invention relates to intracellular receptors, nucleic acids encoding same, and uses therefor. In a particular aspect, the present invention relates to methods for the modulation of physiological response to elevated levels of steroid and/or xenobiotic compounds.

BACKGROUND OF THE INVENTION

Nuclear receptors constitute a large superfamily of ligand-dependent and sequence-specific transcription factors. Members of this family influence transcription either directly, through specific binding to the promoters of target genes (see Evans, in *Science* 240:889–895 (1988)), or indirectly, via protein-protein interactions with other transcription factors (see, for example, Jonat et al., in *Cell* 62:1189–1204 (1990), Schuele et al., in *Cell* 62:1217–1226 (1990), and Yang-Yen et al., in *Cell* 62:1205–1215 (1990)). The nuclear receptor superfamily (also known in the art as the "steroid/thyroid hormone receptor superfamily") includes receptors for a variety of hydrophobic ligands, including cortisol, aldosterone, estrogen, progesterone, testosterone, vitamin $D_3$, thyroid hormone and retinoic acid, as well as a number of receptor-like molecules, termed "orphan receptors" for which the ligands remain unknown (see Evans, 1988, supra). These receptors all share a common structure indicative of divergence from an ancestral archetype.

Lipophilic hormones such as steroids, retinoic acid, thyroid hormone, and vitamin D3 control broad aspects of animal growth, development, and adult organ physiology. The effects of these hormones are mediated by a large superfamily of intracellular receptors that function as ligand-dependent and sequence-specific transcription factors. The non-steroidal nuclear receptors for thyroid hormone (TR), vitamin D3 (VDR), all-trans retinoic acid (RAR), and fatty acids and eicosanoids (PPAR) form heterodimers with the 9-cis retinoic acid receptor (RXR) that bind bipartite hormone-response elements (HREs) composed of directly repeated half sites related to the sequence AGGTCA (Mangelsdorf and Evans, *Cell* 83:841–850, 1995). In contrast, the steroid receptors function as homodimers and bind to palindromic target sequences spaced by three nucleotides (Beato et al., *Cell* 83:851–857, 1995). In addition to the known receptors, a large group of structurally-related "orphan" nuclear receptors has been described which possess obvious DNA and ligand binding domains, but lack identified ligands (Mangelsdorf et al., *Cell* 83:835–839, 1995; Enmark and Gustafsson, *Mol. Endocrinol.* 10:1293, 1996); and O'Malley and Conneely, *Mol. Endocrinol.* 6:1359, 1992)). Each has the potential to regulate a distinct endocrine signaling pathway.

It is widely viewed that the hormone response is a consequence of the release, from an endocrine gland, of a ligand that circulates through the blood, and coordinately regulates responses in target tissues by acting through specific nuclear receptors. Hormone responsiveness is dependent on the ability to rapidly clear ligand from the blood and the body so that, in absence of a stimulus, target tissues return to a ground state. Hormonal homeostasis is thus achieved by the coordinated release and degradation of bioactive hormones. Steroid hormones and their many metabolites are primarily inactivated by reduction and oxidation in the liver. Since hundreds of adrenal steroids have been identified (e.g., dozens of each of the sex steroids (androgens, estrogens and progestins), 25–35 vitamin D metabolites, and likely hundreds of fatty acids, eicosanoids, hydroxyfats and related bioactive lipids), the problem of efficient ligand elimination is critical to physiologic homeostasis. In addition to the existence of a myriad of endogenous hormones, a similar diversity of ingested plant and animal steroids and bioactive xenobiotic compounds must also be degraded. Such compounds often are lipophilic and may accumulate to toxic levels unless they are metabolized to water-soluble products that can be readily excreted. Therefore, the efficient detoxification of harmful xenobiotics is essential to the survival of all organisms.

Selye first introduced the concept that exogenous steroids and pharmacologic substances may function to modulate the expression of enzymes that would protect against subsequent exposure to toxic xenobiotic substances (H. Selye, *J. Pharm. Sci.* 60:1–28, 1971). These compounds, which Selye called "catatoxic steroids," are typified by the synthetic glucocorticoid antagonist, pregnenolone-16 -carbonitrile (PCN). PCN, and a variety of xenobiotic steroids, induce the proliferation of hepatic endoplasmic reticulum and the expression of cytochrome P450 genes (Burger et al., *Proc. Natl. Acad. Sci. (USA)* 89:2145–2149, 1992; Gonzalez et al., *Mol. Cell. Biol.* 6:2969–2976, 1986; and Schuetz and Guzelian, *J. Biol. Chem.* 259:2007–2012, 1984). Cytochrome P450 (CYP) enzyme(s), present in the endoplasmic reticulum of livers, often catalyze the initial step in such detoxification pathways. P450's are crucial for the detoxification of most xenobiotics, including various environmental pollutants, procarcinogens, and drugs (for review see Denison M S and Whitlock Jr, *J. Biol. Chem.* 270:18175–18178, 1995). In addition, CYPs are also responsible for the reduction and oxidation of steroid hormones and their many metabolites.

One consequence of PCN treatment is the induction of nonspecific "protection" against subsequent exposure to such diverse xenobiotics as digitoxin, indomethacin, barbiturates, and steroids (Selye, supra 1971). Furthermore, it is known that a variety of such compounds can activate P450 genes responsible for their detoxification or degradation (Fernandez-Salguero and Gonzalez, *Pharmacogentics* 5:S123–128, 1995; Denison and Whitlock, supra 1995 ; O. Hankinson, *Ann. Rev. Pharmacol. Toxicol.* 35:307–340, 1995; and Rendic and Di Carlo, *Drug Metab. Rev.* 29:413–580, 1997). P450's constitute a superfamily; each form possesses an overlapping but distinct substrate specificity. Some P450 genes are expressed constitutively, while others, particularly those involved in xenobiotic metabolism, are inducible. In many cases, inducers are also substrates for the induced enzymes, therefore, P450 activities typically remain elevated only as needed. Among the CYP gene family members, the CYP3A isoenzyme is of particular significance from a medical perspective. The human CYP3A4 enzyme is involved in the metabolism of a large number of clinical drugs including antibiotics, antimycotics, glucocorticoids, and the statin class of HMG-CoA reductase inhibitor (Maurel P, *Ioannides C Ed.* (CRC Press, Boca Raton, FL,). pp. 241–270, 1996). Indeed, the drug-induced CYP3A4 activation constitutes the molecular basis for a number of important clinically known drug drug interactions. CYP3A23 and CYP3A11 are rodent homologues of CYP3A4 in rat and mouse, respectively. Indeed, purified CYP3A11 (P450MDX-B) exhibited comparable activity to CYP3A1 (another rat CYP3A homologue, Halvorson, et al., *Arch. Biochem. Biophys.* 277:166–180, 1990) and CYP3A4 (Yamazaki, and Shimada, *Arch. Biochem. Biophys.,* 346:161–169, 1996) for testosterone 6β-hydroxylation, which is thought to be one of specific reactions for the CYP3A enzyme in rodents and primates (Matsunaga et al., 1998). The regions of the 5' regulatory sequences of CYP3A23 and CYP3A11 share high homology, including multiple putative response elements (Toide et al., *Arc. Biochem. Biophy.* 338:43–49, 1997), indicating similar transcriptional regulatory mechanisms among these rodent CYP3A genes.

Although there are substantial structural and catalytic similarities among the various members of the CYP3A family across species lines, important differences exist in regulatory control of these genes (for review, see Gonzalez F J., *Pharmacol. Ther.* 45:1–138, 1990., and Nelson D R., *Arch. Biochem. Biophy.,* 369:1–10, 1999). For example, a clear discrepancy between human and rodents is that the antibiotic RIF induces CYP3A4 in human liver (Watkins et al., *N Engl J Med* 338:916–917, 1985) but does not induce CYP3A23 in rats (Wrighton et al, *Mol Parmacol* 28:312–321, 1985) and CYP3A11 in mice (Schuetz et al., *Proc Natl Acad Sci USA* 93:4001–4005, 1996), respectively. On the other hand, the anti-glucocorticoid PCN, which induces CYP3A23 in rat liver (Wrighton et al, 1985), only weakly induces human CYP3A4 (Schuetz et al., *Hepatology* 18:1254–1262, 1993, Kocarek et al., *Drug Metab Dispos* 23:415–421, 1995, Blumberg et al, *Genes Dev* 12:3149–3155, 1998), and does not induce CYP3A6 (Dalet et al., *DNA* 7:39–46, 1988), a rabbit homolog with a drug response specificity similar to CYP3A4 (Barwick et al., *Mol Pharmacol* 50: 10–16, 1996). Given the widespread metabolic importance of CYP3A, it would be of great clinical benefit to find an appropriate animal model for use in developing a better understanding of the regulatory control and inter-individual heterogeneity in liver expression of CYP3A in humans.

While it appears that catatoxic compounds such as PCN regulate the expression of cytochrome P450s and other detoxifying enzymes, two lines of evidence argue that such regulation is independent of the classical steroid receptors. First, many of the most potent compounds (e.g., PCN, spironolactone, and cyproterone acetate) have been shown to be steroid receptor antagonists; whereas others (e.g., dexamethasone) are steroid receptor agonists (Burger, supra, 1992). Second, the nonspecific protective response remains after bilateral adrenalectomy (and presumably in the absence of adrenal steroids), but not after partial hepatectomy (Selye, supra, 1971).

Insight into the mechanism by which PCN exerts its catatoxic effects is provided by the demonstration that PCN induces the expression of CYP3A1 and CYP3A2, two closely related members of the P450 family of monooxygenases (see, for example, Elshourbagy and Guzelian in *J. Biol. Chem.* 255:1279 (1980); Heuman et al., in *Mol. Pharmacol.* 21:753 (1982); Hardwick et al., in *J. Biol. Chem.* 258:10182 (1983); Scheutz and Guzelian in J. Biol. Chem. 259:2007 (1984); Scheutz et al., in *J. Biol. Chem.* 259:1999 (1984); and Gonzalez et al., in *J. Biol. Chem.* 260:7435 (1985)). The CYP3A hemoproteins display broad substrate specificity, hydroxylating a variety of xenobiotics (e.g., cyclosporin, warfarin and erythromycin), as well as endogenous steroids (e.g., cortisol, progesterone, testosterone and DHEA-sulfate. See, for example, Nebert and Gonzalez in *Ann. Rev. Biochem.* 56:945 (1987) and Juchau in *Life Sci.* 47:2385 (1990)). A PCN response element (which is highly conserved in the CYP3 A2 gene promoter) has since been identified in subsequent studies with the cloned CYP3A1 gene promoter (see Miyata et al., in *Archives Biochem. Biophysics* 318:71 (1995) and Quattrochi et al., in *J. Biol. Chem.* 270:28917 (1995)). This response element comprises a direct repeat of two copies of the nuclear receptor half-site consensus sequence AGTTCA.

In addition to inducing CYP3A gene expression, PCN has also been shown to have marked effects on hepatic cholesterol homeostasis. These effects include significant decreases in the levels of HMG-CoA reductase and cholesterol 7a-hydroxylase gene expression, with associated reductions in sterol biosynthesis and bile acid secretion. PCN has also been reported to enhance the formation of cholesterol esters and the hypersecretion of cholesterol into the bile. Thus, PCN affects key aspects of cholesterol metabolism, including its biosynthesis, storage and secretion.

Activation of orphan nuclear receptor(s) by catatoxic steroids provides a possible mechanism for the induction of xenobiotic metabolizing enzymes by compounds that do not activate known steroid receptors. Because such enzymes are activated by high (pharmacological) doses of xenobiotic and natural steroids, such a "sensor" would be expected to be a broad-specificity, low-affinity receptor. Such receptors could be activated not only by endogenous steroids and metabolites but also by exogenous compounds such as phytosteroids, xenobiotics and pharmacologic inducers. Indeed, it is known that a variety of such compounds can activate P450 genes responsible for their detoxification or degradation (see, for example, Fernandez-Salguero and Gonzalez in *Pharmacogenetics* 5:S123 (1995); Denison and Whitlock, Jr., Supra, 1995); Hankinson in *Ann. Rev. Pharmacol. Toxicol.* 35:307 (1995); and Rendic and Di Carlo in *Drug Metab. Rev.* 29:413 (1997)).

In healthy individuals, steroids levels are tightly regulated with increased catabolism of endogenous steroids being compensated by the pituitary releasing an increase of ACTH, which stimulates biosynthesis, and maintenance of plasma steroid levels. The increased catabolism is reflected by elevated urinary levels of steroid metabolites. Indeed, it is already known that treatment with rifampicin increases urinary metabolites, such as 6β-hydroxycortisol (Ohnhaus et al., *Eur. J. Clin. Pharmacol.* 36:39–46, 1989; and Watkins et al., *J. Clin. Invest.,* 83:688–697, 1989), and bile acid metabolites, such as 6β-hydroxy hyocholic and 6α-hyodeoxycholic acids (Wietholtz et al., *J. Hepatol,* 24:713–718, 1996), while the plasma levels of many circulating steroids rise slightly due to increased synthesis (Lonning et al., *J. Steroid Biochem.* 33:631–635, 1989; Bammel et al., *Eur. J. Pharmacol,* 42:641–644, 1992; and Edwards et al., *Lancet* 2:548–551, 1974).

When synthetic steroids, such as prednisolone (McAllister et al., *Br. Med J.* 286:923–925, 1983 and Lee et al., *Eur. J. Clin. Pharmac,.* 45:287–289, 1993) or 17 α-ethynylestradiol (F. P. Guengerich, *Life Sci.,*

47:1981–1988, 1990) are administered together with rifampicin, plasma levels are rapidly decreased due to enhanced urinary clearance. In some patients undergoing rifampicin therapy for tuberculosis, the increase in urinary steroid levels has led to misdiagnosis of Cushing's syndrome (Kyriazopoulou and Vagenakis, *J. Clin. Endocrinol. Metab.*, 75:315–317, 1992; Zawawi et al., *Ir. J. Med. Sci.* 165:300–302, 1996; and Terzolo et al., *Horm. Metab. Res.*, 27:148–150, 1995). In these patients, steroid production and clearance normalized when rifampicin was withdrawn. In patients with Addison's disease, who mostly lack the ability to synthesize adrenal steroids, rifampicin treatment leads to rapid depletion of endogenous and administered steroids. These documented clinical situations confirm that induction of CYP3A4 causes increased steroid catabolism (Kyriazopoulou et al., *J. Clin. Endocrinol. Metab.* 59:1204–1206, 1984; and Edwards, supra, 1974). However, the art is silent regarding the mechanism by which steroid metabolism is regulated in the body.

Although therapeutically administered steroids are beneficial in achieving therapeutic goals, such compounds can, in some cases, increase the overall level of steroids and xenobiotics above physiologically compatible levels in the subjects to whom they are administered. In other cases, the increased level of steroids and/or xenobiotics may linger in the body longer than is therapeutically required. In addition, some subjects are treated with combinations of steroids and xenobiotics that may be administered separately to treat different conditions, but which, in combination, have an additive, or even synergistic, effect known as a drug interaction. In such cases, the patient may be unaware when a physiologically incompatible level of steroids and xenobiotics has been reached, or when an otherwise therapeutic amount of a steroid becomes potentially dangerous due to combined effects of separately administered drugs.

Thiazolidinediones (TZDs) are a new class of oral antidiabetic agents, and have been identified to be the synthetic ligands for peroxisome proliferator-activated gamma (PPARΓ) (for reviews, see Spiegelman, 1998, and Wilson and Wahli, 1997). Troglitazone is the first TZD introduced for clinical use. Although troglitazone is effective in reducing hyperglycemia, concern has been raised by several reports of severe hepatic dysfunction leading to hepatic failure in patients receiving the drug (Neuschwander-Tetri et al, 1998, Shibuya et al., 1998, and for a review, see Watkins and Whitcomb, 1998). The mechanism of the liver toxicity by TZDs remains largely unknown.

Accordingly, there is still a need in the art for the identification and characterization of broad specificity, low affinity receptors that participate in the mediation of the physiological effect(s) of steroids and xenobiotics, particularly when combinations of such compounds disrupt homeostasis or cause drug interaction.

SUMMARY OF THE INVENTION

In accordance with the present invention, we have isolated and characterized an example of a novel class of human orphan nuclear receptor, termed the steroid and xenobiotic receptor (SXR). SXR is expressed almost exclusively in the liver, the primary site of xenobiotic and steroid catabolism. Unlike classical steroid receptors, SXR heterodimerizes with RXR and binds to directly repeated sequences related to the half-site, AGTTCA. SXR can activate transcription through response elements found in some steroid inducible P450 genes in response to an enormous variety of natural and synthetic steroid hormones, including antagonists such as PCN, as well as xenobiotic drugs, and bioactive dietary compounds, such as phytoestrogen. The ability of SXR to regulate expression of catabolic enzymes in response to this diversity of steroid and/or xenobiotic compounds provides a novel mechanism for direct regulation of metabolism so as to achieve physiologic homeostasis with respect to such steroid and/or xenobiotic compounds—ideal properties for a "steroid sensing receptor" which mediates the physiological effect(s) of hormones. SXR represents the first new class of steroid receptors described since the identification of the mineralocorticoid receptor ten years ago.

In accordance with a particular aspect of the present invention, there are also provided nucleic acid sequences encoding the above-identified receptors, as well as constructs and cells containing same, and probes derived therefrom. There are also provided transgenic animals expressing human SXR. Furthermore, it has also been discovered that a wide variety of substrates modulate the transcription activation effects of invention receptors.

An important requirement for physiologic homeostasis is the removal and detoxification of various endogenous hormones and xenobiotic compounds with biological activity. Much of the detoxification is performed by cytochrome P450 enzymes, many of which have broad substrate specificity and are inducible by a bewildering array of compounds, including steroids. The ingestion of dietary steroids and lipids induces the same enzymes and, thus, must be integrated into a coordinated metabolic pathway. Instead of possessing hundreds of receptors, one for each inducing compound, a class of broad-specificity, low-affinity nuclear receptors has been discovered that monitor total steroid levels and induce the expression of genes encoding xenobiotic metabolizing enzymes. SXR, which is a member of a novel branch of the nuclear receptor superfamily, forms part of a steroid sensor mechanism for removal of elevated levels of steroids and/or xenobiotic compounds from circulation via broad-specificity, low-affinity receptors that represent a novel branch of the nuclear receptor superfamily.

Several lines of evidence suggest SXR functions as a sensor for xenobiotic compounds and/or steroids, acting as a feedback mechanism in the liver to regulate the expression of CYP genes: (1) SXR is expressed at high levels in liver and small intestine, two key tissues for steroid and xenobiotic catabolism; (2) Putative SXR response elements, inverted repeat-6 (IR-6) and direct repeat-3 (DR-3), are found in the catabolic enzymes expressed in these tissues, such as those of the CYP3A4 and CYP3A23, as well as those of P450 oxidoreductase CYP2A, CYP2C, CYP2E, and glucouronosyl transferase, all known to be involved in steroid and xenobiotic catabolism (for a review, see Gonzalez, F. J., *Trends. Pharmacol. Sci.*, 13:346–352, 1992); (3) Compounds known to induce catabolic enzymes such as RIF, nifedipine, steroid agonists and antagonists such as estrogen and tamoxifen, and bioactive dietary compounds such as phytoestrogens, activate a synthetic reporter gene containing these response elements; (4) Some partially metabolized (reduced), but retaining biological activity, are activators of SXR but not classic steroid receptors. The recent isolated PXR is the rodent homolog of SXR. Sequence analysis reveals that SXR and PXR share only about 75% amino acid sequence identity in the ligand binding domain (LDB), in contrast to 95% identity between their DNA binding domains (DBDs) (Blumberg et al., supra, 1998) Comparison of SXR with PXR reveals marked difference in their activation by certain drugs, which may account in part for the species-specific effects of compounds of CYP3A gene expression.

In accordance with the present invention, it has been demonstrated that introduction of human SXR into rodent hepatocytes or into the liver of transgenic mice is sufficient to render a human-like profile of CYP3A gene induction by certain drugs such as RIF. Constitutive activation of SXR and the resulting upregulation of CYP3A gene causes liver toxicity in transgenic mice. In addition, it has been shown that two TZDs, troglitazone and ciglitazone, activate CYP3A gene expression via SXR, but not PXR, both in cell culture and in transgenic mice. The SXR-mediated CYP3A gene activation by TZDs, together with the demonstrated liver toxicity caused by constitutive upregulation of CYP3A in mouse, provides a potential mechanism for the known liver toxicity by certain TZDs.

BRIEF DESCRIPTION OF THE FIGURES

FIG. 1 illustrates that SXR is a novel orphan nuclear receptor.

FIG. 1A shows the sequence of the longest SXR cDNA clone (SEQ ID NO: 1) and a corresponding encoded protein (amino acids 41–434 of SEQ ID NO: 2). The DNA binding domain (amino acids 41–107) is shown in bold, and upstream termination codons in frame with the putative initiator leucine are indicated by asterisks. That this Leu can function as an initiator was demonstrated by SDS-PAGE analysis of labeled proteins produced from in vitro transcribed, translated cDNAs. The unmodified cDNAs yielded a translation product indistinguishable in size from that produced when the leucine was changed to methionine, albeit not nearly as efficient.

FIG. 6A–C are a series of illustrations indicating that SXR can activate responsive elements found in various steroid and xenobiotic inducible P450 enzymes.

FIG. 6A presents a schematic comparison of nucleotide sequences encoding response elements found in inducible cytochrome P450 enzymes (SEQ ID NOS 3–11, respectively in order of appearance). A database search for repeats of the sequence RGKTCA (SEQ ID NO: 41) was performed and some of the matches for enzymes involved in hepatic steroid hydroxylation are indicated. The standard nomenclature for P450 enzymes has been utilized. P450R is the single P450 oxidoreductase required for hydroxylation of steroids. UGT1A 6 is a rat uridine diphosphate (UDP)-glucuronosyltransferase that conjugates glucuronic acid to hydroxylated steroids.

FIG. 6B presents a schematic comparison of conserved glucocortoid-response elements found in human CYP3 genes. The region of human CYP3A4 (SEQ ID NO: 33) shown is necessary and sufficient for glucocorticoid and rifampicin induction of the full-length promoter. Corresponding regions of CYP3A5 (SEQ ID NO: 34) and CYP3A7 (SEQ ID NO: 35) are shown (Barwick et al., *Mol. Pharmacol.* 50:10–16, 1996).

FIG. 6C is a bar graph showing that SXR can activate through inductible, but not uninducible, CYP3 promoter elements. The ability of SXR to activate tk-CYP3-luc response elements in response to various inducers was tested. Results are shown for 50 $\mu$M compound and represent the mean of triplicate determinations. Refampicin results are shown as open bars; and corticosterone results are shown as filled bard.

FIG. 8A relates to the mouse CYP3A32 cellular promoter reporter which was transfected into primary rat hepatocytes in the absence (open bars) or presence (filled bars) of expression vector for SXR. Cells were subsequently treated with indicated compounds. Results are shown as fold induction over solvent (DMSO), and represent the averages and standard error from triplicate assays. E2, 17β-estradiol; PCN, pregnenolone-16-carbonitrile; 3MC, 3-methylcholanthrene. The concentration of compound is 10 μM with exceptions of phenobarbital and 3 MC (2 mM each). Note the mouse CYP3A23 cellular promoter was activated in rat hepatocytes by RIF in the presence of SXR.

FIG. 8B describes similar transfection assays as described in FIG. 8A except that the human CYP3A4 cellular promoter reporter was used. Note the human CYP3A4 cellular promoter was activated by RIF in rat hepatocytes in the presence of SXR.

FIG. 8C illustrates that the DR-3 element is essential for SXR-mediated activation of CYP3A2, and is interchangeable with the IR-6 element. The wild type (DR3/WT (SEQ ID NO:39), filled bars) or mutant forms (DR3/M1 (SEQ ID NO:42), open bars; DR3/M2 (SEQ ID NO: 43), stippled bars; and DR3/IR6 (SEQ ID NO:24), hatched bars) of CYP3A23 cellular promoter reporters were transfected into primary rat hepatocytes in the presence of expression vector for SXR. The ligand treatment and data presentation are the same as in 8A. RIF, rifampicin; CTZ, clotrimazole. Note the disruptions of DR-3 element (DR 3/M1, and DR3/M2) abrogate the activation of CYP3A23, and the replacement of DR-3 element with IR-6 element (DR3/IR3 ) rescue the responsiveness.

DETAILED DESCRIPTION OF THE INVENTION

Figure 1B:
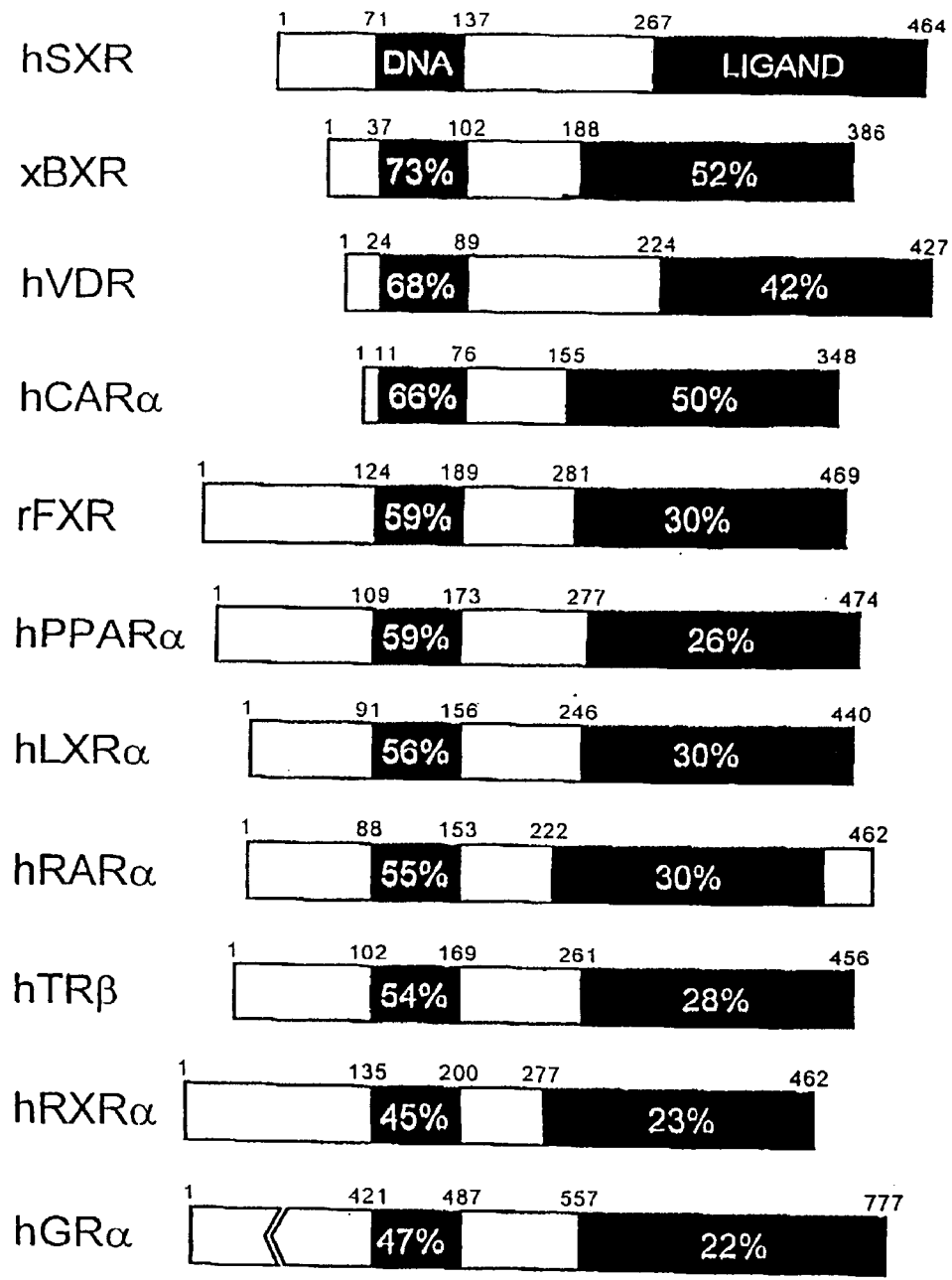
FIG. 1B presents a schematic comparison between SXR and other RXR partners (e.g., the *Xenopus* benzoate X receptor (xBXR), the human vitamin D3 receptor (hVDR), the human constitutively active receptor-alpha (hCARα), the rate farnesoid X the human liver-derived receptor X (LXRα), the human retinoic acid receptor alpha-1 (hRARα-1), the human thyroid hormone receptor beta (hTRβ), the human retinoid X receptor alpha (RXR α) and the human glucocorticoid receptor alpha (hGRα)). Ligand-binding domain boundaries follow those for the canonical nuclear receptor ligand-binding domain (Wurtz et al., *Nature Struct. Biol.* 3:87–94, 1996). Similarity between RXR and other receptors is expressed as percent amino acid identity (indicated in Arabic numerals above each clone). Amino acid residues in the sequences were aligned using the program GAP (Devereaux et al., *Nucl. Acids Res.* 12: 387–395, 1984). DNA=DNA binding domain and LIGAND=ligand binding domain.

In accordance with the present invention, a new class of receptors has been identified that are part of the steroid/thyroid hormone superfamily of receptors, a representative member of which has been designated SXR (or "steroid X receptor"). Invention receptors are characterized by:

forming a heterodimer with retinoid X receptor (RXR), binding to a (direct or inverted) repeat response element motif based on the half site AGTTCA.

activating transcription through response elements found in steroid inducible P450 genes in response to a wide variety of natural and synthetic steroid hormones, and being prominently expressed in the liver and the intestine.

Invention receptor(s) comprise a protein of approximately 464 amino acids (see SEQ ID NO:2) which is most closely, although distantly, related to the *Xenopus* benzoate X receptor (BXR), the vitamin D3 receptor (VDR) and the constitutively activated receptor (CAR). Also provided herein is a 2068 bp cDNA which encodes an example of invention receptors (see SEQ ID NO:1 and FIG. 1A).

In accordance with the present invention, there are also provided method(s) for modulating metabolism of one or more steroid and/or xenobiotic compounds(s) in a subject in need thereof, comprising administering to the subject an effective amount of a modulator of a SXR polypeptide that activates transcription of an endogenous gene operatively associated with a steroid and xenobiotic receptor X (SXR) response element.

In one particular aspect of the invention, a method is provided for preventing steroid toxicity in a subject undergoing treatment of a disease state involving therapeutic administration of one or more steroid compounds. In this embodiment, the invention method comprises administering to such a patient an effective amount of one or more agonists for an invention SXR polypeptide to activate transcription of an endogenous gene operatively associated with one of the invention SXR response elements, thereby preventing increase of the overall level of steroid and xenobiotics above a physiologically acceptable level. The steroid toxicity can result from dietary build-up. (e.g., of estrogens) from drug overdose, (e.g., caused by misdiagnosis of a disease state) or from a drug interaction between therapeutically administered compounds, or between one or more endogenous steroids and one or more dietary and/or therapeutically administered compounds.

Commonly administered therapeutic drugs that tend to accumulate or cause a drug interaction in certain individuals leading to an increase in the overall level of steroid and xenobiotics above a physiologically suitable level include tamoxifen, ralozifene (e.g., in treatment of breast cancer), vitamin K (e.g., in treatment of osteoporosis), calcium channel blockers, such as nifedipine, and the like.

In yet another aspect, the invention provides a method for slowing clearance of a therapeutic steroid or xenobiotic from a subject, such as a human or other mammal, which comprises administering to the subject an effective amount of an antagonist for a SXR polypeptide that activates transcription of an endogenous gene operatively associated with a SXR response element. This aspect of the invention method is useful for controlling too rapid clearance of one or more therapeutic steroids and/or xenobiotics caused by a drug interaction between such compounds.

For example, rifampin (i.e., rifampicin), or an active derivative or analog thereof, is commonly used to treat tuberculosis. Yet rifampin tends to cause hepatic clearance of other therapeutic drugs, such as oral contraceptives (leading to unwanted pregnancy), warfarin (leading to decreased prothrombin times), cyclosporine and prednisone (leading to organ rejection or exacerbations of any underlying inflammatory condition), and verapamil and diltiazem (necessitating increased dosage requirements). A similar situation develops in treatment of osteoporosis with the therapeutic steroid Vitamin K. To overcome these problems, in accordance with the present invention, an effective amount of a SXR polypeptide antagonist is administered to the patient to slow clearance of the therapeutic steroids from the subject.

In yet another aspect, the invention provides a screening assay for determining whether a test compound, or a combination thereof, will activate the invention SXR polypeptide. The assay comprises contacting a host cell line containing as SXR receptor polypeptide, preferably a human or rabbit cell line, with one or more test compound(s) in an appropriate culture medium, wherein the host cell line further contains a reporter vector comprising a promoter that is operable in the cell line operative linked to an invention SXR response element for activation thereof, and DNA encoding a reporter protein operatively linked to the promoter for transcription of the DNA. The invention assay further includes determining whether the reporter protein is present (i.e., expressed by the cell line), wherein a determination that the reporter is present indicates the test compound activates the SXR polypeptide (i.e., an agonist), and a determination that the reporter is not present in the assay predicts the test compound does not activate the invention SXR polypeptide (i.e., not an agonist).

It has been discovered that compound(s) that will activate transcription of the DNA contained in the above-described reporter vector are strong agonists of the invention SXR receptor and fall into the category of "steroids and/or xenobiotic" as the term is used herein.

It has further been discovered that compounds determined by the above assay to activate transcription of the DNA contained in the above described reporter vector are likely to become involved in a drug interaction if administered to a subject at a therapeutic level. More particularly, there is a greater than 30% likelihood, for example a likelihood of about 45% to about 90%, or from about 50% to about 70%, that a therapeutic dose of such a compound will cause a drug interaction as described herein, with other steroids and/or xenobiotics, whether such compounds are endogenously produced, result from dietary sources, or are therapeutically administered to a subject in treatment of a particular disease state. Therefore, in one particular aspect, the invention assay is a method for screening compounds, particularly potential therapeutic compounds, to determine those with at least a 30% likelihood of becoming involved in an undesirable drug interaction if administered to a subject at a therapeutic level. Such a screening assay is a valuable adjunct to any drug development program because it will identify those drug candidates that must be thoroughly screened in vivo to determine their safety, thereby reducing the cost of drug development in general while preventing the possibility that a drug candidate will prove potentially dangerous due to its capacity to cause unhealthy elevation of steroid levels or too rapid clearance of another therapeutically administered compound due to a "drug interaction."

The invention methods are based upon the discovery of a new class of receptors identified as part of the steroid/thyroid hormone superfamily or receptors. The invention receptor, designated herein "the steroid and xenobiotic receptor" (SXR), has been identified as a potential human homolog(s) of the Xenopus benzoate 'X' receptor, BXR (Blumberg et al., *Genes Dev.* 12:1269–1277, 1998). The cDNA encoding one member of the SXR class (SEQ ID NO:1) predicts a protein of 434 amino acids (SEQ ID NO:2) (FIG. 1A), which is 73% identical to BXR in the DNA-binding domain (DBD) and 43% identical in the ligand binding domain (LBD) (FIG. 1B). SXR is most closely related to the recently described pregnane 'X' receptor (Kliewer et al., *Cell* 92:73–82, 1998) (95% identical in the DNA binding domain (DBD), and 73% identical in the ligand binding domain (LBD). SXR is more distantly related to the vitamin D3 receptor and the orphan receptor CAR (Bases et al., *Mol. Cell. Biol.* 14:544–1551, 1994) (FIG. 1B). Other than these receptors, SXR shows no more similarity to other nuclear receptors than the different receptor subfamilies do to each other (FIG. 1B). It is known that true homologs among nuclear receptors typically share considerable similarity, especially in the DBD.

SXR can be further characterized as having a DNA binding domain of about 67 amino acids with 9 Cys residues (i.e., amino acid residues 41–107, as set forth in SEQ ID NO:2), wherein the SXR DNA binding domain has about 73% amino acid identity with the DNA binding domain of the *Xenopus* benzoate X receptor. Alternatively, or in addition, SXR can be further characterized as having a ligand binding domain of at least about 294 amino acids (i.e., at least amino acid residues 141–434, as set forth in SEQ ID NO:2), wherein said ligand binding domain has about 43% amino acid identity with the ligand binding domain of the *Xenopus* benzoate X receptor (FIG. 1B).

A presently preferred SXR polypeptide according to the invention is a polypeptide having substantially the same amino acid sequence as shown in SEQ ID NO:2. As employed herein, the phrase "substantially the same," whether used in reference to the nucleotide sequence of DNA, the ribonucleotide sequence of RNA, or the amino acid sequence of protein, refers to sequences that have slight and non-consequential sequence variations from the actual sequences disclosed herein. Species that are substantially the same are considered to be equivalent to the disclosed sequences and as such are within the scope of the appended claims. In this regard, "slight and non-consequential sequence variations" means that sequences that are substantially the same as the DNA, RNA, or proteins disclosed and/or claimed herein are functionally equivalent to the sequences disclosed and/or claimed herein. Functionally equivalent sequences will function in substantially the same manner to produce substantially the same compositions as the nucleic acid and amino acid compositions disclosed and claimed herein. In particular, functionally equivalent DNAs encode proteins that are the same as those disclosed herein or proteins that have conservation amino acid variations, such as substitution of a non-polar residue for another non-polar residue or a charged residue for a similarly charged residue. These changes include those recognized by those of skill in the art not to substantially alter the tertiary structure of the protein.

An especially preferred SXR polypeptide according to the invention method is a polypeptide having the same amino acid sequence as shown in SEQ ID NO:2.

Thus, the terms "SXR receptor" and "SXR polypeptide" are interchangeable as used herein and are intended to include functional fragments of the invention SXR polypeptide(s). Such fragments include peptides having the DNA binding and/or the ligand binding properties of SXR, e.g. the DNA binding domain thereof (e.g. amino acid residues 41–107 as shown in SEQ ID NO:2), the ligand binding domain thereof (e.g., amino acid residues 141–434 as shown in SEQ ID NO:2.

The modulator(s) useful in the practice of the invention method(s) include both agonists and antagonists of the SXR polypeptide. When the modulator is an agonist, the modulator is characterized as one which activates transcription of a gene encoding a compound active in catabolism of a therapeutic, endogenous, or dietary steroid, or of certain dietary lipids, which gene is characterized by being associated with a SXR response element such that activation of the response element results in transcription of the gene. Generally the gene encodes an enzyme effective in metabolism of one or more steroids or xenobiotic substances, such as dietary lipids and phytoestrogens, and also includes a nucleotide sequence that encodes a SXR response element, for example, one having a direct repeat of a suitable half site (the DR half site) separated by a spacing of 3, 4, or 5 nucleotides, or a direct repeat of a variant thereof. The response element can also comprise an inverse repeat of a suitable half site separated by a 6 nucleotide spacer, or an inverse repeat of a variant thereof, separated by a 6 nucleotide spacer.

Half sites contemplated for use herein have the sequence RGBNNM, wherein:

R is selected from A to G;

B is selected from G, C, or T;

each N is independently selected from A, T, C, or G; and

M is selected from A to C;

with the proviso that as least 4 nucleotides of said-RGBNNM-sequence are identical with the nucleotides at corresponding positions of the sequence AGTTCA.

Examples of response elements suitable for use in practice of the invention methods can be selected from the following:

DR-3,4,5=AGGTCAN$_n$AGGTCA, where n is 3, 4, or 5 (SEQ ID NO:44);

βDR-3,4,5=AGTTCAN$_n$TGAACT, wherein n is 3, 4 or 5 (SEQ ID NO:22); and

IR-=TGAACTN$_n$AGGTCA, wherein n is 6 (SEQ ID NO:23), and the like.

Such response elements are generally found in genes encoding catabolic enzymes, such as CYP2A1, CYP2A2, CYP2C1, CYP3A1, CYP3A2, an P450 oxidoreductase, uridine diphosphate glucuronosyltransferase, or a glucuronosyl transferase, transcription of which genes is activated or suppressed by practice of the invention method(s).

Representative examples of agonists capable of activating transcription of such catabolic enzymes include molecules that have high-affinity receptors, such as progesterone, testosterone, estrogen and corticosterone, as well as their reduced catabolites that are, for the most part, inactive on the high-affinity receptors. In addition to the natural steroids, SXR is activated by synthetic steroids, including PCN and dexamethasone, as well as by xenobiotic drugs, phytosteroids, and the like. The presently preferred agonists include corticosterone, rifampicin, nifedipine, corticosterone, DES, estradiol, dihydrotestosterone, pregnenolone, progesterone, and PCN, with corticosterone being the strongest known activator.

When the modulator is an antagonist of SXR, the modulator functions in one or more of the following ways: (1) to block binding of the polypeptide to the SXR response elements, (2) to inhibit formation of a heterodimer of the polypeptide and a retinoid X receptor, or (3) to inhibit binding of a ligand to the ligand binding domain of SXR or an invention SXR polypeptide. For example, the antagonist can inhibit formation of a heterodimer between a retinoid X receptor and the SXR or an invention SXR polypeptide by blocking the docking site between the molecules. Alternatively, an antagonist can inhibits binding of a ligand to the ligand binding domain of the SXR or invention SXR polypeptide by binding to the active site of the ligand (i.e., the portion of the ligand that binds to the ligand binding domain). Any of a variety of compounds that will accomplish one or more of these goals can be used as an antagonist in the invention methods. For example, an antibody that binds to SXR or to a RXR so as to prevent formation of the of the a SXR:RXR heterodimer can be used as an antagonist in the practice of the present invention. Similarly, an antibody that blocks the ligand binding domain of the SXR receptor without activating transcription of the target gene so as to prevent binding of the ligand to the ligand binding domain will function as an antagonist in the invention method(s).

One of skill in the art will be aware of, or can readily devise, additional polypeptides or nucleotides that will act as antagonists of gene transcription in the invention method(s).

In accordance with another embodiment of the present invention, there are provided heterodimer complexes which consist of the above-described receptor polypeptide and RXR or other silent partner therefor.

In accordance with yet another embodiment of the present invention, there are provided isolated nucleic acids which encode the above-described receptor polypeptides. As used herein, the phrase "isolated nucleic acid" means a nucleic acid that is in a form that does not occur in nature. One means of isolating a nucleic acid encoding a polypeptide is to probe a mammalian genomic library with a natural or artificially designed DNA probe using methods well known in the art. DNA probes derived from the SXR gene are particulary useful for this purpose. DNA and cDNA molecules that encode SXR polypeptides can be used to obtain complementary genomic DNA, cDNA or RNA from human, mammalian (e.g., mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding SXR.

Exemplary DNAs include those which encode substantially the same amino acid sequence as shown in SEQ ID NO:2 (e.g., a contiguous nucleotide sequence which is substantially the same as nucleotides 583–1884 shown in SEQ ID NO:1). Presently preferred DNAs include those which encode the same amino acid sequence as shown in SEQ ID NO:2 (e.g., a contiguous nucleotide sequence which is the same as nucleotides 583–1884 shown in SEQ ID NO:1).

As used herein, nucleotide sequences which are substantially the same share at least about 90% identity, and amino acid sequences which are substantially the same typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention. As readily recognized by those of skill in the art, various ways have been devised to align sequences for comparison, e.g., Blosum 62 scoring matrix, as described by Henikoff and Henikoff in *Proc. Natl. Acad Sci. USA* 89:10915 (1992). Algorithms conveniently employed for this purpose are widely available (see, for example, Needleman and Wunsch in *J. Mol. Bio.* 48:443 (1970).

In accordance with still another embodiment of the present invention, there are provided nucleic acid constructs comprising the above-described nucleic acid, operatively linked to regulatory elements(s) operative for transcription of the nucleic acid and expression of the polypeptide in an animal cell in culture. There are also provided cells containing such a construct, optionally containing a reporter vector comprising:

(a) a promoter that is operable in said cell,
(b) a SXR response element, and
(c) DNA encoding a reporter protein,
   wherein the reporter protein-encoding DNA is operatively linked to the promoter for transcription of the DNA, and
   wherein the promoter is operatively linked to the SXR response element for activation thereof.

In accordance with a further embodiment of the present invention, there are provided methods of making invention receptor polypeptide(s), said methods comprising culturing cells containing an expression vector operable in said cells to express a DNA sequence encoding said polypeptide.

In accordance with a still further embodiment of the present invention, there are provided probes comprising labeled single-stranded nucleic acid, comprising at least 20 contiguous bases in length having substantially the same sequence as any 20 or more contiguous bases selected from bases 1–2068, inclusive, of the DNA illustrated in SEQ ID No:1, or the complement thereof. An especially preferred probe of the invention comprises at least 20 contiguous bases in length having substantially the same sequence as any 20 or more contiguous bases selected from 583–1884, inclusive, of the DNA illustrated in SEQ ID NO:1, or the complement thereof.

Those of skill in the art recognize that probes as described herein can be labeled with a variety of labels, such as for example, radioactive labels, enzymatically active labels, fluorescent labels, and the like. A presently means to label such probes is with $^{32}$P. Such probes are useful, for example, for the identification of receptor polypeptide(s) characterized by being responsive to the presence of one or more steroid and/or xenobiotic to regulate the transcription of associated gene(s), said method comprising hybridizing test DNA with a probe as described herein under high stringency conditions (e.g., contacting probe and test DNA at 65° C. in 0.5 M NaPO$_4$, 7.3, 7% sodium dodecyl sulfate (SDS) and 5% dextran sulfate for 12–24 hours; washing is then carried out 60° C. in 0.1×SSC, 0.1% SDS for three thirty minutes periods, utilizing fresh buffer at the beginning of each wash), and thereafter selecting those sequences which hybridize to said probe.

In another aspect of the invention, the above-described probes can be used to identify invention receptor polypeptide(s), or functional fragments thereof, said methods comprising hybridizing test DNA with a probe as described herein under high stringency conditions, and selecting those sequences which hybridize to said probe.

In yet another aspect of the invention, the above-described probes can be used to assess the tissue sensitivity of an individual to exposure to steroid and steroid-like compounds by determining SXR mRNA levels in a given tissue sample. It is expected that an individual having a high level of SXR mRNA (or protein) will be sensitive to the presence of significant levels of steroid and xenobiotic compounds, such as are encountered in many foods, or as a result of overproduction and/or reduced ability to degrade steroids, as seen in such diseases as Cushing's syndrome, virilism and hirsutism in females, polycystic ovarian syndrome, and the like.

In accordance with yet another embodiment of the present invention, there are provided antibodies which specifically bind the above-described receptor polypeptides. Preferably, such antibodies will be monoclonal antibodies. Those of skill in the art can readily prepare such antibodies having access to the sequence information provided herein regarding invention receptors.

Thus, the above-described antibodies can be prepared employing standard techniques, as are well known to those of skill in the art, using the invention receptor proteins or portions thereof as antigens for antibody production. Both anti-peptide and anti-fusion protein antibodies can be used (see, for example, Bahouth et al. *Trends Pharmacol Sci.* 12:338–343 (1991); *Current Protocols in Molecular Biology* (Ausubel et al., eds.) John Wiley and Sons, New York (1989)). Factors to consider in selecting portions of the invention receptors for use as immunogen (as either a synthetic peptide or a recombinantly produced bacterial fusion protein) include antigenicity, uniqueness to the particular subtype, and the like.

The availability of such antibodies makes possible the application of the technique of immunohistochemistry to monitor the distribution and expression density of invention receptors. Such antibodies could also be employed for diagnostic and therapeutic applications.

In accordance with a further embodiment of the present inventions, binding assays employing SXRs are provided, useful rapidly screening a large number of compounds to determine which compounds (e.g., agonists and antagonists) are capable of binding to the receptors of the invention. Subsequently, more detailed assays can be carried out with initially identified compounds, to further determine whether such compounds act as agonists or antagonists of invention receptors.

The invention binding assays may also be employed to identify new SXR-like ligands. Test samples (e.g., biological fluids) may also be subjected to invention binding assays to detect the presence or absence of SXR or SXR ligands.

Another application of the binding assay of the invention is the assay of test samples (e.g., biological fluids) for the presence or absence of SXR. Thus, for example, tissue homogenates from a patient displaying symptoms thought to be related to over- or under-production of steroids can be assayed to determine if the observed symptoms are related to the presence of SXR.

The binding assays contemplated by the present invention can be carried out in a variety of ways, as can readily be identified by one of skill in the art. For example, competitive binding assays can be employed, as well as radioimmunoassays, ELISA, ERMA, and the like.

In accordance with yet another embodiment of the present invention, there is provided a method of testing a compound for its ability to regulate transcription-activating effects of invention receptor polypeptide(s), said method comprising assaying for the presence or absence of reporter protein upon contacting of cells containing said receptor polypeptide and reporter vector with said compound;
wherein said reporter vector comprises:
(a) a promoter that is operable in said cell,
(b) a hormone response elements, and
(c) DNA encoding a reporter protein,
wherein said reporter protein-encoding DNA is operatively linked to said promoter for transcription of said DNA, and
wherein said promoter is operatively linked to said hormone response element for activation thereof.

Hormone response elements suitable for use in the above-described assay method comprise direct or inverted repeats of at least two half sites (each having the sequence RGBNNM, as defined herein). In each half site, RGBNNM:
R is selected from A or G;
B is selected from G, C, or T;
each N is independently selected from A, T, C, or G; and
M is selected from A or C;
with the proviso that at least 4 nucleotides of said -RGBNNM- sequence are identical with the nucleotides at corresponding positions of the sequence AGTTCA.

Those of skill in the art recognize that the spacing between half sites can vary over a considerable range, typically falling in the range of about 0 up to 15 nucleotides. When the half sites are oriented as direct repeats, it is presently preferred that the half sites be separated by a spacer of 3, 4 or 5 nucleotides. Those of skill in the art recognize that any combination of 3, 4 or 5 nucleotides can be used as the spacer. Direct repeat response elements having a spacer of 4 nucleotides (e.g., SEQ ID NOS:6, 7 or 16) are presently preferred. When the half sites are oriented as inverted repeats, it is presently preferred that the half sites be separated by a spacer of 4, 5 or 6 nucleotides. Those of skill in the art recognize that any combination of 4, 5 or 6 nucleotides can be used as the spacer.

Optionally, the above-described method of testing can be carried out in the further presence of ligand for invention receptors, thereby allowing the identification of antagonists of invention receptors. Those of skill in the art can readily carry out antagonist screens using methods well known in the art. Typically, antagonist screens are carried out using a constant amount of agonist, and increasing amounts of a putative antagonist (i.e., a competitive assay). Alternatively, antagonists can be identified by rendering the receptor constitutively active (e.g., by adding a strong, constitutively-active activator to the receptor) and screening for compounds which shut down the resulting constitutively-active receptor.

In accordance with another aspect of the present invention, there are provided methods to identify compounds which are agonists of steroid X receptor (SXR), but which neither agonize nor antagonize other steroid receptors, said method comprising:
detecting in a first assay system the presence or absence of reporter protein upon contacting of cells containing SXR and reporter vector with said compound;
wherein said reporter vector comprises:
(a) a promoter that is operable in said cell,
(b) an SXR response elements, and
(c) DNA encoding a reporter protein,
wherein said reporter protein-encoding DNA is operatively linked to said promoter for transcription of said DNA, and
wherein said promoter is operatively linked to said SXR response element for activation thereof;
detecting in a second assay system the presence or absence of reporter protein upon contacting of cells containing a steroid hormone receptor other than SXR and reporter vector with said compound;
wherein said reporter vector comprises:
(a) a promoter that is operable in said cell,
(b) a response element for said receptor other than SXR, and
(c) DNA encoding a reporter protein,
wherein said reporter protein-encoding DNA is operatively linked to said promoter for transcription of said DNA, and
wherein said promoter is operatively linked to said response element for said receptor other than SXR for activation thereof; and
identifying those compounds which include production of reporter in said first assay, but not in said second assay, as compounds which are agonists of steroid X receptor (SXR), but neither agonists nor antagonists of other steroid receptors.

Thus, it can readily be seen that invention methods can be used to identify a variety of therapeutically useful compounds. The compounds identified as described herein can be used for the treatment of a wide variety of indications, such as, for example:

a) Cushing'syndrome (hypercortisolism), which manifests as increased cortisol levels, leading to numerous problems including obesity, fatigue, hypertension, edema and osteoporosis;

b) virilism and hirsutism in females due to overproduction of testosterone;

c) androgen excess due to polycystic ovarian syndrome, which manifests as greatly increased circulating level of dehydroepiandrosterone;

d) enzymatic defects which lead to accumulation of specific steroids, such as:
1) 21-hydroxylase deficiency leading to increased synthesis of 17-hydroxy-progesterone and androgens;
2) 11β-hydroxylase deficiency leading to deoxycortisol and deoxycorticosterone accumulation and attendant hypertension;
3) 3β-hydroxysteroid dehydrogenase deficiency resulting in accumulation of pregnenolone and dehydroepi-androsterone, leading to sexual ambiguity in both sexes;
4) 17-hydroxylase deficiency, which prevents cortisol synthesis but leads to accumulation of corticosterone and deoxycorticosterone, resulting in hypertension and aberrant development of secondary sexual characteristics in both sexes;

f) ameliorate the effect of substances in the diet and/or environment which act as endocrine disruptors, e.g., estrogens which may be involved in breast, colorectal and prostate cancers (Adlercreutz and Mazur in Ann. Med. 29:95–120 (1997); and the like.

Compounds which are specific agonists for SXR without acting as either agonists or antagonists for the other steroid receptors will find particular utility where other steroid compounds have been used for their catatoxic properties, while tolerating the negative effects of such therapeutic use (presumably) caused by the undesirable activation of previously described steroid receptors, e.g., glucocorticoid receptor). Compounds which are specific agonists for SXR without acting as either agonists or antagonists for other steroid receptors will find particular utility where other steroid compounds have been used for their catatoxic properties, while tolerating the negative effects of such therapeutic use (presumably caused by the undesirable activation of previously described steroid receptors, e.g., glucocorticoid receptor).

In accordance with a still further embodiment of the present invention, there are provided methods for modulating process(es) mediated by invention receptor polypeptides, said methods comprising conducting said process(es) in the presence of at least one agonist, antagonist or antibody raised against invention receptor.

In accordance with yet another embodiment of the present invention, there are provided methods for inducing the expression of steroid degradative enzymes, said method comprising activating SXR. Exemplary steroid degradative enzymes contemplated for expression herein include steroid hydroxylases, and the like.

In accordance with the present invention, it has further been discovered that induction of some xenobiotic-metabolizing enzymes by pharmacological levels of steroids is regulated by SXR, a class of broad-specificity, low-affinity, nuclear hormone receptors. One benefit of such a receptor-based system is that it induces the expression of xenobiotic metabolizing enzymes only at activator levels sufficiently high to interfere with normal endocrine function. It also makes biological sense that the expression of enzymes with broad substrate specificity, such as cytochrome P450s, can be induced by a receptor responsive to a diverse group of activators, some of which can be substrates for the induced enzymes.

Figure 2:
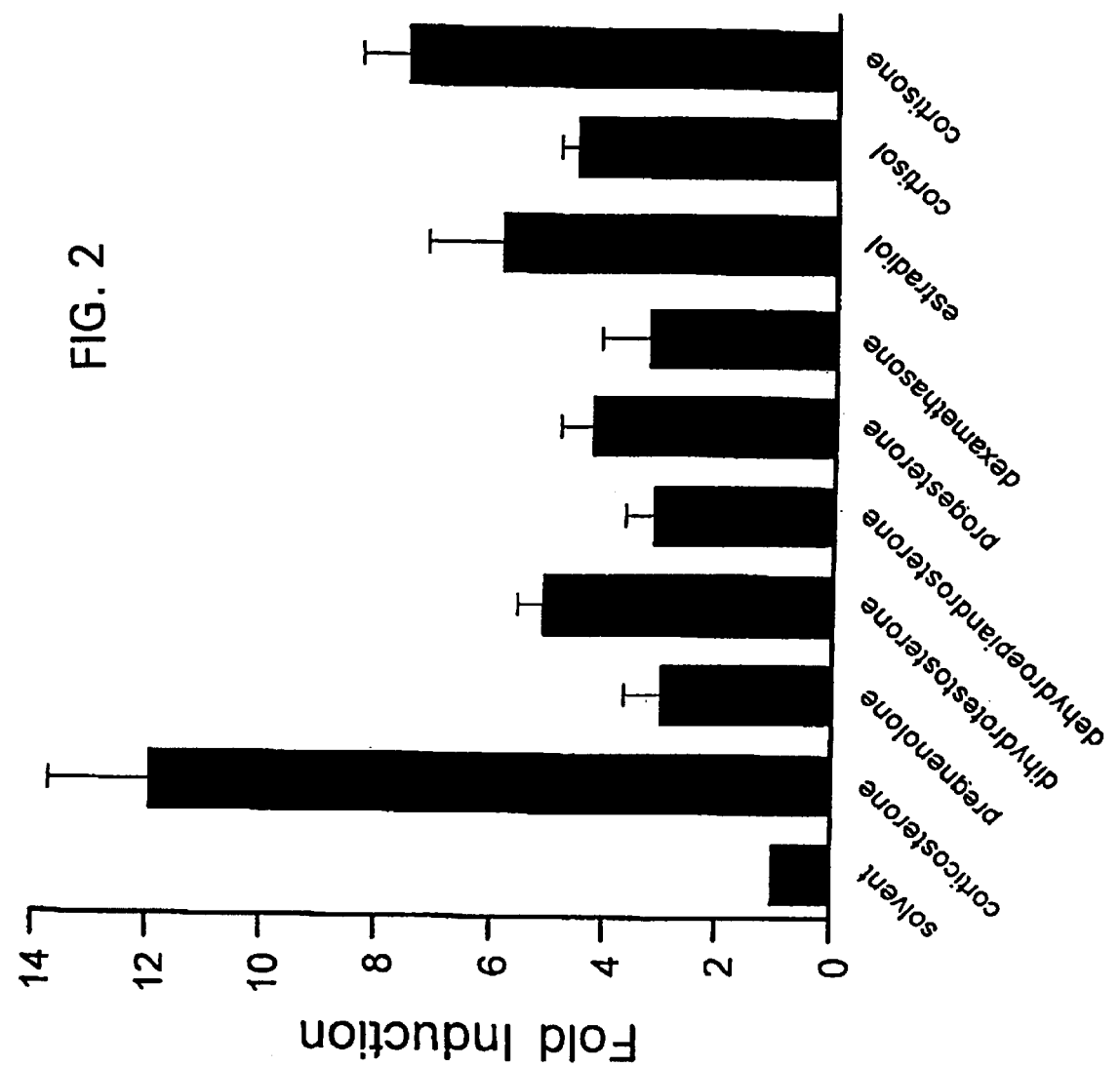
FIG. 2 illustrates that SXR is activated by many steroids. Chimeric receptors composed of the GAL4 DNA-binding domain and the SXR-ligand binding domain were cotransfected into CV-1 cells with the reporter gene tk(MH100)$_4$-luc (Forman et al., *Cell* 81:541–550, 1995). Results are shown as fold induction over solvent (DMSO) control for 50 $\mu$M of steroid and represent the averages and standard error from triplicate assays. Neither reporter alone, nor reporter plus GAL4-DBD, was activated by any of these compounds. Column 1=solvent; Column 2=corticosterone; column 3=pregnenolone; column 4=dihydrotestosterone (DHT); column 5=dehydroepiandrosterone; column 6=progesterone; column 7=dexamethasone; column 7=estradiol; column 8=corisol; and column 9=cortisone.

To determine whether the activity of SXR was ligand-dependent, mixtures of natural and synthetic compounds were tested for their ability to activate SXR in transfection-based assays (see Example 3). A mixture containing dehydroepiandrosterone (DHEA) and pregnenolone was observed to be active, suggesting that SXR might be a new steroid receptor. To characterize its response properties, a large variety of steroids, including intermediate and major products of known steroid biosynthetic pathways were tested. Surprisingly, most of these compounds were active, although there were clear differences in potency (FIG. 2). Indeed, most of the more than 70 steroids tested showed some activity at high doses. Activation was dependent on the ligand binding domain of SXR since both full-length receptors and GAL4-receptor ligand binding domain chimeras showed similar activity, whereas there was no activation of reporter gene expression in experiments with reporter alone or reporter plus GAL4 DNA-binding domain.

The most potent and efficacious activator of the numerous steroids tested is corticosterone. Estradiol and dihydrotestosterone are also remarkably effective activators while aldosterone and 1,25 dihydroxy vitamin D3 are inactive, even at 50 mM. Although ligands for the classical steroid receptors do show some overlap in receptor specificity, there is no example of a nuclear receptor that can be activated by so many different types of steroids. This broad ligand specificity of SXR parallels that of PPARα, which can be activated by an extremely diverse group of dietary fatty acids at micromolar levels (see, for example, Forman et al., in *Proc. Natl. Acad. Sci. USA* 94:4312 (1997) and Gottlicher et al., in *Proc. Natl. Acad. Sci. USA* 89:4653 (1992)).

Figure 3:
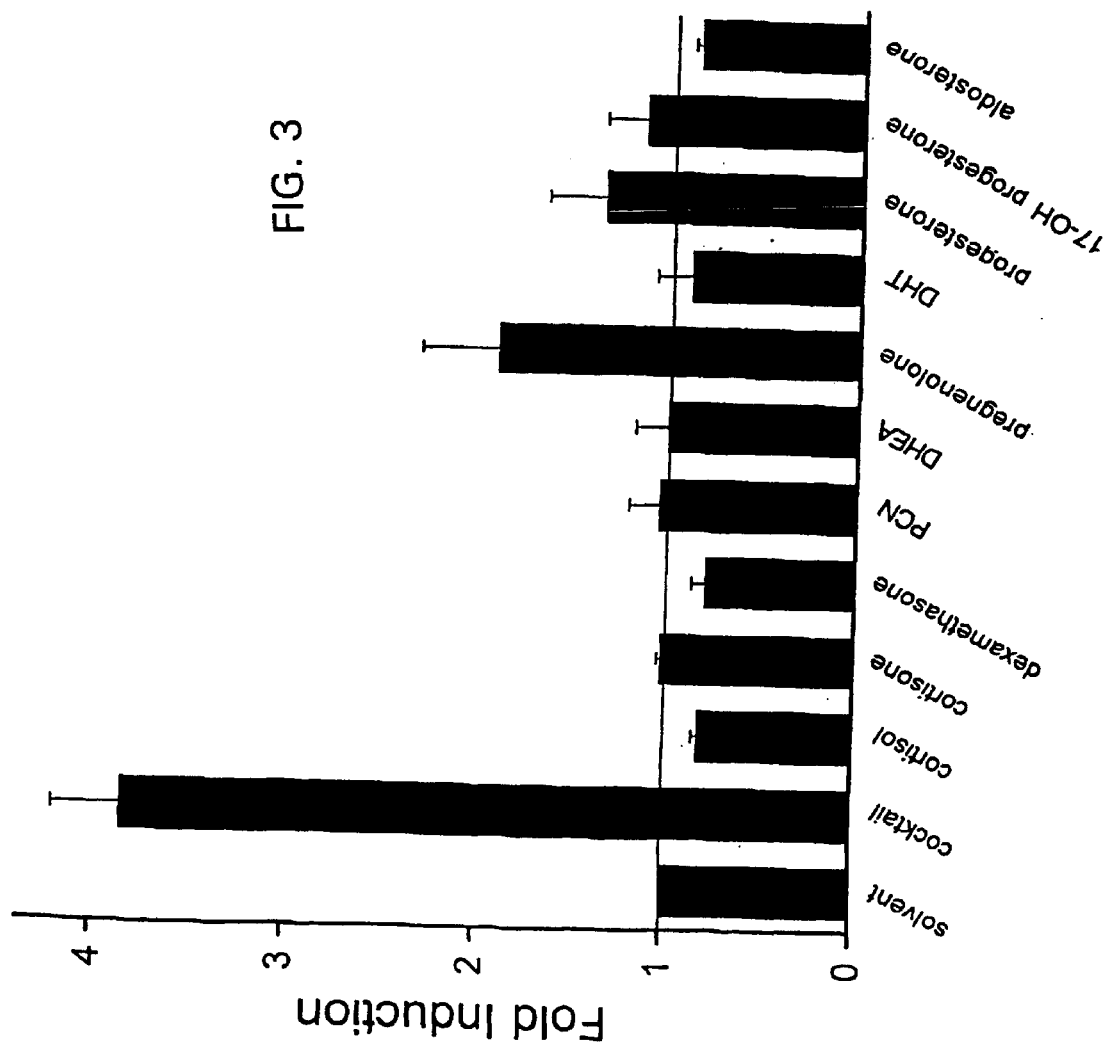
FIG 3. illustrates the ability of steroidal activators to act additively. Thus, the ability of steroidal activators to act additively was tested using full-length SXR and the reporter tk(LXRE)$_3$-luc (see Willy et al., in *Genes Dev.* 9:1033 (1995)). The cocktail contained 10 mM of each steroid for an overall concentration of 100 mM total steroid. The cocktail and its individual components were tested at 100, 10 and 1 mM; results are shown in the Figure for 100 mM cocktail and 10 mM aliquots of the component steroids.

The diversity of steroids showing activity on SXR suggests that this novel class of receptors might be able to sense cumulative, as well as individual steroid levels, predicting that combinations of activators might be more active than the individual components. As shown in FIG. 3, a cocktail containing 10 steroids, each at 10 mM concentration (i.e., an overall steroid concentration of 100 mM), was considerably more active than its individual components at 10 mM, a concentration at which most were inactive. These results confirm that SXR is a broad-specificity, low-affinity, steroid-activated receptor.

An important requirement for physiologic homeostasis is the removal and detoxification of various endogenous hormones and xenobiotic compounds with biological activity. Much of the detoxification is performed by cytochrome P450 enzymes, many of which have broad substrate specificity and are inducible by a bewildering array of compounds, including steroids. The ingestion of dietary steroids and lipids induces the same enzymes and thus, must be integrated into a coordinated metabolic pathway. Instead of possessing hundreds of receptors, one for each inducing compound, the class of receptors described herein indicates the existence of a class of broad-specificity, low-affinity nuclear receptors that monitor total steroid levels and induce the expression of genes encoding xenobiotic metabolizing enzymes. These results indicate the existence of a steroid sensor mechanism for removal of elevated levels of steroids (or steroid-like compounds) from circulation via broad-specificity, low-affinity receptors which represent a novel branch of the nuclear receptor superfamily.

Indeed, a search of the GENBANK database for genes containing putative SXR response elements identified a number of steroid hydroxylases, e.g. CYP2A1, CYP2A2, CYP2C1, CYP2C6, CYP3A1, CYP3A2, P450 oxidoreductase and UDP-glucuronosyltransferase, as candidate target genes. The relevant portions of these sequences are as follows:

| DR-3 | |
| --- | --- |
| rCYP3A1 | tagac AGTTCA tga AGTTCA tctac (SEQ ID NO:3) |
| rCYP3A2 | taagc AGTTCA taa AGTTCA tctac (SEQ ID NO:4) |
| rUGT1A6 | actgt AGTTCA taa AGTTCA catgg (SEQ ID NO:5) |
| DR-4 | |
| rbCYP2C1 | caatc AGTTCA acag GGTTCA ccaat (SEQ ID NO:6) |
| rP450R | cac AGGTGA gctg AGGCCA gcagc AGGTCG aaa (SEQ ID NO:7) |
| DR-5 | |
| rCYP2A1 | gtgca GGTTCA actgg AGGTCA acatg (SEQ ID NO:8) |
| rCYP2A2 | gtgct GGTTCA actgg AGGTCA gtatg (SEQ ID NO:9) |
| rCYP2C6 | agtct AGTTCA gtggg GGTTCA gtctt (SEQ ID NO:10) |
| hCYP2E1 | gagat GGTTCA aggaa GGGTCA ttaac (SEQ ID NO:11) |

Figure 4:
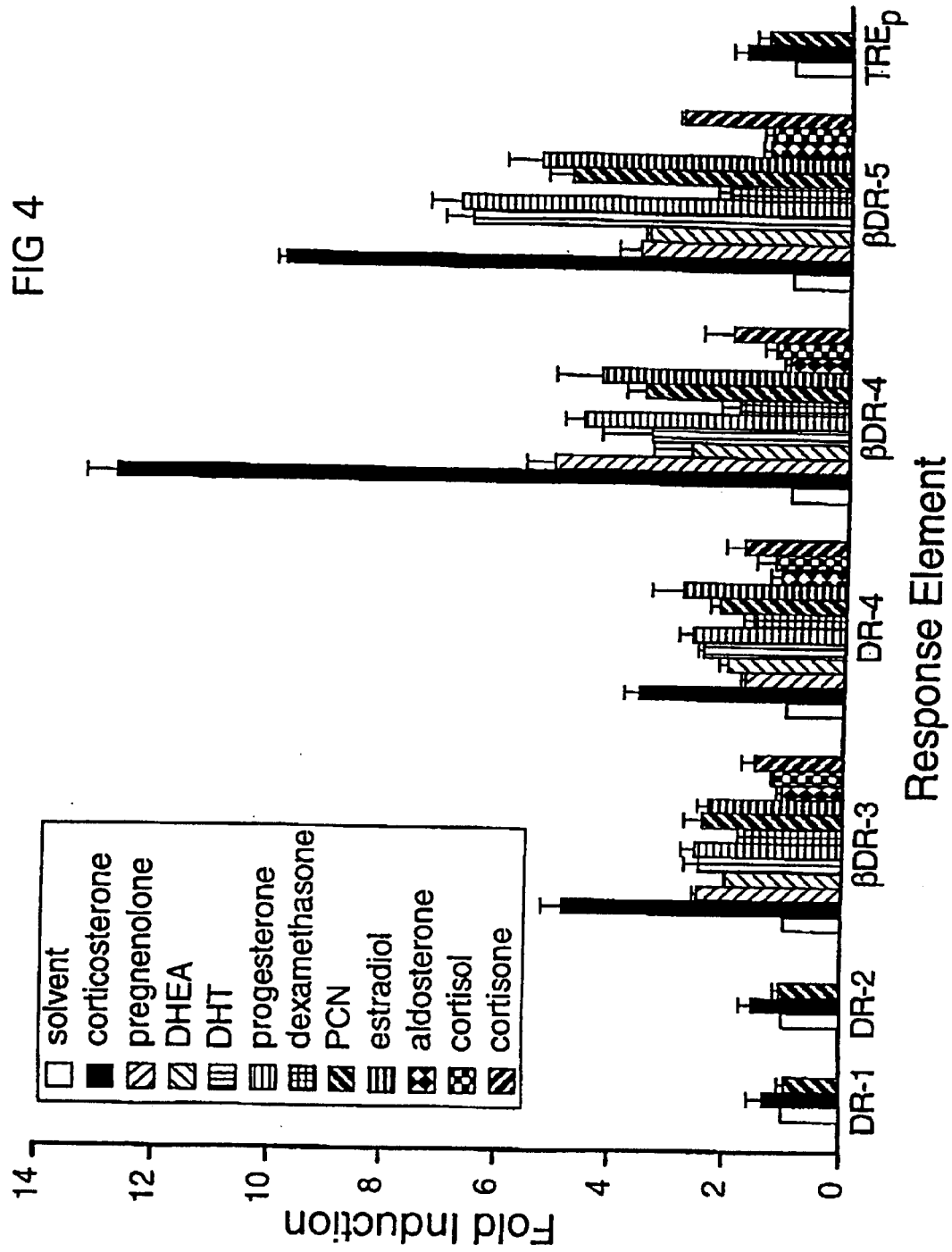
FIG. 4 illustrates the broad activator and response element specificity of SXR. Full-length SXR was tested in cotransfection experiments for its ability to activate elements similar to those in FIG. 3 in response to a panel of steroids at 50 mM. DR-1,2 and TREp were only very slightly activated, hence results are shown only for conticosterone and PCN. The data shown are expressed as mean fold induction over solvent control +/- standard error from triplicate assays.

The data shown in FIG. 4 verify that SXR can activate DR-3, DR-4 and DR-5 elements that are present in these genes. In the series of transfections described in Example 3, corticosterone along with pregnenolone, progesterone, DHT, estradiol and PCN are consistently among the best activators. Dexamethasone, cortisone and DHEA are in the intermediate group with little response from either aldosterone or cortisol (see FIG. 4). Consistent with the DNA-binding data, maximal activities are achieved on 62 DR-3, βDR-4 and βDR-5 elements.

Thus, SXR response elements are found in genes encoding steroid hydroxylases, P450 oxidoreductase, and glucuronosyl transferase. These enzymes can metabolize endogenous as well as xenobiotic compounds and are legitimate targets for a receptor that is activated by pharmacological levels of steroids. SXR is highly expressed in liver, the major expression site of xenobiotic metabolizing enzymes, suggesting that the steroid sensor mechanism is active in the appropriate issue. In addition, prominent expression is also found in the intestine. Although less is known about the role of this tissue in steroid or xenobiotic metabolism, it is certainly possible that the intestine plays a role in regulating the metabolism of dietary, and perhaps endogenous, steroids. Taken together, these data strongly support the existence of a class of low-affinity, broad-specificity nuclear hormone receptor(s), such as SXR, which function as intracellular "steroid sensor(s)".

Figure 5:
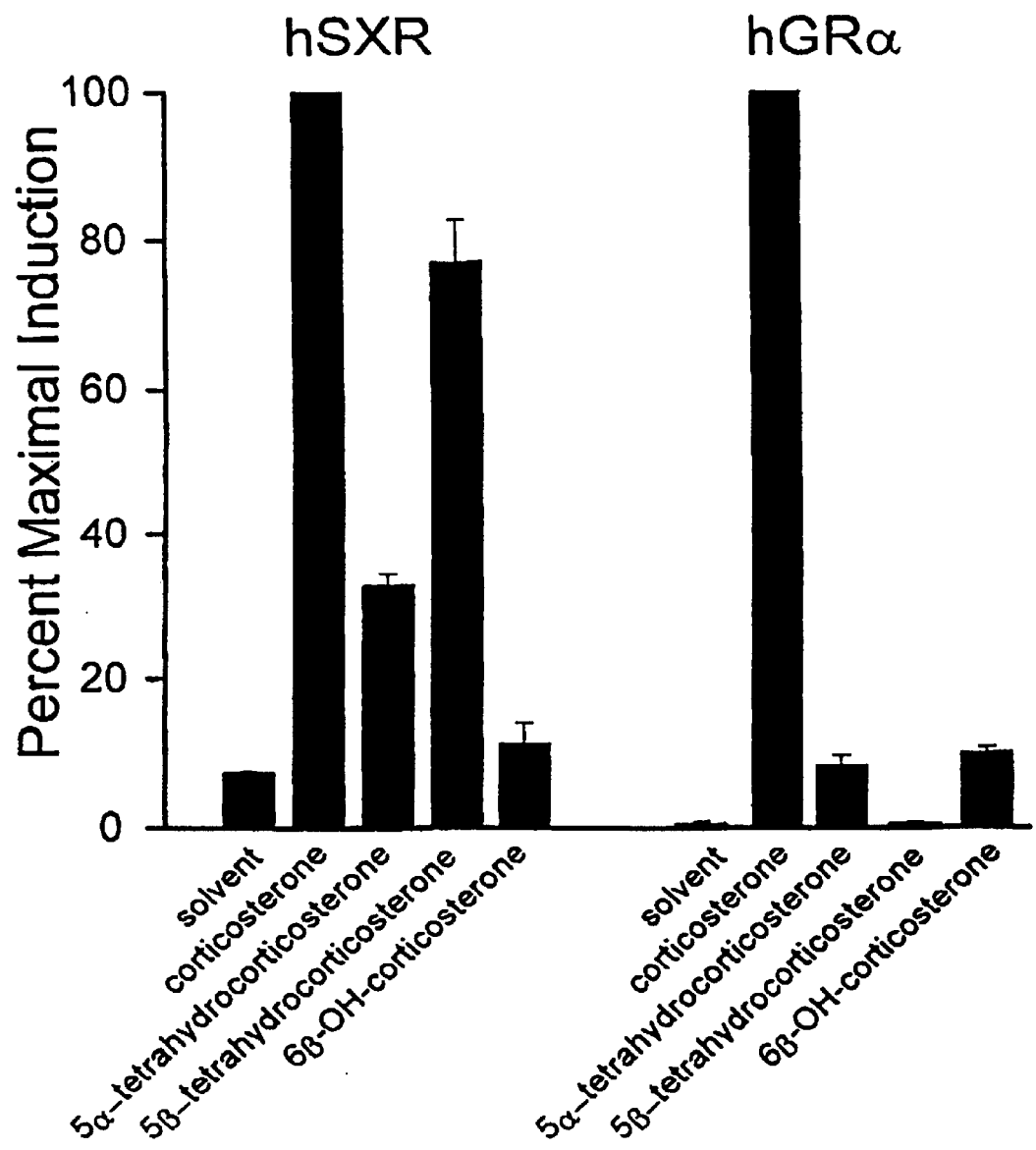
FIG. 5 further illustatres the broad ligand specificity of SXR. Thus, it is seen that reduction of the 4-5 double bond does not inactivate corticosterone. 6β-hydroxylated, non-reduced, 5α and 5β reduced forms of corticosterone were tested for their ability to activate GAL-SXR on tk(MH100)$_4$-luc and hGRa on MTV-luc at 50 mM. Similar results were obtained using full-length SXR.

The localization of apparent SXR-responsive elements in genes encoding steroid hydroxylases raises the question of whether products of steroid catabolism, such as reduced or hydroxylated corticosterone derivatives, could also activate SXR. FIG. 5 shows that both 5α and 5β reduced forms of corticosterone are effective SXR activators where as 5α is slightly active and 5β is completely inactive on GR. While a few 5α-reduced steroids are unable to activate classical steroid receptors (see Russell and Wilson in *Ann. Rev. Biochem.* 63:25 (1994)). Accordingly, the activation of SXR by 5α-reduced steroids reveals a previously unidentified role for these compounds in gene regulation.

6β-hydroxy corticosterone is virtually inactive on SXR and slightly active on GR (see FIG. 5). CYP3A genes, which contain SXR-activatable response elements, catalyze the hydroxylation of many steroids at the 6 position. Therefore, the inability of 6β-hydroxy-corticosterone to activate SXR suggests that 6-hydroxylation is a potential regulatory step in the SXR signaling pathway.

Thus, in support of the role for members of the SXR class of nuclear receptors proposed herein, it has been demonstrated herein that SXR is activated by an extremely diverse group of steroids and their metabolites, including molecules that have high-affinity receptors such as progesterone, testosterone, estrogen and corticosterone as well as their reduced catabolites that are, for the most part, inactive on the high-affinity receptors. In addition to the natural steroids, SXR is activated by synthetic steroids including PCN and dexamethasone. These data provide a molecular explanation for the paradoxical induction of the CYP3A genes (a.k.a. $P450_{PCN}$) by both glucocorticoid receptor agonists and antagonists since the cyp3A genes harbor a SXR-activatable response element in the promoter region that has been shown to be responsible for PCN and glucocorticoid induction (see Burger et al. supra and Gonzalez et al. supra. Whereas such a result is unexplainable by regulation of traditional, high-affinity steroid receptors, such behavior is consistent with the observed properties of the newly characterized steroid X receptor.

Further tests were conducted to discover whether P450s known to be inducible by PCN and other steroids could be SXR targets. The primary human steroid-inducible P450 is the CYP3A4 gene (Molowa et al., *Proc. Natl. Acad. Sci.* (*USA*) 83:5311–5315, 1986, Beaune et al., *Proc. Natl. Acad. Sci.* (*USA* 83:8064–8068, 1986). Unlike the rat and mouse CYP3A genes, all of which contain a DR-3 response element that SXR can activate (FIG. 4), the human and rabbit promoters do not contain such an element. Inducibility of CYP3A4 by steroids and xenobiotics has been localized to an 19 base pair element that is functional in transient transfections assays (Barwick et al., *Mol. Pharmacol.* 50:10–16, 1996). This element contains the IR-6 motif (TGAACTcaaaggAGGTCA) (SEQ ID NO:24). Similar elements have been identified in human CYP3A5, and CYP3A7 and in rabbit CYP3A6 genes (FIG. 6B) (Barwick, supra, 1996). Tests conducted to determine the ability of SXR to bind a series of inverted repeat elements with spacings from zero to six nucleotides determined that only an IR-6 response element, showed significant binding. As with the direct repeats, these results indicate the binding was dependent on formation of a RXR:SXR heterodimer. In addition, competition binding experiments demonstrated little difference in the apparent affinity of SXR:RXR heterodimers for the βDR-4 and CYP3A4 IR-6 response elements. In accord with the known inducibility of the parent promoters, SXR was shown to activate reporter constructs containing the CYP3A4, but not the CYP3A5 or CYP3A7 motifs.

Figure 7A:
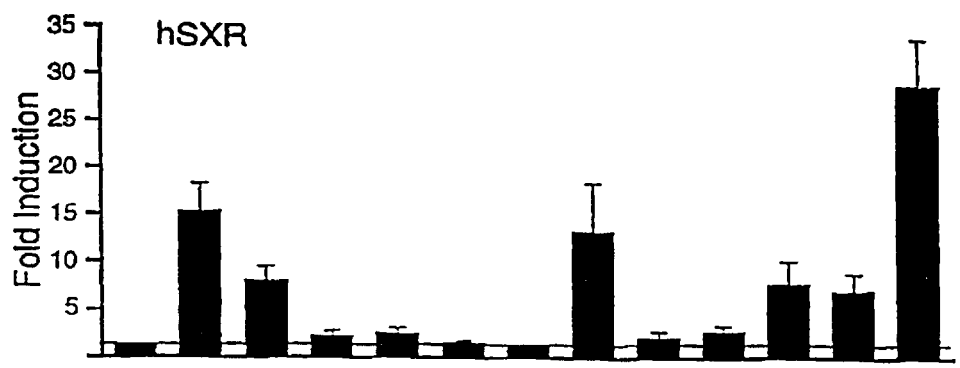
FIGS. 7A–C are bar graphs illustrating the ability of a panel of compounds to activate a representative of three members of the nuclear receptor superfamily, human SXR (FIG. 7A); mouse PXR (FIG. 7B); and human estrogen receptor alpha (hERα). Results are shown for 50 $\mu$M of compound tested, except that the concentration of tamoxifen was 5 $\mu$M; and the concentration of dexamethasone (DEX) was 50 $\mu$M in FIGS. 7A and 7B and 5 $\mu$M in FIG. 7C. Column 1=solvent; column 2=rifamipicin; column 3=nifedipine; column 4=tamoxifen; column 5=spironolactone; column 6=PCN; column 7=DEX; column 8=corticosterone; column 9=cortisone; column 10=DHT; column 11=estradiol; column 12=DES; and column 13=coumestrol.
Figure 7B:
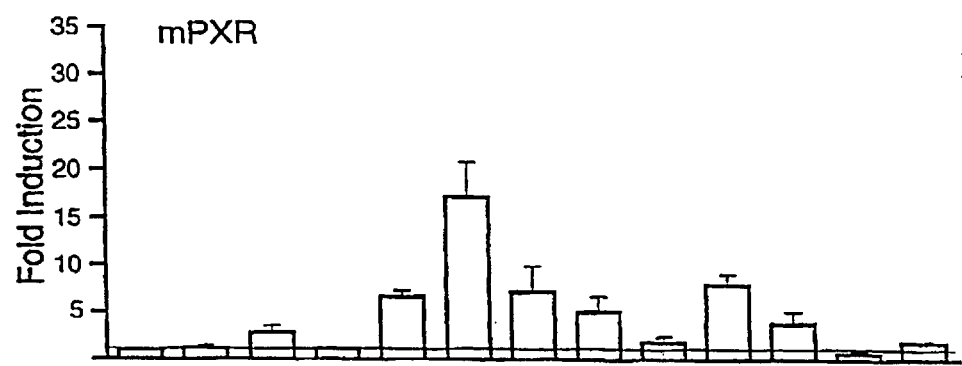

Compounds known to induce CYP3A4 were also shown to activate the invention SXR. The compounds tested included drugs, such as rifampicin and nifedipine; steroid antagonists, such as tamoxifen, spironolactone and PCN; natural and synthetic steroids, such as dexamethasone, diethylstilbestrol, estradiol, dihydrotestosterone, corticosterone and cortisone; and phytoestrogens, such as coumestrol, equol and genistein. Of these compounds, rifampicin, nifedipine, corticosterone, estradiol, DES, and coumestrol were the most potent activators (FIG. 7A. The mouse receptor PXR responded poorly to these inducers, but was preferentially activated by PCN, a weak activator of SXR (FIG. 7B). PXR is reported to be preferentially activated by pregnanes (21-carbon steroids such as dexamethasone (DEX) and pregnenolone) (Kliewer, supra, 1998); however, our tests showed that PXR is similarly activated by 19-carbon androstanes, like testosterone, and 18-carbon estranes, like estradiol (FIG. 7B). Similar results were obtained with other natural steroids, including progesterone, pregnenolone and dihydroethanoic acid (DHEA).

Figure 7C:
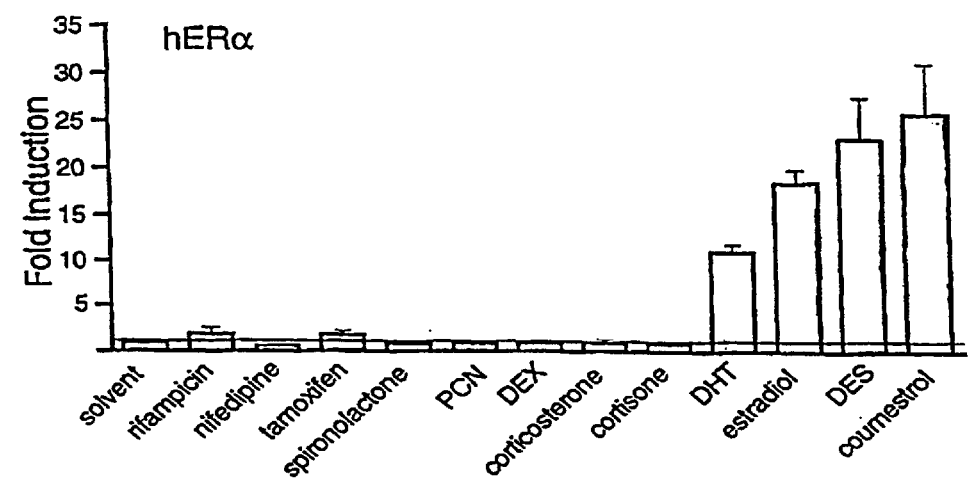

To demonstrate that the activation of SXR and PXR by high steroid concentrations is not a general property of all steroid receptors, parallel tests were conducted to determine the activation of the human estrogen receptor (ER) by the same panel of compounds. The only endogenous steroids tested that activated the ER were DHT and estradiol. The synthetic ER agonist, DES, and the phytoestrogens, including coumestrol (FIG. 7C), also activated the human estrogen receptor.

Figure 6C:
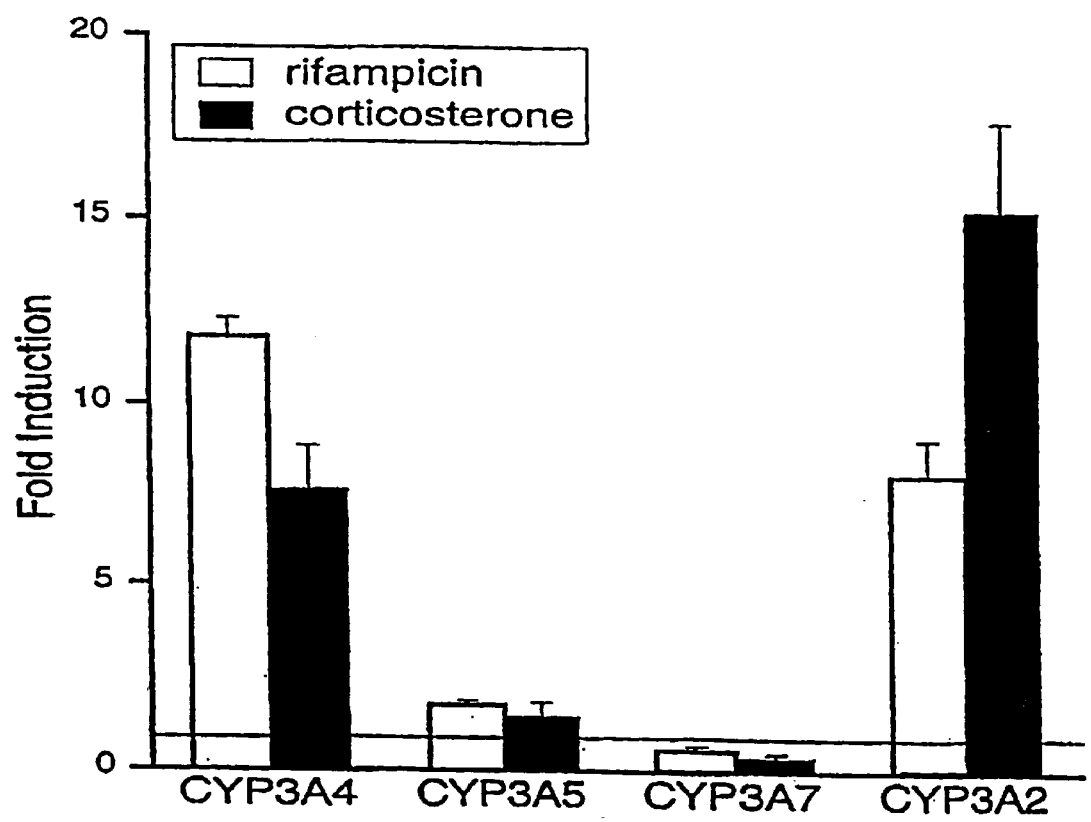
Figure 7D:
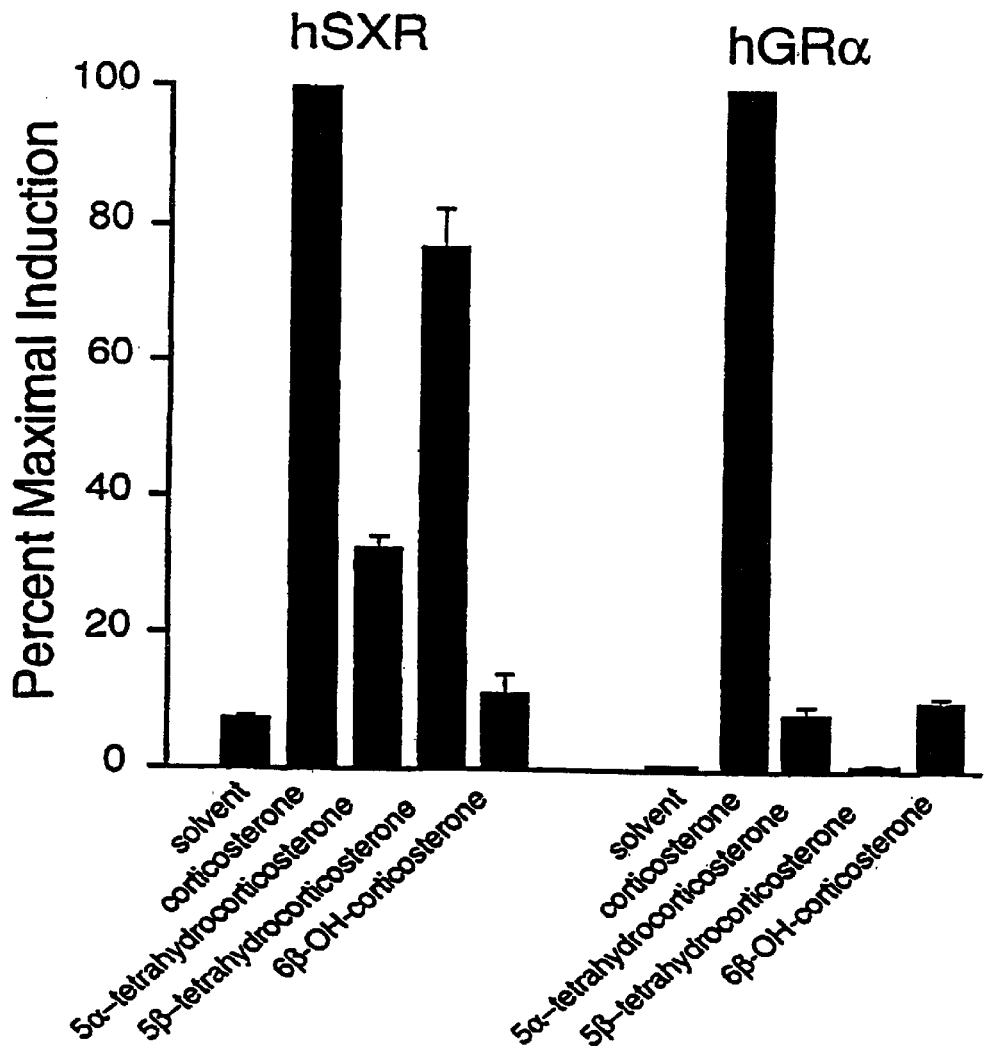
FIG. 7D is a bar graph illustrating that reduction of the 4-5 double bond in corticosterone does not inactivate the compound as an agonist of hSXR. 6β-hydroxylated, non-reduced, 5α and 5β reduced forms of corticosterone were tested for their ability to activate GAL-hSXR on tk(MH100)$_4$-luc (lefthand group of 5 columns) and hGRα on MTV-luc at 50 μM (righthand group of 5 columns). Similar results were obtained using full-length SXR. In each group of columns: column 1=solvent; column 2=corticosterone; column 3=5α-tetrahydrocorticosterone; column 4=5β-tetrahydrocorticosterone; and column 5=6β-OH-corticosterone.

Because the invention SXR-responsive elements are localized in genes encoding steroid hydroxylases, products of steroid catabolism, such as reduced or hydroxylated corticosterone derivatives, were tested for activation of SXR. The results of these tests shown in FIG. 7D illustrate that both 5α and 5β reduced forms of corticosterone are effective SXR activators; however 5α is slightly active, and 5β is completely inactive on GR. While a few 5α-reduced steroids remain active (e.g., dihydrotestosterone), 5β-reduced steroids fail to activate classical steroid receptors (Russell and Wilson, *Ann. Rev. Biochem.* 63:25–61. 1994). Therefore, the activation of SXR by 5β-reduced steroids may reflect a previously undetected regulatory pathway for these compounds. In addition, the virtual inactivity of, 6β-hydroxy corticosterone on SXR (FIG. 6D), suggests that CYP3A4 catalyzed hydroxylation is a potential definitive regulatory step in steroid metabolism.

These results indicate that the induction of some xenobiotic-metabolizing enzymes by pharmacological levels of steroids, drugs, and xenobiotic compounds is regulated by a broad-specificity sensor, rather than numerous specific receptors. SXR is a novel member of the nuclear receptor superfamily that is activated by a diverse group of steroids and their metabolites. Direct regulation by a broad-specificity sensor, such as the invention SXR, is biologically economical since much of the detpxofication and catabolism of such compounds is mediated by cytochrome P450 enzymes, particularly members of the CYP3A family, which both metabolize, and are induced by, a wide spectrum of diverse compounds, including steroids.

Based on the above-described studies, a number of relationships have been discovered among target genes, the SXR, and its activators that support the role of the SXR as a broad sensitivity sensor responsible for regulating cumulative levels of steroids and xenobiotics. First, SXR is expressed in tissues which catabolize steroids and xenobiotics, particularly in liver, the major expression site of steroid and xenobiotic metabolizing enzymes, and in the intestine. Although less is known about the role of gut tissue in steroid metabolism, the gut is known to play an important role in first pass metabolism of dietary, and orally-administered compounds (Holtbecker et al., *Drug Metab. Dispos.* 24:1121-1123, 1996; and Kolars et al., *Lancet* 338:1488-1490, 1991). For example, CYP3A4 is highly expressed in enterocytes (Kolars et al., *J. Clin. Invest.* 90:1871-1878, 1992). Thus, SXR is expressed at high levels in two key tissues for steroid and xenobiotic catabolism. Second, catabolic enzymes expressed in tissues that express SXR are induced by the invention SXR. SXR response elements have been discovered in the well-characterized CYP3A4 promoter as well as those of P450 oxidoreductase, CYP2A, CYP2C, CYP2E and glucuronosyl transferase, which are all known to be involved in steroid and xenobiotic catabolsim (F.J. Gonzalez, *Trends Pharmacol. Sci.* 13:346-352, 1992). Third, compounds known to induce catabolic enzymes activate the invention SXR, including drugs (such as rifampicin and nifedipine), steroid receptor agonists and antagonists (such as estrogen and tamoxifen); bioactive dietary compounds (such as phytoestrogens), and the like. In particular, CYP3A4 is known to be inducible (Rendic and Di Carlo, 1997) by virtually all the compounds applicants have identified as SXR activators. Lastly, products of early catabolic steps, such as reduced steroids, activate SXR, ensuring their complete inactivation and elimination. Taken together, these relationships support the role of the SXR as a broad-specificity sensor operative to regulate homeostasis of steroids and xenobiotics.

Activation of SXR also provides a molecular explanation for the paradoxical induction of the CYP3A genes (a.k.a. $P450_{PCN}$) by both glucocorticoid receptor agonists and antagonists and for the differential response of orthologous enzymes in different species. The inducible CYP3 A genes harbor a response element in their promoters that has been shown to be responsible for PCN and glucocorticoid induction (Barwick, supra, 1996; Burger, supra, 1992; Gonzalez, supra, 1986; Schuetz and Guzelian, supra, 1984; and Kliewer, supra, 1998). Applicants have discovered that these response elements can be activated by the invention SXR (FIGS. 6A and 6C). Despite their common role in steroid and xenobiotic catabolism, CYP3A genes from different species, and particularly the glucocorticoid-responsive promoter elements, show considerable differences in the pharmacology of their inducers (Barwick, supra, 1996). For example, PCN is a strong inducer of rat CYP3A2 and CYP3A3, but a weak inducer of human CY3A4 and rabbit CYP3A6. On the other hand, rifampicin is a strong inducer of the human and rabbit genes encoding such enzymes but not the rat genes (Barwick, supra, 1996).

However, when the response elements from such genes are tested by transient transfection into primary hepatocytes from rats or rabbits, the responsiveness changes to that of the host cell type. For example, glucocorticoid-responsive elements from the rat CYP3A2 and CYP3A3 promoters were induced by DEX in both rat and rabbit hepatocytes, by PCN only in rat hepatocytes, and by rifampicin only in rabbit hepatocytes (Barwick, supra, 1996). Similarly, the glucocorticoid-responsive element from the human CYP3A4 promoter was inducible by DEX in both rat and rabbit hepatocytes, by PCN only in rat hepatocytes, and by rifampicin only in rabbit hepatocytes (Barwick, supra, 1996). The activation profiles in rat cells correspond to the responsiveness of PXR to inducers (FIG. 6C); whereas the responsiveness in rabbit cells corresponds to that of SXR. Since the rabbit 3A6 promoter lacks the rodent DR-3 element, but has the human IR-6 element (Barwick, supra, 1996), it can be inferred that rabbit liver will likely have a receptor more closely related to SXR than to PXR. Thus, the pharmacology of SXR and PXR activation explains the different inducibility of the rat, rabbit, and human members of the cytochrome P4503A family. This discovery suggests that rabbit hepatocytes behave more like their human counterparts than do rodent hepatocytes, and that rabbits are perhaps better suited to testing for human-like drug interaction than rodents.

One additional member of the new branch of the nuclear receptor superfamily called the steroid and xenobiotic receptor has been discovered in mouse tissue. Screening of a mouse liver cDNA library at reduced stringency resulted in the identification of 39 cDNAs, all of which encoded PXR.1. Orthologous nuclear receptors typically share greater than 90% amino acid identity in the ligand binding domain when comparing rodent and human receptors (e.g., RARα—98% human/mouse (h/m), PPARγ—98% h/m, STGTR—95% h/m, TRβ—98% h/rat, ERα—89% h/m). Therefore, PXR and SXR may represent α and β subtypes of the steroid and xenobiotic nuclear receptor family. This conclusion is supported by the distinct pharmacological properties of the receptors, as illustrated in the Examples herein. Further screening of mouse and human liver cDNA libraries has failed to identify other family members. It is also possible that PXR and SXR represent unusually divergent orthologous genes. If this were correct, the divergence might reflect adaptation of the receptor to the difference between the diets of rodents and primates and the requirement for the receptor to respond to appropriate food-borne compounds.

To obtain the invention receptor, commercially obtained Northern blots of multiple human tissues were probed by full-length SXR cDNA (SEQ ID NO: 1), as described in Example 1 herein. The results showed that SXR mRNA is expressed at high levels in human liver and at more moderate levels in human intestine. Exposures of the Northern blots for longer than 24 hours did not reveal expression in any other tissues. Multiple mRNAs were detected, ranging from 3500 nt to larger than 9000 nt. Comparison of the sequences of the four cDNAs obtained reveals shared protein coding and 5' untranslated sequences, but a different 3' end for each of the four. These sequence differences may be due to alternative polyadenylation.

Electrophoretic mobility shift assays were employed to determine the ability of SXR to heterodimerize with RXR and to analyze the selectivity and specificity of SXR DNA binding as described in Example 4 herein. Receptors that heterodimerize with RXR typically bind to direct repeats of AGGTCA or closely related sequences (Mangelsdorf and Evans, supra, 1995). SXR alone and in combination with RXR was tested against a series of response elements differing in the spacing between half sites from 0 to 15 nucleotides. No binding was seen on classic steroid response elements. In contrast, strong binding was selective to a DR—4 motif with minimal binding to DR—3 and DR—5, and no binding to other spacings. When the variant AGTTCA (βDR) half site was used, strong binding was seen on βDR—4 and βDR—5, and significant, but reduced, binding to βDR—3. These results demonstrate that SXR binds DNA as a heterodimer with RXR rather than as a homodimer like the classical steroid receptors (Beato, supra, 1995).

To determine whether the activity of SXR was ligand-dependent, mixtures of natural and synthetic compounds were tested for their ability to activate SXR in transfection-based assays. A mixture containig DHEA and pregnenolone was active, suggesting that SXR might be a new steroid receptor. To characterize more fully the response properties of the receptors, a large variety of steroids, including intermediate metabolites and major products of known steroid biosynthetic pathways were tested for ability to activate the invention SXR. As illustrated by the results shown in FIG. 2, most of these compounds were active, although there were clear differences in potency. Of the more than 70 steroids tested, most showed some activity at high doses. It was also discovered that both full-length receptors and GAL4-receptor ligand binding domain chimeras showed similar activity; but no activation of reporter gene expression was detected in experiments with reporter alone or reporter plus GAL4 DNA-binding domain (FIG. 2). These results indicate that activation is dependent on the ligand-binding domain of SXR.

The most potent and efficacious activator of the numerous steroids tested was corticosterone (FIG. 2). Estradiol and dihydrotestosterone were also remarkably effective activators, while aldosterone and 1,25 dihydroxy vitamin D3 were inactive, even at a concentration of 50 μM (FIG. 2). Although ligands for the classical steroid receptors do show some overlap in receptor specificity, there is no known example of a nuclear receptor that can be activated by so many different types of steroids. This broad ligand specificity of the invention SXR parallels that of PPARα, which is activated by a very diverse group of dietary fatty acids at micromolar levels (Forman et al., *Proc. Natl. Acad. Sci. USA* 94:4312-4317, 1997; Gottlicher et al., *Proc. Natl. Acad. Sci. USA* 89:4653-4657, 1992; Kliewer et al., *Proc. Natl. Acad. Sci.* (*USA*) 94:4318-4323, 1997).

A search of the GENBANK database for genes containing potenial SXR response elements identified the steroid hydroxylases CYP2A1, CYP2A2, CYP2C1, CYP2C6, CYP3A1, CYP3A2, P450 oxidoreductase, and UDP-glucuronosyl-transferase as candidate target genes (FIG. 6A). The search identified DR—3, DR—4 and DR—5 elements present in these genes, which indicates that such compounds activate the invention SXR. Similarly, the transfection-based assays described in Example 4, which were conducted to test the ability of steroids and xenobiotics to activate SXR response elements showed that corticosterone along with pregnenolone, progesterone, dihydrotestosterone (DHT), estradiol, and PCN are consistently among the best activators. Dexamethasone, cortisone, and DHEA are in the group of intermediate activators, and there is little response from either aldosterone or cortisol (FIG. 4). Consistent with the DNA-binding data, maximal activities induced by these activators was achieved in steroid inducible P450 genes containing βDR—3, βDR—4, and βDR—5 response elements (FIG. 4).

The term "effective amount" as applied to a SXR polypeptide agonist or antagonist according to the invention means the quantity necessary to modulate metabolism of one or more steroid and/or xenobiotic compounds to a desired level, for example, a level effective to treat, cure, or alleviate the symptoms of a disease state for which the therapeutic compound is being administered, or to establish homeostasis. Alternatively, when an agonist according to the invention is employed to prevent steroid toxicity in a subject therapeutically administered one or more therapeutic steroid and/or xenobiotic compounds in treatment of a disease state, the term "effective amount" is an amount necessary to bring the overall level of steroids and xenobiotic compounds to a safe level, for example as determined by blood tests of the individual being treated for the effects of steroid toxicity, or to alleviate the symptoms of steroid toxicity as determined by the physician. Similarly, the amount of a SXR polypeptide antagonist according to the invention used to slow clearance of a therapeutic steroid or xenobiotic compound is an amount necessary to raise the blood level of the particular therapeutic compound to a therapeutic level and hence treat or alleviate the symptoms of the disease state for which the therapeutic steroid or xenobiotic compound is being administered. Since individual subjects may present a wide variation in severity of symptoms and each drug or active agent has its unique therapeutic characteristics, the precise mode of administration, dosage employed and treatment protocol for each subject is left to the discretion of the practitioner.

Amounts effective for the particular therapeutic goal sought will, of course, depend on the severity of the condition being treated, and the weight and general state of the subject. Various general considerations taken into account in determining the "effective amount" are known to those of skill in the art and are described, e.g., in Gilman et al., eds., *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990, each of which is herein incorporated by reference.

Pharmaceutical formulations of the SXR polypeptide agonists or antagonists of the present invention can be used in the form of a solid, a solution, an emulsion, a dispersion, a micelle, a liposome, and the like, wherein the resulting formulation contains one or more of the agonists or antagonists contemplated for use in the practice of the present invention, as active ingredients, in admixture with an organic or inorganic carrier or excipient suitable for enteral or parenteral applications. The active ingredients may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compounds (i.e., one or more SXR polypeptide agonist or antagonist) are included in the pharmaceutical formulation in an amount sufficient to produce the desired effect upon the target process, condition or disease.

Pharmaceutical formulations containing the active ingredients contemplated herein may be in a form suitable for oral use, for example, as tablets, troches, lozenges, aqueous or oily suspensions, dispersible powders or granules, emulsions, hard or soft capsules, or syrups or elixirs. Formulations intended for oral use may be prepared according to any method known in the art for the manufacture of pharmaceutical formulations. In addition, such formulations may contain one or more agents selected from a sweetening agent (such as sucrose, lactose, or saccharin), flavoring agents (such as peppermint, oil of wintergreen or cherry), coloring agents and preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents such as calcium carbonate, lactose, calcium phosphate, sodium phosphate, and the like; (2) granulating and disintegrating agents such as corn starch, potato starch, alginic acid, and the like; (3) binding agents such as gum tragacanth, corn starch, gelatin, acacia, and the like; and (4) lubricating agents such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredients are mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, or olive oil.

The pharmaceutical formulations may also be in the form of a sterile injectable solution or suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,4-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, or synthetic fatty vehicles, like ethyl oleate, or the like. Buffers, preservatives, antioxidants, and the like can be incorporated as required.

Formulations contemplated for use in the practice of the present invention may also be administered in the form of suppositories for rectal administration of the active ingredients. These formulations may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

In accordance with yet another aspect of the invention, there are provided animal models which are useful to study human response to agents for possible up-regulation of CYP3A. Invention animal models include transgenic non-human animals (e.g. rodents and the like) transformed with nucleic acid encoding human SXR. Those of skill in the art can readily determine suitable methods for introducing nucleic acid encoding human SXR into a suitable host. In another embodiment of the invention, transgenic animal models are provided wherein SXR and homologs thereof (e.g., PXR) have been "knocked out" so as to render the animal model substantially free of any background activity contributed by SXR or homologs thereof. The resulting transgenic animals are referred to herein as "knock-out" animals, based on the protocol whereby sequence encoding SXR or homologs thereof is deleted from the genome or such sequence in sufficiently disrupted or inactivated so as to preclude expression of active receptor by the host organism. Those of skill in the art can readily identify numerous methods whereby deletion or inactivation of target sequence (e.g., SXR or homologs thereof) can be accomplished.

Recent important advances have been made in the understanding of the mechanism through which foreign chemicals impact on the P450-dependent metabolic processes. One key discovery is the establishment of potential roles for orphan receptor SXR in mediating the induction of CYP3A family of P450's in response to a variety of xenochemicals including certain drugs and steroids. Electrophoretic mobility shift assays reveal that SXR/RXR heterodimer can bind the IR—6 and DR—3 response elements derived from the promoters of human CYP3A4 genes. Moreover, SXR activates the response element-containing synthetic reporter genes in response to some drug/xenochemicals and steroid hormones, suggesting a potential role of SXR in CYP3A induction. In accordance with the present invention, it is demonstrated that SXR can activate CYP3A cellular promoters in primary rat hepatocyte cultures. Furthermore, introducing the human SXR to produce a transgenic mouse is sufficient to render the mouse liver with a human profile of CYP3A gene inducibility, and expression of an activated form of SXR results in specific and constitutive upregulation of CYP3A, establishing a central role of SXR/PXR in CYP3A gene induction.

In addition to SXR and the mouse homolog, PXR, nuclear receptors CAR, PPARα, FXR and LXRα, have also recently been implicated in the regulation of other CYP family members (for a review, see Waxman 1999). Moreover, endogenous ligands of each of these nuclear receptors have been identified and physiological receptor functions are emerging, leading to the proposal that these receptors may primarily serve to modulate hepatic P450 activity in response to endogenous dietary or hormonal stimuli.

Although there are substantial structural and catalytic similarities among the various members of the CYP3A family across species lines, there are important differences in regulatory control of these genes (for reviews, see Gonzalez, 1990, and Nelson, 1999). For example, a clear discrepancy between human and rodents is that RIF induces CYP3A4 in human liver (Watkins et al., 1985) but does not induce its homologues CYP3A23 in rat (Wrighton et al., 1985) and CYP3A11 in mouse (Schuetz et al., 1996), respectively. Rifampicin does induce CYP3A6, the homologous form in rabbit (Kocarek et al., 1995), yet in the rabbit, PCN, which induces CYP3A23 in rat liver (Wrighton et al., 1985), does not induce CYP3A6. PCN is also a poor activator for CYP3A4 (Schuetz et al., 1993, Kocarek et al., 1995, Blumberg et al. 1998, and Lehmann et al., 1998).

Based on two pieces of evidence, it is proposed that SXR/PXR, rather than the gene structure, determine the inducibility of CYP3A genes: (1) SXR and PXR share similar DNA binding profiles. Steroid and xenobiotic inducibility of human CYP3A4 has been localized to an IR-6 containing 19-bp element (Barwick et al. 1996), and a similar element is also present in the rabbit CYP3A6 genes (Barwick et al. 1996); whereas the promoters of rodent CYP3A genes contain DR-3 elements. Electrophoretic mobility shift assays reveal that both SXR:RXR and PXR:RXR heterodimers bind to DR-3 and IR-6 elements efficiently (Blumberg et al., 1998, and Lehmann et al., 1998); (2) When cultured rat hepatocytes were transfected with vectors bearing DR-3 or IR-6-containing 5'-flanking response DNA element from CYP3A23, CYP3A4, or CYP3A6 genes, reporter gene activity was induced on treatment with PCN; whereas RIF treatment had no effect. When the same vectors were transfected into rabbit hepatocytes, increased activity was observed on treatment of the cells with RIF but not with PCN (Barwick et al. 1996). However, such trans-species gene transfer has not been tested in the context of the cellular promoters of the CYP genes.

In accordance with the present invention, it is demonstrated that SXR dictates the inducibility of CYP3A in hepatocyte cultures and in transgenic mice, and the DR-3 and IR-6 response elements are interchangeable in the context of rat CYP3A23 cellular promoter. These results provide strong evidence that the host cellular environment, SXR/PXR herein, rather than the structure of the gene dictates the pattern of CYP3A inducibility. Furthermore, a system of trans-species gene transfer and CYP3A inducibility has been established, which could, in turn, provide a unique technique for identifying mechanisms of induction and advancing the development of appropriate toxicological models for human safety assessment.

Thiazolidinediones (TZDs) are a new class of oral antidiabetic agents. They selectively enhance or partially mimic certain actions of insulin, causing a slowly generated antihyperglycaemic effect in Type II (noninsulin dependent) diabetic patients. To date two TZDs, first troglitazone (Rezulin) and more recently Rosiglitazone (BRL49653), have been introduced into clinical use. However, hepatotoxicity, which was anecdotally reported as a problem with ciglitazone and englitazone, has proved to be the main clinical concern with troglitazone (for a review, see Day, 1999). In clinical trials, troglitazone-induced hepatotoxicity (alanine aminotransferase level>three times the upper limit of normal) was identified in 1.9% of 2510 patients; these abnormalities resolved with discontinuation of therapy with the drug (for a review, see Watkins and Whitcomb, 1998). Indeed, hepatic dysfunction and/or fulminant leading to hepatic failure has been reported in patients receiving troglitazone (Neuschwander-Tetri et al, 1998, Shibuya et al. 1998, and for reviews, see Watkins and Whitcomb, 1998, and Day, 1999). However, the mechanism of the liver toxicity of TZDs remains largely unknown.

In accordance with the present invention, it has been shown that members of the TZDs selectively activate SXR both in hepatocyte cultures and in transgenic animals. Among the tested TZDs, BRL has the highest binding affinity to PPARγ with a Kd of approximately 40 nM (Lehmann et al., 1995), yet fail to activate SXR; whereas troglitazone and ciglitazone activate SXR. The activation of SXR and subsequent upregulation of CYP3A gene by troglitazone and ciglitazone, together with the fact that constitutive activation of SXR causes liver toxicity, provides a potential mechanism for the known clinical liver toxicity by certain TZDs. However, it remains to be seen whether BRL clinically exhibits reduced or an absence of liver toxicity. Although the VPSXR-induced liver toxicity does not completely mimic troglitazone-induced human liver disease in histologic appearance, it is possible that the acute hepatocellular injury present in transgenic mice is a precursor lesion to be confluent necrosis observed in patients with troglitazone injury. The results presented herein also raise the notion that activation of SXR and/or upregulation of CYP3A gene may be applied to screen future TZD drugs and other pharmaceutical compounds. The Alb-SXR transgenic mice, as well as the hepatocyte transfection system, will be invaluable tools in such applications.

The factors responsible for human variation in CYP3A expression are under intense investigation. This variation is believed to influence drug response for up to one-third of all drugs and may also contribute to inter-individual differences in health effects resulting from exposure to CYP3A-metabolized carcinogens in the environment (Kolars et al., 1994). The extent to which drugs, like RIF, can up-regulate CYP3A is of therapeutic importance because it is coadministered with so many drugs that are CYP3A substrates and thus contributes to increased or decreased effectiveness of these drug therapies as well as adverse side effects (Borcherding et al., 1992, and Hebert et al., 1992). However, RIF does not induce CYP3A23 in rat (Wrighton et al., 1985) and CYP3A11 in mouse (Schuetz et al., 1996), respectively, which in turn limits the application of rodent models in studying RIF-mediated CYP induction.

In accordance with the present invention, Alb-SXR transgenic mice have been successfully generated which are readily responsive to RIF to induce CYP3A gene. The doses of RIF (1-10 mg/kg) that induce CYP3A in these mice are in the range of the standard oral dosing regimen in humans (300-600 mg per 70-kg man). Moreover, the dynamics and the reversibility of RIF-mediated CYP3A induction in the Alb-SXR mice are in agreement with the observation in humans (Kolars et al., 1992), indicating the Alb-SXR mice are indeed an excellent rodent model to study RIF-induced CYP3A response.

The invention will now be described in greater detail by reference to the following non-limiting examples.

EXAMPLE 1 cDNA Identification

SXR was identified from a human genomic library (Clontech) hybridized with a full-length cDNA encoding Xenopus BXR (Blumberg et al., 1998a) under reduced stringency conditions (hybridization in 0.5 M NaPO$_4$ pH 7.0, 7% sodium dodecyl sulfate (SDS), 5% dextran sulfate at 65° C. overnight, washing three times twenty minutes in 2 x standard saline citrate solution (0.15M saline containing 0.015M sodium citrate, pH 7)(SSC), 0.1% SDS at 37° C.). Restriction mapping and Southern blot analysis showed that three exons were contained within the 9 kb EcoRI hybridizing fragment. This fragment was used to probe a Northern blot of multiple types of human tissue (Clontech) at high stringency (hybridization as above, washing twice for 20 minutes in 0.1x SSC, 0.1% SDS at 50° C.) and hybridization was detected in liver. A human liver cDNA library (Stratagene, La Jolla, Ca) was subsequently screened using the same conditions, and four independent clones were identified. Each of these clones was sequenced on both strands within the protein coding region. DNA sequences were compiled and aligned using the programs of Staden (R. Staden, *Nucl. Acids Res.* 14:217–231, 1986), University of Wisconsin Genetics Computer Group (Devereaux et al., *Nucl. Acids Res.* 12:387–395, 1984). Database searching was performed using the BLAST network server at the National Center for Biotechnology Information (Altschul et al., *J. Mol. Biol.* 215:403–410, 1990). PXR was isolated from a mouse liver cDNA library (Stratagene) by screening with the SXR protein coding region at reduced stringency (5xSSC, 43% formamide, 5x Denhardts, 0.1% SDS, 0.1 mg/ml denatured, sonicated salmon sperm DNA at 37° C.). Three, twenty minute washes were performed in 0.5 x SSC, 0.1% SDS at 50° C. .

EXAMPLE 2

Ability of SXR to Heterodimerize with RXR

The protein coding region of SXR was PCR amplified and subcloned into NcoI and BamHI sites of the vector pCDG1 (Blumberg, supra, 1998α) using ExoIII-mediated ligation independent cloning (Li and Evans, *Nucl. Acids Res.* 25, 4165–4166, 1997). During this process the putative initiator Leu was converted to Met with a Kozak consensus sequence CC<u>ATG</u>G. The actual response elements and the number of copies are as follows: the base vector is tk—luc in all cases (Hollenberg et al., *Nature* 318:635–641, 1985):

DR-1, tk(ApoAI)$_4$ (Ladies and Karathanasis, *Science* 251:561–565, 1991);
DR-2, tk(Hox-B1-RARE)$_2$ (Ogura and Evans, *Proc. Natl. Acad. Sci.* (USA) 92:387–391, 1995);
βDR-3, tk(CYP3A2)$_3$ (Kliewer et al., *Cell* 92:73–82, 1998),
DR-4, tk(MLV-TRE)$_2$ (Umesono et al., *Cell* 65:1255–1266, 1991);
βDR-4, tk(LXRE)$_3$ (Willey et al., *Genes Dev.*9:1033–1045, 1995);
βDR-5, tk(βRARE)$_3$ (Sucov et al., *Natl. Acad. Sci.* (U.S.A.) 87:5392–5396, 1990);
TRE$_p$, tk(TRE$_p$)$_2$ (Umesono et al., supra, 1991).
Direct repeat 0–15 (DR-0 up to DR-15) oligonucleotides employed herein had the following sequences:
DR-0: catagtc AGGTCA AGGTCA gatcaac (SEQ ID NO:12);
DR-1: catagtc AGGTCA t AGGTCA gatcaac (SEQ ID NO:13);
DR-2: catagtc AGGTCA at AGGTCA gatcaac (SEQ ID NO:14);
DR-3: catagtc AGGTCA tat AGGTCA gatcaac (SEQ ID NO:15);
DR-4: catagtc AGGTCA tata AGGTCA gatcaac (SEQ ID NO:16);
DR-5: catagtc AGGTCA tatat AGGTCA gatcaac (SEQ ID NO:17);
DR-6: catagtc AGGTCA tatata AGGTCA agatcaac (SEQ ID NO:18);
DR-7: catagtc AGGTCA tatatat AGGTCA gatcaac (SEQ ID NO:19);
DR-10: catagtc AGGTCA tatatatata AGGTCA gatcaac (SEQ ID NO:20);
DR-15: catagtc AGGTCA tagtagtagtagtag AGGTCA gatcaac (SEQ ID NO:21). GAL4-SXR was constructed by subcloning aa 107–434 of SEQ ID NO:2 into pCMX-GAL4 (Perlmann, supra, 1993).

Similarly, the PXR·1 protein coding region was PCR amplified and subcloned into a NcoI-BamHI cut in pCDG1, while amino acids 104 to 431 were subcloned into CMX-GAL4. Reporter plasmids were constructed by synthesizing three-copy response elements and subcloning into a HindIII-BamHI cut in pTk-luc (Hollenberg et al., *Cell* 49:39–46, 1987).

CV-1 cells were maintained in Dulbecco's Modified Eagle's Medicine (DMEM) containing 10% resin-charcoal stripped calf bovine serum (CBS). Liposome-mediated transient transfections were performed using 1,2-bis (oleoyloxy)-3-(trimethylammonio) propane (DOTAP) reagent (Boehringer Manheim) at a concentration of 5 μg/ml in DMEM containing 10% resin charcoal stripped fetal bovine serum in 96-well format using a Beckman Biomek 1000 laboratory workstation as described in (Blumberg et al., *Proc. Natl. Acad. Sci* (USA) 93:4873–4878, 1996). Test ligands were added the next day in DMEM containing 10% delipidated fetal bovine serum (FBS). After 18–24 hours incubation, the cells were lysed and luciferase reporter gene assays and β-galactosidase transfection control assays were performed as described in (Blumberg, supra, 1996). Reporter gene expression was normalized to the β-galactosidase transfection control and expressed as relative light units per optical density unit per minute of β-galactosidase activity, or fold induction over solvent control. Each data point represents the average of triplicate experiment +/− standard error and was replicated in independent experiments.

EXAMPLE 3

Cell Culture and Transfection Studies

To determine whether the activity of SXR was ligand-dependent, mixtures of natural and synthetic compounds were tested for their ability to activate SXR in transfection-based assays. Thus, the protein coding region of SXR was PCR amplified and subcloned into NcoI and BamH1 sites of the vector pCDG1 (see Blumberg et al., supra). During this process the putative initiator Leu was converted to Met with a Kozak consensus sequence CC<u>ATG</u>G.

GAL4-SXR was constructed by cloning amino acid residues 134–446 of SXR into pCMX-GAL4 (see Perlman et al. supra). CV-1 cells were maintained in DMEM containing 10% resin-charcoal stripped calf bovine serum. Liposome-mediated transient transfections were performed using DOTAP reagent (Boehringer Manheim) at a concentration of 5 mg/ml in DMEM containing 10% resin charcoal stripped fetal bovine serum in 96-well format using a Beckman Biomek 1000 laboratory workstation as previously described by Blumberg et al., in *Proc. Natl. Sci.* (USA) 93:4873 (1996)).

Ligands were added the next day in DMEM containing 10% delipidated FBS. After 18–24 hours incubation, the cells were lysed and luciferase reporter gene assays and b-glactosidase transfection control assays performed as previously described by Blumberg et al. (1996), supra. Reporter gene expression was normalized to the b-galactosidase transfection control and expressed as relative light units per O.D. per minute of b-galactosidase activity or fold induction over solvent control. Each data point (see FIG. 2) represents the average of triplicate experiments +/− standard error and was replicated in independent experiments.

EXAMPLE 4

DNA-Binding analysis

Electrophoretic mobility shift assays were performed using in vitro transcribed, translated proteins (TNT, Promega). Proteins (1 μl each) were incubated for 20 minutes at room temperature with 100,000 cpm of Klenow-labeled probes in 10 mM Tris pH 8, 100 mM KCl, 6% glycerol, 0.05% NP-40, 1 mM dithiothreitol (DTT), 100 ng/μl poly dI:dC (Pharmacia, Piscataway, N.J.) and then electrophoresed through a 5% polyacrylamide gel in 0.5x TBE (45mM Tris-base, 45 mM boric acid, 1 mM ethylenediaminetetraacetic acid (EDTA) at room temperature. For competition binding, protein plus unlabeled oligonucleotides at five or fifty fold molar excess were preincubated for ten minutes on ice, then labeled probes were added and incubated for 20 minutes at room temperature. Electrophoresis was as above. The IR series oligonucleotides tested had the following sequences:
IR-0, agcttAGGTCATGACCTa (SEQ ID NO:25);
IR-1, agcttAGGTCAgTGACCTa (SEQ ID NO:26);
IR-2, agcttAGGTCAcgTGACCTa (SEQ ID NO:27);
IR-3, agcttAGGTCAcagTGACCTa, (SEQ ID NO:28
IR-4, agcttAGGTCAcatgTGACCTa (SEQ ID NO:29);
IR-5, agcttAGGTCAcactgTGACCTa (SEQ ID NO:30);
IR-6, agcttTGAACTcaaaggAGGTCA) (SEQ ID NO:31); and
IR-M, agcttACGTCATGACGTa (SEQ ID NO:32).

Mutations in the IR-M nucleotide sequence prevented binding of the heterodimer to the response element.

CYP3A oligonucleotides tested had the following sequences:
CYP3A4, tagaataTGAACTcaaaggAGGTCAgtgagtgg (SEQ ID NO: 33);
CYP3A5, tagaataTGAACTcaaaggAGGTAAgcaaaggg (SEQ ID NO: 34); and
CYP3A7, tagaataTTAACTcaatggAGGCAgtgagtgg (SEQ ID NO: 35).

EXAMPLE 5

Plasmid Constructs and Mutagenesis

The CYP3A23 cellular promoter reporter, PGL3-CYP3A23, was cloned by inserting the PCR-amplified 5' regulatory sequence of rat CYP3A23 gene (nt-1360 to 82) (Burger, et al. 1992) into the PGL3 vector (Promega). PGL3-CYP3A4 contains up to nt—1093 of the 5' flanking regions of the human CYP3A4 gene (Hashimoto et al., 1993). Site-directed mutagenesis was performed by the PCR overextension method (Ho et al., 1989). The PCR-amplified sequences and target mutagenesis were confirmed by DNA sequencing.

The expression vectors for the wild type SXR (pCDG-HX7), an activated form of SXR (pVPG-HX7), and the wild type PXR (pCDG-PXR) were described previously (Blumberg et al, 1998).

EXAMPLE 6

Preparation of Hepatocytes, DNA Transfections and Drug Treatment

Primary cultures of rat hepatocytes were prepared as described previously (Li et al, 1991, and Barwick, et al. 1996). Lipofectin (Gibco-BRL)-mediated DNA transfections were carried out as described (Barwick, et al. 1996). When necessary, cell were treated with RIF, DEX, PCN, nifedipine, CTZ, corticosterone, coumestrol, RU486, cortisol, 17β-estrodiol (E2), pregnenolone, progesterone, cortisone (10μM each), phenobarbital, 3-methylcholanthrene (3MC) (2 mM each), or the control solvent. All compounds were purchased from Sigma.

EXAMPLE 7

Figure 8:
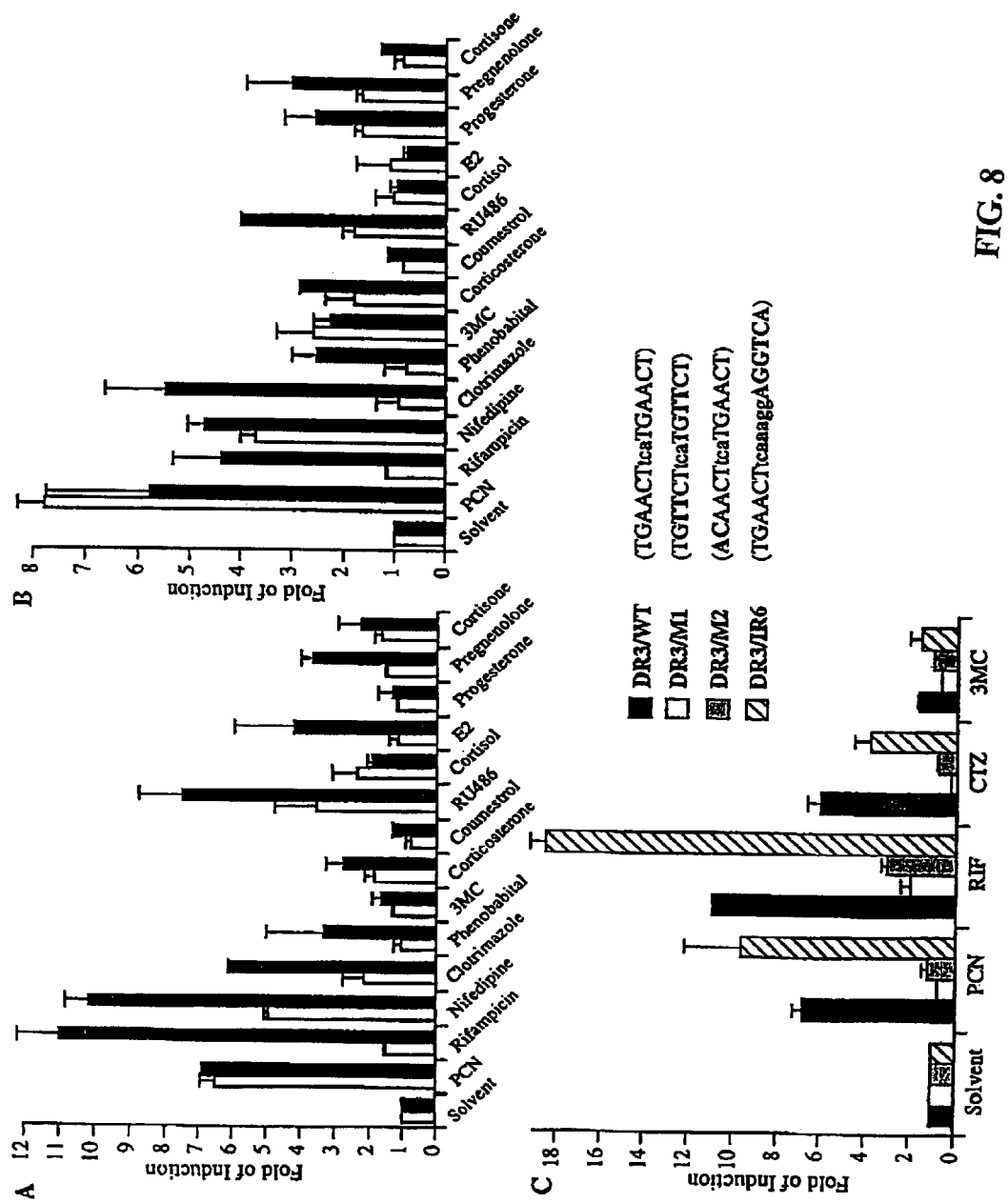
FIG. 8 collectively demonstrates that SXR renders the trans-species drug response of CYP3A genes in cultured hepatocytes.
Figure 9:
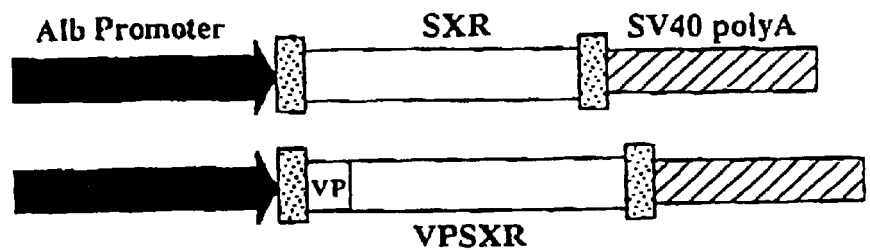
FIG. 9 presents schematic representations of the Alb-SXR and Alb-VPSXR transgene constructs. The filled region, stippled region, open region, and the crosshatched region, correspond to the mouse albumin promoter/enhancer, the xenopus β-globin leader and trailer sequences, the cDNAs of the wild type (SXR) or an activated form of SXR (VPSXR, with the fusion of VP16 activation domain at the 5'end as depicted), and the SV40 sequence containing the poly (A) processing signal, respectively.

SXR Imparts Trans-species Drug Response of CYP3A Genes to Rat Hepatocyte Cultures A panel of natural and synthesis steroid and nonsteroid compounds were tested for their ability to activate SXR and/or PXR in transfection-based assays using primary rat hepatocytes as recipient cells and the cellular promoters of the rat CYP3A23 gene or the human CYP3A4 gene as reporters. In the absence of SXR, the most potent and efficacious tested activators for CYP3A23 were pregnenolone-16-carbonitrile (PCN), nifedipine, RU486 (another antiglucocorticoid), whereas rifampicin (RIF), clotrimazole (CTZ), phenobarbital, 3-methylcholanthrene (3MC, a known CYP1A2 activator), corticosterone, coumestrol, cortisol, E2, progesterone pregnenolone, and cortisone fail to activate or behave as poor activators (FIG. 8A). This profile of activation reflects the responsiveness of the endogenous PXR, a rodent homologue of SXR. The failure of RIF to induce rat CYP3A23 gene is consistent with previous observation (Wrighton et al., 1985, and Schuetz et al., 1996). With the co-transfection of SXR, significant induction of CYP3A23 was achieved by RIF, CTZ, phenobarbital, E2, and pregnenolone. The induction of CYP3A23 by nifedipine, and RU486 also increased significantly; while the activation of CYP3A23 by PCN remained unchanged in the presence of SXR (FIG. 8A). Therefore, transfection of SXR render the responsiveness of rat CYP3A gene by RIF, a known human specific CYP3A activator.

When the human CYP3A4 cellular promoter was used as the reporter, a similar response profile was observed, except that E2 did not induce CYP3A4, and nifedipine did not further potentiate CYP3A4 induction in the presence of SXR (FIG. 8B). Thus, the human CYP3A4 can be activated by the rodent-specific activator PCN when the promoter was introduced into the rodent cellular environment, presumably via the activation of the endogenous PXR; on the other hand, RIF can active the CYP3A4 in the rodent cellular environment with the introduction of human SXR. The SXR-mediated activation of CYP3A23 or CYP3A4 cellular promoter by RIF exhibited dose dependence of both receptor and ligand (data not shown).

The fact that SXR is necessary and sufficient to render the induction of both human CYP3A4 and rat CYP3A23 gene in rodent hepatocytes by RIF suggested that the host cellular environment, SXR/PXR herein, rather than the gene structure, dictates the patterns of inducibility of CYP3A genes. The above notion would predict: (1) The SXR/PXR response element is essential for the activation of CYP3A genes; and (2) The response elements of SXR and PXR are interchangeable. Therefore, mutagenesis analysis was performed on the promoter or the rat CYP3A23 gene to examine these predictions. In vitro electrophoretic mobility shift assays showed that both SXR:RXR and PXR:RXR heterodimers efficiently bind to the DR-3 elements (5'TGAACTtcsTGAACT3' (SEQ ID NO:39)) in the CYP3A23 promoter (Blumberg et al., 1998). As shown in FIG. 8C, mutation of both half sites (DR3/M1) or a single half site (DR3/M2) abolished the PXR and/or SXR-mediated activation by PCN, RIF, and CTZ; on the other hand, replacement of the wild type DR-3 element by an IR-6 element of the human CYP3A4 gene promoter (Blumberg et al., 1998, and Kliewer et al., 1998) successfully rescue the inducibility by PCN, RIF and CTZ.

Taken together, the transfection results demonstrate that nuclear receptors SXR/PXR are essential in determining patterns of CYP3A inducibility. In addition, these results establish successful development of a cell culture system allowing trans-species gene transfer and CYP3A inducibility.

EXAMPLE 8

Generation and Identification of Transgenic Mice

To generate Alb-SXR and Alb-VPSXR transgenes, the SXR and VPSXR cDNA were released from pCDG-HX7 and pVPG-HX7 (Blumberg, et al., 1998), and cloned into the Bam HI site downstream of the mouse albumin promoter/enhancer (Pinkert et al., 1987), respectively. A SV40 intron/poly (A) sequence (Xie et al., 1999) was subsequently placed downstream of SXR and VPSXR cDNAs. The 8.45 kb Alb-SXR, and 8.75 kb Alb-VPSXR transgenes were excised from the vector via Not I and Asp 718 digestion, and purified from agarose gel using QIAquick Gel Extraction Kit (QIAGEN). Microinjection of transgene into one-cell CB6F1 mouse zygotes was carried out at the Salk Institute Transgenic Animal Facility. All mice were handled in an accredited Institute facility in accordance with the institutional animal care policies.

Genomic DNA was isolated as described before (Xie et al., 1999). The polymerase chain reaction (PCR) was used to screen the transgene positive mice. Two oligonucleotides used to screen Alb-SXR mice are 5'-GAGCAATTCGCATTACTCTGAAGT-3' (SEQ ID NO: 36) (annealing to SXR cDNA), and 5'-GTCCTTGGGGTCTTCTACCTTTCTC-3' (SEQ ID NO: 37) (annealing to the SV 40 sequence downstream of the transgene in the transgene cassette). Another two oligonucleotides used to screen Alb-VPSXR are 5'-GACGATTTCCATCTGGACATGTTGG-3' (SEQ ID NO: 38) (annealing to VP16 sequence), and 5'-GTTTTCATCTGAGCGTCCATCAGCT-3' (SEQ ID NO: 40) (annealing to the SXR cDNA). PCR was carried out in a DNA thermal cycler (Perkin-Elmer/Cetus) using the following program: 94° C. for 1 min, 58° C. for 2 min, and 72° C. for 3 min and products were analyzed by electrophoresis on a 1% agarose gel. The transgene integration status was analyzed by Southern blot using transgene specific probes as described before (Xie et al., 1999).

EXAMPLE 9

Generation of Alb-SXR and Alb-VPSXR Transgenic Mice

Transgenic mice expressing wild-type or an activated form of SXR under the control of the liver-specific promoter/enhancer for the mouse albumin gene (Pinkert et al., 1987) were generated by injection of one-cell (CB6F1 mouse zygotes with the transgene diagramed in FIG. 2A. This promoter fragment has been shown to direct faithfully the expression of the transgene in the liver of transgenic mice (Pinkert et al., 1987). The activated form of SXR (VPSXR) was generated by fusing the VP16 activation domain of the herpes simplex virus to the amino-terminal of SXR. Transfection of VPSXR expression vector into rat hepatocytes resulted in constitutive upregulation of the CYP3A23 gene (data not shown). Transgene-positive founders were identified by PCR using a pair of transgene-specific oligonucleotides, and the integrity of both transgenes was confirmed by Southern blot analysis (data not shown). A total of two and seven gene-positive founders were obtained for Alb-SXR and Alb-VPSXR transgene, respectively.

The expression of transgenes was assessed by Northern blot analysis of RNA from the mouse livers using a transgene-specific probe. Thus, twenty microgram of liver total RNAs were subjected to Northern blot analysis. The membranes were hybridized with [$^{32}$P]-labeled 3 kb SXR-SV40 DNA fragment from the transgene. The filters were subsequently stripped and reprobed with PXR cDNA probe, and the glyceraldehyde-3-phosphate dehydrogenase (GAPDH) cDNA for the purpose of loading control. The transgene transcripts (2.6 kb and 2.9 kb for Alb-SXR and Alb-VPSXR transgene, respectively) were detected in the liver of Alb-SXR, and Alb-VPSXR transgenics, but not in a nontransgenic control animal. The expression of endogenous PXR remains unchanged in the transgenic mice.

Initial Northern blotting revealed that Alb-SXR line 2198, and Alb-VPSXR lines 2224 and 2218 had relatively high expression of the transgenes (data not shown), and were characterized further. The expression of Alb-SXR (2.6 kb) or Alb-VPSXR (2.9 kb) transgene was specifically detected in the livers of transgenic mice but not in their nontransgenic littermates. Furthermore, the expression of SXR transgenes did not alter the expression of endogenous PXR. No transgene expression was seen in the small intestine, brain and kidney, consistent with the tissue-specificity of the albumin promoter (Pinkert et al., 1987).

EXAMPLE 10

Drug Responsiveness of CYP3A in SXR Transgenic Mice

The animals were allowed free access to food and water at all times. RIF (1–10 mg/kg when necessary), BRL (20 mg/kg, a gift from Dr. Richard Hayman of Ligand Pharmaceutical), ciglitazone (150 mg/kg, Biomol), and troglitazone (150 mg/kg) were administered via gastric gavage. When necessary, mice were treated with a single intraperitoneal injection of DEX (50 mg/kg), PCN (40 mg/kg), or CTZ (50 mg/kg).

To examine the drug response of the endogenous liver CYP3A11 gene, animals were treated with single dose of compounds 24 h before sacrifice, and the CYP3A11 gene expression was evaluated by Northern blot analysis on liver total RNA. Total RNA was prepared from tissues using the TRIZOL Reagent (Gibco-BRL). RNA was separated on 1.25% agarose-6% formaldehyde gel and transferred to a Nytran membrane (Schleicher & Schuell). To detect specific transcripts, [$^{32}$P]-cDNA probes labeled by Random Primer Labeling Kit (Boringher) were hybridized to the membranes. The probe used to detect transgene contains both the SXR cDNA and the SV40 sequences. The PXR cDNA probe was as described previously (Blumberg, et al. 1998). The probes of CYP3A11 gene (nt 1065 to 1569) (Yanagimoto et al. 1992), CYP7A (nt 973 to 1453) (Jelinek et al., 1990), CYP1A2 (nt 1151 to 1565) (Kimura et al., 1984) were cloned by RT-PCR using mRNA from wild type mouse liver. The filters were subsequently stripped and rehybridized with a murine glyceraldehyde-3-phosphate dehydrogenase (GAPDH) cDNA probe for RNA loading normalization.

As observed by Northern blot analysis, RIF (5 mg/kg body weight) specifically induced the expression of CYP3A11 in transgenic mice but not in their wild type littermates. Alb-SXR transgenic mice or control nontransgenic animals were treated with a single dose of RIF (5 mg/kg, gastric gavage), CTZ or PCN (50 mg/kg and 40 mg/kg, respectively, intraperitoneal injection). Tissues were harvested 24 h later and subjected to Northern blot analysis. Membranes were probed with CYP3A11 cDNA probe, and were subsequently stripped and reprobed with GAPDH and transgene specific probes. The increased expression of CYP3A11 in transgenics in response to RIF is of particular note.

The inability of RIF to induce CYP3A11 in wild type mice at this dose is consistent with previous observations (Schuetz et al., 1996). In agreement with transfection results, CTZ caused a moderate level, and a higher level of CYP3A11 induction in wild type animals and Alb-SXR mice, respectively; PCN is an equally efficacious CYP3A11 inducer in both wild type and transgenic animals. The induction of CYP3A11 in Alb-SXR mice is ligand dependent, as no CYP3A11 induction was observed in the absence of an inducer, and the level of transgene expression remained unchanged upon CYP3A11 gene activation.

Dynamics and dose-response of RIF treatment was investigated in Alb-SXR transgenic mice. In the study of dynamics, mice were subjected to daily treatment of RIF for the indicated period of time, and tissues were harvested 24 h after the last treatment. In the study of dose-response, mice were treated with a single dose of indicated amounts of RIF 24 h before tissue harvest. The reduction of RIF-induced expression of CYP3A11 by five days of RIF withdrawal after an initial 7-day treatment is significant. The CYP3A11 induction of RIF is rapid, and a significant induction was achieved after 12 h of RIF administration, with a plateau achieved by 24 h in the continuous presence of RIF. No CYP3A11 induction was observed in nontransgenic mice even after 7 d of RIF administration. Moreover, the RIF-induced expression of CYP3A11 was reversible, significant reduction of CYP3A11 expression was seen by five days of RIF withdrawal after an initial 7-day treatment (lane 7). The RIF-mediated CYP3A11 induction is also dose-dependent, increased hepatic CYP3A11 mRNA was seen with as little as 1 mg/kg of RIF administration, and the induction was further enhanced with increasing does of RIF, plateauing around 3–5 mg/kg. The dynamics and the reversibility of CYP3A induction by RIF is in agreement with the observation in humans (Kolars et al., 1992).

The CYP3A11 gene is constitutively induced in the livers of Alb-VPSXR transgenic mice, and its expression was not further enhanced by RIF treatment. Of note, the upregulation of CYP gene is liver- and CYP3A11-specific; as (1) the expression of CYP3A11 in the small intestine remains unchanged, (2) the expression of liver CYP7A gene (cholesterol 7α-hydroxylase), as well as the liver-specific CYP1A2 gene, remains unchanged in the Alb-VPSXR mice. CYP7A is a key enzyme of bile acid biosynthesis, and a responsive gene of FXR (Forman, et al., 1995, Wang et al, 1999, Park et al., 1999, and Makishima et al., 1999).

EXAMPLE 11

Figure 10:
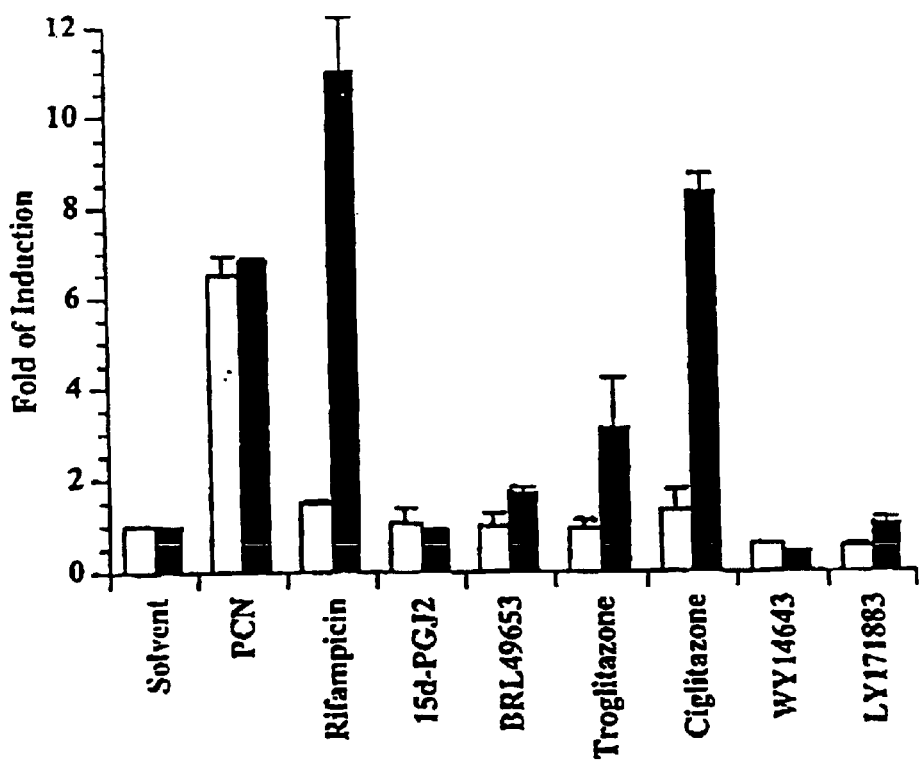
FIG. 10 illustrates the selective activation of SXR by members of the thiazolidinedione family of PPARγ ligands. Thus, the mouse CYP3A23 cellular promoter reporter was transfected into primary rat hepatocytes in the absence (open bars) or presence (filled bars) of expression vector for SXR. Cells were subsequently treated with indicated compounds. Results are shown as fold induction over solvent (DMSO), and represent the averages and standard error from triplicate assays. Note the CYP3A23 was activated by synthetic TZDs troglitazone and ciglitazone (10 μM each) in the presence of SXR, whereas the natural PPARγ ligands 15d-PGJ2 (3 μM), the synthetic BRL49653 (5 μM), as well as the control PPARα specific ligand WY14643 (5 μM), and pan-PPAR ligand LY171883 (30 μM), fail to activate CYP3A23. Cotransfection of expression vector for mouse PXR did not change the response profile (data not shown).

Selective Activation of SXR, but not PXR, by Members of the Thiazolidinedione (TZD) Family of PPARγ Ligands To examine whether TZDs active SXR and/or PXR, rat hepatocytes were transiently transfected with CYP3A23 promoter reporter alone, or together with expression vectors for SXR or PXR. The transfected cells were subsequently treated with a panel of natural PPARγ ligand, or synthetic TZDs. The CYP3A23 gene was not activated by tested PPARγ ligands in the presence of endogenous PXR (FIG. 10A), or with cotransfection of PXR in addition to endogenous proteins (data not shown). On the contrary, in the presence of SXR, while the natural PPARγ ligand 15d-PGJ2 and the synthetic BRL49653 fail to activate, two other synthetic TZDs, troglitazone and ciglitazone, activated CYP3A gene by three folds and eight folds, respectively. As controls, WY 14643, a PPARα-specific ligand, and LY171883, a weak pan-activator for PPARs, fail to activate SXR.

The transfection results were further substantiated by in vivo activation assay. Liver RNAs were harvested 24 h after single dose of TZD treatment via gastric gavage, and subjected to Northern blot analysis. While BRL49653 (20 mg/kg) failed to activate CYP3A gene, troglitazone (150 mg/kg) and ciglitazone (150 mg/kg) selectively up-regulate the expression of CYP3A11 gene is Alb-SXR transgenic mice but not in their nontransgenic littermates. Ciglitazone is a more efficacious CYP3A inducer than troglitazone when administered at same doses, consistent with the hepatocyte transfection results. In comparison with another known SXR activator/CYP3A inducer, treatment of ciglitazone at 150 mg/kg achieved comparable level of CYP3A induction as RIF at 5 mg/kg.

Taken together, the transfection and animal results demonstrated that two TZDs, troglitazone and ciglitazone, are selective activators for human SXR. The SXR-mediated CYP3A gene activation by TZDs, together with the fact that constitutive activation of SXR causes liver toxicity (see below), provides a potential mechanism for the known clinical liver toxicity by certain TZDs.

EXAMPLE 12

Figure 11:
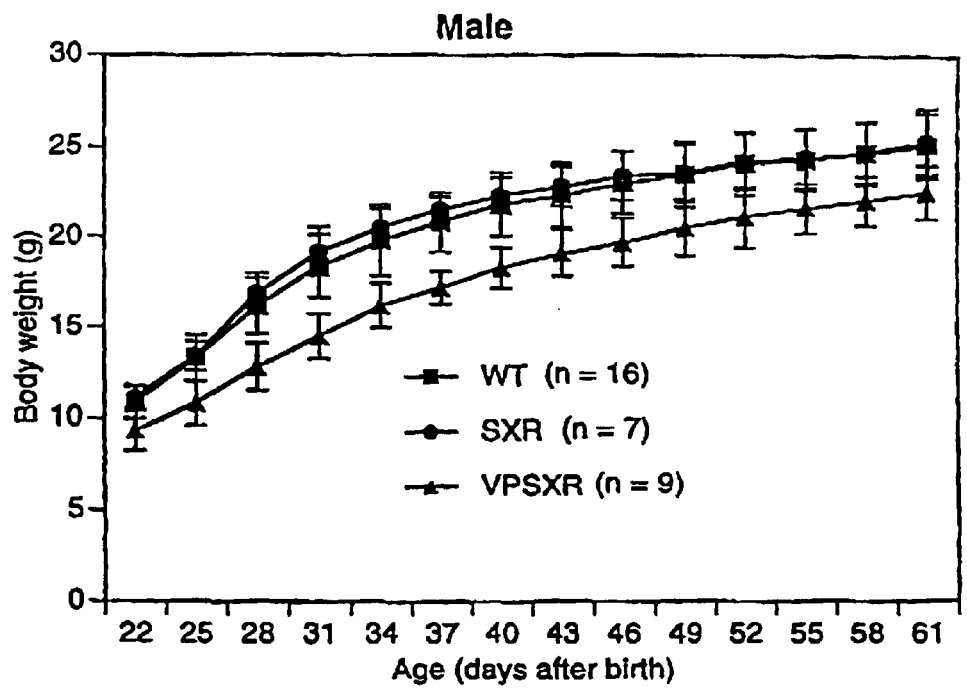
FIG. 11 illustrates growth retardation in Alb-VPSXR transgenic mice. Thus, males of the Alb-VPSXR (n=9), Alb-SXR (n=7) transgenic mice, or their wild type littermates (n=16) were weaned, genotyped and weighted at day 22 after birth, and continue to be weighed every three days thereafter. The results are presented as the averages and standard error. Note the consistent lower body weight in Alb-VPSXR mice.

Constitutive Activation of SXR Results in General Growth Retardation and Liver Toxicity The Alb-VPSXR mice exhibit growth retardation, smaller body size and lower body weight in both sexes were well notable at three week during tail biopsy. Shown in FIG. 11 is the growth curve of Alb-VPSXR males as compared to age- and litter size-matched wild type animals or their Alb-SXR counterparts. The growth retardation of the Alb-VPSXR mice is most apparent at 4–5 weeks of age, with a decrease of about 20% in body weight compared to wild type or Alb-SXR mice. This percentage decreased to about 10% by 8–9 weeks, and persisted thereafter (FIG. 11). A similar pattern of growth retardation was also observed in female transgenics (data not shown). The growth retardation may attribute to liver toxicity as described below. No significant body weight changes were seen in the Alb-SXR mice (FIG. 11), indicating the growth retardation is resulted from constitutive activation of SXR and upregulation of CYP3A gene in mouse liver.

Figure 12:
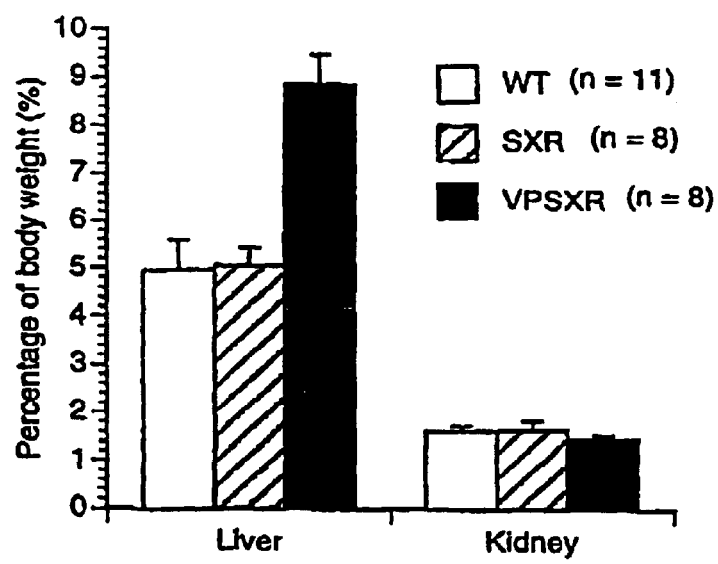
FIG. 12 illustrates the occurance of hepatomegaly in Alb-VPSXR transgenic mice. Thus, two and half months old males of the Alb-VPSXR (n=8), Alb-SXR (n=8) transgenic mice, or their wild type littermates (n=11) were euthanized. The whole liver, kidney, and spleen (data not shown) were dissected and weighed. The organ weights are presented as percentages of total body weight. Note the significant increase in liver weight in the Alb-VPSXR mice.

Autopsy revealed hepatomegaly in the Alb-VPSXR mice. The liver weight of 3.5-week-old Alb-VPSXR males increased by 56% when measured as percentages of body weight (data not shown). The hepatomegaly progressed with age, and by 2.5 months, the liver accounts for 4.95% of total body weight in nontransgenic males; while this percentage is 8.86%, an increase of 79%, in Alb-VPSXR mice (line 2198) (FIG. 12). Indeed, in spite of their lower body weight as described above, the Alb-VPSXR mice had higher absolute liver weight compared to wild type animals. All four liver lobes, the large median lobe, the left lateral lobe, the right lateral lobe, and a caudal lobe, were proportionally enlarged. Macroscopically, the enlarged liver from Alb-VPSXR mice exhibited "nutmeg" features, clinically normally seen as a result of chronic passive congestion of backflow due to heart disease. The hepatomegaly is liver- and Alb-VPSXR transgene-specific, as (1) No significant changes in organ weight and gross appearance were seen in transgene non-expressing organs such as the kidney (FIG. 12), and spleen (data not shown); (2) No liver weight changes were seen in untreated Alb-SXR mice (FIG. 12).

Histologic examination of 2.5 month old Alb-VPSXR transgenics revealed remarkabe differences from their littermates. There is marked microvesicular steatosis which is most pronounced in zone 3 of the liver acinus (around the central veins). There is also substantial nuclear variability with enlarged hepatocyte nuclei, especially in zone 3. Large pinkish vacuoles are seen in many hepatocytes adjacent to the nucleus. These appear to be protein accumulations in the perinuclear Golgi and are similar in appearance to those seen in patients with defects in alpha1-antitrypsin that impair its normal intracellular trafficking. These are distributed across the acinus. Additionally, there are foci of necrotic hepatocytes (pale pink areas) invaded by neutrophils. Gomori's Trichrome stains revealed no significant fibrosis in transgenic livers. However, the protein plugs in the hepatocytes of the transgenics are either very blue or very red, strikingly different from nontransgenic animals. Therefore, there appears to be accumulation of more than one type of proteins as intracellular inclusions.

BrdU labeling and immunostaining was performed to examine the proliferation of hepatocytes in transgenics. Four-week-old wild type and Alb-VPSXR transgenic males were injected intraperitoneally with BrdU and paraffin sections of the livers were prepared for immunostaining with an anti-BrdU antibody. 0.5–1% of the transgenic hepatocyte nuclei are positive for BrdU, and dividing binuclei hepatocytes are notable; whereas the labeled cell is a rare event in their nontransgenic littermates. Consistent patterns of BrdU labeling were observed in multiple animals.

Similar general growth retardation, hepatomegaly and liver histologic changes were also observed in line 2418, another Alb-VPSXR transgenic line with similar levels of transgene expression and constitutive upregulation of CYP3A11 (data not shown), indicating that the observed phenotypic exhibition is a transgene-specific, rather than an integration-specific event. As controls, no histologic changes were seen in kidney and small intestines (data not shown).

EXAMPLE 13

Histologic Evaluation, BrdU Labeling and Immunohistochemistry

Gross and microscopic evaluation were performed. Tissues were fixed in 4% formaldehyde in 1×PBS, embedded in paraffin, sectioned at 5 µm. Hematoxylin and eosin stains, or the Gomori's trichrome stains were performed for histological examination. In vivo BrdU labeling was performed by intraperitoneal injection of BrdU (Sigma) as described (Xie et al., 1998). The sections were immunostained with a rat monoclonal anti-BrdU antibody MSA250P (1:200) (Accurate) using Vectastain Elite ABC Kit (Vector). The chromogen is 3,3'-diaminobenzidine tetrahydrochloride (DAB), and sections were counterstained with Gill's Hematoxylin (Vector).

It will be apparent to those skilled in the art that various changes may be made in the invention without departing from the spirit and scope thereof, and therefore, the invention encompasses embodiments in addition to those specifically disclosed in the specification, but only as indicated in the appended claims.

We claim:

1. A transgenic mouse whose genome contains a transgene comprising a gene encoding a human steroid and xenobiotic receptor (SXR) polypeptide operably linked to an albumin promoter/enhancer,
   wherein said SXR polypeptide is a member of the steroid/thyroid hormone superfamily and forms a heterodimer with retinoid X receptor,
   wherein said heterodimer binds to a direct or inverted repeat response element comprising at least two half sites RGBNNM separated by a spacer of 0 up to 15 nucleotides,
   wherein:
      R is selected from A or G;
      B is selected from G, C, or T;
      each N is independently selected from A, T, C, or G; and
      M is selected from A or C;
   with the proviso that at least 4 nucleotides of said -RGBNNM- sequence are identical with the nucleotides at corresponding positions of the sequence AGTTCA;
   wherein said transgenic mouse expresses said SXR polypeptide, and
   wherein said SXR polypeptide inducibly activates transcription in response to a wide variety of natural and synthetic steroid hormones, including at least compounds that induce catabolic enzymes, steroid receptor agonists and antagonists, and bioactive dietary compounds.

2. A transgenic mouse according to claim 1, wherein, upon expression of said SXR polypeptide, said transgenic mouse responds to natural and synthetic steroid hormones to which a wild type mouse does not respond.

3. A transgenic mouse according to claim 1, wherein said SXR polypeptide comprises an SXR ligand binding domain and a DNA binding domain obtained from a transcription activating factor.

4. A transgenic mouse according to claim 1, wherein the ligand binding domain and DNA binding domain of said SXR polypeptide are obtained from SXR.

5. A transgenic mouse according to claim 1, wherein said mouse further comprises a nucleic acid sequence which comprises:
   (a) a promoter that is operable in said mouse,
   (b) a hormone response element, and
   (c) DNA encoding a protein,
   wherein said protein-encoding DNA is operatively linked to said promoter for transcription of said DNA, and
   wherein said promoter is operatively linked to said hormone response element for activation thereof.

6. A transgenic mouse according to claim 5, wherein said protein is a reporter.

7. A transgenic mouse according to claim 5, wherein said protein is a mammalian cytochrome p450.

8. A transgenic mouse according to claim 1, wherein the transgene further comprises nucleic acid sequence encoding VP16.

9. Cells derived from a transgenic mouse according to claim 1.

10. A transgenic knock-out mouse whose genome comprises a homozygous disruption in an endogenous SXR polypeptide gene, wherein said homozygous disruption prevents function of an endogenous SXR polypeptide and results in said transgenic knockout mouse exhibiting decreased response to steroids and xenobiotics as compared to a wild-type mouse.

11. A transgenic mouse whose genome contains a transgene comprising a gene encoding a human steroid and xenobiotic receptor (SXR) polypeptide operably linked to an albumin promoter/enhancer and the VP16 activation domain,
wherein said SXR polypeptide is a member of the steroid/thyroid hormone superfamily and forms a heterodimer with retinoid X receptor,
wherein said heterodimer binds to a direct or inverted repeat response element comprising at least two half sites RGBNNM separated by a spacer of 0 up to 15 nucleotides,
wherein:
R is selected from A or G;
B is selected from G, C, or T;
each N is independently selected from A, T, C, or G; and
M is selected from A or C;
with the proviso that at least 4 nucleotides of said -RGBNNM- sequence are identical with the nucleotides at corresponding positions of the sequence AGTTCA;
wherein said transgenic mouse expresses said SXR polypeptide, and
wherein SXR polypeptide inducibly activates transcription in response to a wide variety of natural and synthetic steroid hormones, including at least compounds that induce catabolic enzymes, steroid receptor agonists and antagonists, and bioactive dietary compounds.

12. A transgenic mouse according to claim 11, wherein expression of said SXR polypeptide results in growth retardation and hepatomegaly in said mouse.

13. A transgenic mouse according to claim 11, wherein said SXR polypeptide comprises an SXR ligand binding domain and a DNA binding domain obtained from a transcription activating factor.

14. A transgenic mouse according to claim 11, wherein the ligand binding domain and DNA binding domain of said SXR polypeptide are obtained from SXR.

15. A transgenic mouse according to claim 11, wherein said mouse further comprises a nucleic acid sequence which comprises:
(a) a promoter that is operable in said mouse,
(b) a hormone response element, and
(c) DNA encoding a protein,
wherein said protein-encoding DNA is operatively linked to said promoter for transcription of said DNA, and
wherein said promoter is operatively linked to said hormone response element for activation thereof.

16. A transgenic mouse according to claim 15, wherein said protein is a reporter.

17. A transgenic mouse according to claim 15, wherein said protein is a mammalian cytochrome p450.

18. A transgenic mouse according to claim 15, wherein the response element in the reporter vector comprises the half site RGBNNM,
wherein:
R is selected from A or G;
B is selected from G, C, or T;
each N is independently selected from A, T, C, or G; and
M is selected from A or C;
with the proviso that at least 4 nucleotides of said -RGBNNM- sequence are identical with the nucleotides at corresponding positions of the sequence AGTTCA.

19. Cells derived from a transgenic mouse according to claim 11.

20. A method for producing a transgenic mouse, said method comprising:
injecting a one-cell mouse zygote with a transgene comprising a gene encoding a human steroid and xenobiotic receptor (SXR) polypeptide operably linked to an inducible or a constitutively active albumin promoter/enhancer,
wherein said SXR polypeptide is a member of the steroid/thyroid hormone superfamily and forms a heterodimer with retinoid X receptor,
wherein said heterodimer binds to a direct or inverted repeat response element comprising at least two half sites RGBNNM separated by a spacer of 0 up to 15 nucleotides,
wherein:
R is selected from A or G;
B is selected from G, C, or T;
each N is independently selected from A, T, C, or G; and
M is selected from A or C;
with the proviso that at least 4 nucleotides of said -RGBNNM- sequence are identical with the nucleotides at corresponding positions of the sequence AGTTCA,
wherein said transgenic mouse expresses said SXR polypeptide, and
wherein said SXR polypeptide inducibly or constitutively activates transcription in response to a wide variety of natural and synthetic steroid hormones, including at least compounds that induce catabolic enzymes, steroid receptor agonists and antagonists, and bioactive dietary compounds, and
obtaining from the zygote a transgenic mouse that expresses said SXR polypeptide in the liver.

21. A method according to claim 20, wherein expression of said SXR polypeptide activates in the transgenic mouse a response to natural and synthetic steroid hormones to which a wild type mouse does not respond.

22. A method according to claim 20, wherein the promoter/enhancer is an inducible albumin promoter/enhancer.

23. A method according to claim 20, wherein the albumin promoter/enhancer further comprises a constitutively active VP16 promoter/enhancer.

24. A transgenic mouse whose genome contains a transgene comprising a gene encoding a human steroid xenobiotic receptor (SXR) polypeptide, or functional fragment of said polypeptide, operably linked to an albumin promoter/enhancer,
wherein said human SXR polypeptide is inducibly expressed in said transgenic mouse in a tissue-specific manner,
wherein said human SXR polypeptide is a member of the steroid/thyroid hormone superfamily and forms a heterodimer with retinoid X receptor,
wherein said heterodimer binds to a direct or inverted repeat response element comprising at least two half sites RGBNNM separated from a spacer of 0 up to 15 nucleotides, wherein:

R is selected from A or G;

B is selected from G, C, or T;

each N is independently selected from A, T, C, or G; and

M is selected from A or C;

with the proviso that at least 4 nucleotides of said RGBNNM sequence are identical with the nucleotides at corresponding positions of the sequence AGTTCA; and wherein compounds selected from the group consisting of natural and synthetic steroid hormones including at least compounds that induce catabolic enzymes, steroid receptor agonists and antagonists, and bioactive dietary compounds, interact with said human SXR polypeptide directly or indirectly to activate transcription of a gene under the control of a cytochrome P450 response element therefore.

25. A transgenic knock-out mouse whose genome comprises a homozygous disruption in an endogenous mouse SXR polypeptide gene, wherein said homozygous disruption comprises insertion, deletion or point mutation of said mouse SXR polypeptide, wherein said disruption results in a decrease in transcription of a gene under the control of a cytochrome P450 response element mediated by said mouse SXR polypeptide in said transgenic knockout mouse as compared to a wild-type mouse.

26. A method for producing a transgenic mouse, said method comprising:

injecting a one-cell mouse zygote with a transgene comprising a gene encoding a human steroid xenobiotic receptor (SXR) polypeptide , or functional fragment of said polypeptide, operably linked to an inducible or a constitutively active tissue-specific albumin promoter/enhancer, wherein said human SXR polypeptide is inducibly or constitutively expressed in said transgenic mouse in a tissue-specific manner, wherein said human SXR polypeptide is a member of steroid/thyroid hormone superfamily and forms a heterodimer with retinoid X receptor, wherein said heterodimer binds to a direct or inverted repeat response element comprising at least two half sites RGBNNM separated by a spacer of 0 up to 15 nucleotides, wherein:

R is selected from A or G;

B is selected from G, C, or T;

each N is independently selected from A, T, C, or G; and

M is selected from A or C;

with the proviso that at least 4 nucleotides of said -RGBNNM- sequence are identical with nucleotides at corresponding positions of the sequence AGTTCA, wherein compounds selected from the group consisting of natural and synthetic steroid hormones including at least compounds that induce catabolic enzymes, steroid receptor agonists and antagonists, and bioactive dietary compounds, interact with said human SXR polypeptide directly or indirectly to activate transcription of a gene under the control of a cytochrome P450 response element therefore, and obtaining a transgenic mouse from said mouse zygote, wherein said transgene is incorporated into the genome of said transgenic mouse and wherein said transgenic mouse expresses said human SXR polypeptide.

27. A transgenic mouse whose genome contains a transgene comprising a gene encoding a human steroid xenobiotic receptor (SXR) polypeptide, or functional fragments of said polypeptide, operably linked to an albumin promoter/enhancer and the VP16 activation domain, wherein said human SXR polypeptide is constitutively expressed in said transgenic mouse in a tissue-specific manner, wherein said human SXR polypeptide is a member of the steroid/thyroid hormone superfamily and forms a heterodimer with retinoid X receptor, wherein said heterodimer binds to a direct or inverted repeat response element comprising at least two half sites RGBNNM separated by a spacer of 0 up to 15 nucleotides, wherein:

R is selected from A or G;

B is selected from G, C, or T;

each N is independently selected from A, T, C, or G; and

M is selected from A or C;

with the proviso that at least 4 nucleotides of said RGBNNM sequence are identical with the nucleotides at corresponding positions of the sequence AGTTCA; and wherein compounds selected from the group consisting of natural and synthetic steroid hormones including at least compounds that induce catabolic enzymes, steroid receptor agonists and antagonists, and bioactive dietary compounds, interact with said human SXR polypeptide directly or indirectly to activate transcription of a gene under the control of a cytochrome P450 response element therefore.

* * * * *